US005565332A

United States Patent [19]
Hoogenboom et al.

[11] Patent Number: 5,565,332
[45] Date of Patent: Oct. 15, 1996

[54] PRODUCTION OF CHIMERIC ANTIBODIES - A COMBINATORIAL APPROACH

[75] Inventors: Hendricus R. J. M. Hoogenboom, Cambridge, United Kingdom; Michael Baier, Frankfurt, Germany; Laurent S. A. T. Jespers, Tervuren, Belgium; Gregory P. Winter, Cambridge, United Kingdom

[73] Assignees: Medical Research Council, London; Cambridge Antibody Technology Limited, Melbourn, both of England

[21] Appl. No.: 211,202

[22] PCT Filed: Sep. 23, 1992

[86] PCT No.: PCT/GB92/01755

§ 371 Date: Jun. 24, 1994

§ 102(e) Date: Jun. 24, 1994

[87] PCT Pub. No.: WO93/06213

PCT Pub. Date: Apr. 1, 1993

[30] Foreign Application Priority Data

Sep. 23, 1991 [GB] United Kingdom .................. 9120252
Sep. 25, 1991 [GB] United Kingdom .................. 9120377
Mar. 24, 1992 [GB] United Kingdom .................. 9206318
Mar. 24, 1992 [GB] United Kingdom .................. 9206372

[51] Int. Cl.$^6$ .......................... A61K 35/16; A61K 39/00; C07K 16/00
[52] U.S. Cl. .............. 435/69.1; 435/5; 435/69.7; 435/69.8; 435/91.1; 435/235.1; 435/252.3; 435/252.33; 435/320.1; 530/387.1; 530/387.3; 530/867; 536/23.1; 536/23.4; 536/23.33
[58] Field of Search .................. 530/387.1, 387.3, 530/867; 435/5, 91.1, 69.1, 69.7, 69.8, 235.1, 320.1, 252.3, 252.33; 536/23.1, 23.53, 23.4

[56] References Cited

FOREIGN PATENT DOCUMENTS

| | | |
|---|---|---|
| 2188638 | 10/1987 | United Kingdom . |
| 8806630 | 9/1988 | WIPO . |
| 9014443 | 11/1990 | WIPO . |
| WO91/05260 | 4/1991 | WIPO . |
| WO92/01047 | 1/1992 | WIPO . |
| WO92/20791 | 11/1992 | WIPO . |

OTHER PUBLICATIONS

Amit et al., Three–Dimensional Structure of an Antigen–Antibody Complex at 2.8 Å Resolution, *Science* 233:747–753 (1986).
Berman et al., Content and organization of the human 1g $V_H$ locus: definition of three new $V_H$ families and linkage to the 1g $C_H$ locus, *Embo. J* 7:727–738 (1988).
Bird et al., Single–Chain Antigen–Binding Proteins, *Science* 242:423–426 (1988).
Bosslet et al., Molecular and functional characterisation of a fusion protein suited for tumour specific prodrug activation, *Brit. J. Cancer* 65:234–238 (1992).
Carter et al., Humanization of anti-$p^{HER2}$ antibody for human cancer therapy, *Proc. Natl. Acad. Sci. USA* 89:4285–4289(1992).
Chen et al., A 16/6 Idiotype–Positive Anti–DNA Antibody is Encoded by a Conserved $V_H$ Gene With No Somatic Mutation, *Arthritis Rheum* 31:1429–1431 (1988).
Chothia et al., Canonical Structures for the Hypervariable Regions of Immunoglobulins, *J. Mol. Biol.* 196:901–917 (1987).
Chothia et al., Structural Repertoire of the Human $V_H$ Segments, *J. Mol. Biol.* 227:789–817 (1992).
Clackson et al., Making antibody fragments using phage display libraries, *Nature* 352:264–628 (1991).
Co et al., Humanized antibodies for antiviral therapy, *Proc. Natl. Acad. Sci. USA* 88:2869–2873 (1991).
Daugherty et al., Polymerase chain reaction facilitates the cloning, CDR–grafting, and rapid expression of a murine monoclonal antibody directed against the CD18 component of leukocyte integrins, *Nucl. Acids Res.* 19:2471–2476 (1991).
Dreher et al., Colony assays for antibody fragments expressed in bacteria, *J. Immunol. Methods* 139:197–205 (1991).
Foote et al., Antibody Framework Residues Affecting the Conformation of the Hypervariable Loops, *J. Mol. Biol.* 224:487–499 (1992).
Foote et al., Kinetic maturation of an immune response, *Nature* 352:530–532 (1991).

(List continued on next page.)

*Primary Examiner*—Donald E. Adams
*Attorney, Agent, or Firm*—Marshall, O'Toole, Gerstein, Murray & Borun

[57] ABSTRACT

Methods are disclosed which may be used for the production of antibodies, or antibody fragments, which have the same binding specificity as a parent antibody but which have increased human characteristics. Humanized antibodies may be obtained by chain shuffling, perhaps using phage display technology. In one embodiment, a polypeptide comprising a heavy or light chain variable domain of a non-human antibody specific for an antigen of interest is combined with a repertoire of human complementary (light or heavy) chain variable domains. Hybrid pairings which are specific for the antigen of interest are selected. Human chains from the selected pairings may then be combined with a repertoire of human complementary variable domains (heavy or light) and humanized antibody polypeptide dimers can then be selected for binding specificity for antigen. The methods may be combined with CDR-imprinting. In another embodiment, component part of an antigen-binding site of a no-human antibody known to bind a particular antigen is combined with a repertoire of component parts of an antigen-binding site of human antibody, forming a library of antibody polypeptide dimers with antigen-binding sites. Hybrids selected from this library may be used in a second humanizing shuffling step, or may already be of sufficient human character to be of value, perhaps after some modification to increase human character still further.

26 Claims, 18 Drawing Sheets

OTHER PUBLICATIONS

Frippiat et al., First genomic sequence of a human lg variable lambda gene belonging to subgroup III, *Nucleic Acids Res.* 18:7134 (1990).

Hoogenboom et al., By–passing Immunisation—Human Antibodies from Synthetic Repertoires of Germline $V_H$ Gene Segments Rearranged in Vitro, *J. Mol. Biol.* 227:381–388 (1992).

Hoogenboom et al., Multi–subunit proteins on the surface of filamentous phage: methodologies for displaying antibody (Fab) heavy and light chains, *Nucl. Acids Res.* 19:4133–4137 (1991).

Huse et al., Generation of a Large Combinatorial Library of the Immunoglobulin Repertoire in Phage Lambda, *Science* 246:1275–1281 (1989).

Huston et al., Protein engineering of antibody binding sites: Recovery of specific activity in an anti–digoxin single–chain Fv analogue produced in Escherichia coli, *Proc. Natl. Acad. Sci. USA* 85:5879–5883 (1988).

Kang et al., Antibody redesign by chain shuffling from random combinatorial immunoglobulin libraries, *Proc. Natl. Acad. Sci. USA* 88:11120–11123 (1991).

Kang et al., Linkage of recognition and replication functions by assembling combinatorial antibody Fab libraries along phage surfaces, *Proc. Natl. Acad. Sci. USA* 88:4363–4366 (1991).

Kettleborough et al., Humanization of a mouse monoclonal antibody by CDR–grafting: the importance of framework residues on loop conformation, *Protein Eng.* 4:773–783 (1991).

Marks et al., By–passing Immunization—Human Antibodies from V–gene Libraries Displayed on Phage, *J. Mol. Biol.* 222:581–597 (1991); and Example 1.

Marks et al., By–Passing Immunization: Building High Affinity Human Antibodies by Chain Shuffling, *Bio/Technology* 10:779–783 (1992).

Mathyssens et al., Structure and multiplicity of genes for the human immunoglobulin heavy chain variable region, *Proc. Natl. Acad. Sci. USA* 77:6561–6565 (1980).

McCafferty et al., Phage antibodies: filamentous phage displaying antibody variable domains, *Nature* 348:552–554 (1990).

Milstein C., Antibodies: a paradigm for the biology of molecular recognition, *C. Proc. R. Soc. Lond. Biol.* 239:1–16 (1990).

Orlandi et al., Cloning immunoglobulin variable domains for expression by the polymerase chain reaction, *Proc. Natl. Acad. Sci. USA* 86(10):3833–3837 (1989).

Padlan et al., A Possible Procedure for Reducing the Immunogenicity of Antibody Variable Domains While Preserving Their Ligand–Binding Properties, *Mol. Immunol.* 28:485–498 (1991).

Queen et al., A humanized antibody that binds to the interleukin 2 receptor, *Proc. Natl. Acad. Sci. USA* 86:10029–10033 (1989).

Rath et al., An inhibition enzyme immunoassay for estimating relative antibody affinity and affinity heterogeneity, *J. Immunol. Methods* 106:245–249 (1988).

Rathjen et al., Antigenic Structure of Human Tumour Necrosis Factor: Recognition of Distinct Regions of TNFα by Different Tumour Cell Receptors, *Mol. Immunol.* 28:79 (1991).

Riechmann et al., Reshaping human antibodies for therapy, *Nature* 332:323–327 (1988).

Sanz et al., The smaller human $V_H$ gene families display remarkably little polymorphism, *Embo. J.* 8:3741–3748 (1989).

Skerra et al., Filter Screening of Antibody Fab Fragments Secreted from Individual Bacterial Colonies: Specific Detection of Antigen Binding with a Two–Membrane System, *Anal. Biochem.* 196:151–155 (1991).

Taub et al., A Monoclonal Antibody against the Platelet Fibrinogen Receptor Contains a Sequence That Mimics a Receptor Recognition Domain in Fibrinogen, *J. Biol. Chem.* 364–265 (1989).

Tempest et al., Reshaping a Human Monoclonal Antibody to Inhibit Human Respiratory Syncytial Virus Infection In Vivo, *Bio/Technology* 9:266–271 (1991).

Tomlinson et al., The Repertoire of Human Germline $V_V$ Sequences Reveals about Fifty Groups of $V_H$ Segments with Different Hypervariable Loops, *J. Mol. Biol.* 227:776–798 (1992); Fig. 6.

Ward et al., Binding activities of a repertoire of single immunoglobulin variable domains secreted from Escherichia coli, *Nature* 341:544–546 (1989).

Winter et al., Man–made antibodies, *Nature* 349:293–299 (1991).

FIG. 2

```
                                    rbs                      M  K  Y  L  L  P  T  A
GCATGCAAATTCTATTTCAAGGAGACAGTCATAATGAAATACCTATTGCCTACGGCAGCC
         10        20        30        40        50        60
SphI PelB leader
 A  G  L  L  L  L  A  A  Q  P  A  M  A  Q  V  Q  L  Q  V  D
GCTGGATTGTTATTACTCGCGGCCCAGCCATGGCCCAGGTGCAGCTGCAGgtcgac
         70        80        90       100       110
                         SfiI                    PstI  SalI Myc Tag (TAG1)
 L  E  I  K  R  A  A  A  E  Q  K  L  I  S  E  E  D  L  N  *
CTCGAGATCAAACGGGCCGCAGAACAAAAACTCATCTCAGAAGAGGATCTGAATTAA
         120       130       140       150       160       170
XhoI           NotI

*TAAGAATTC
     EcoRI
```

FIG. 5A

MAB32-HEAVY CHAIN V-GENE

```
1
CAG GTC AAA CTG CAG CAG TCA GGG GCT GAG CTT GTG AAG CCT GGG GCT TCA GTG AAA ATG
GLN VAL LYS LEU GLN GLN SER GLY ALA GLU LEU VAL LYS PRO GLY ALA SER VAL LYS MET
61
TCC TGC AAG GCT TCT GGC TAT ACC TTC GCC AGC TAC TGG ATA AAC TGG GTG AAG CAG AGG
SER CYS LYS ALA SER GLY TYR THR PHE ALA SER TYR TRP ILE ASN TRP VAL LYS GLN ARG
121
CCT GGA CAA GGC CTT GAG TGG ATT GGA CAT ATT TAT CCT GTT AGA AGT ATT ACT AAG TAC
PRO GLY GLN GLY LEU GLU TRP ILE GLY HIS ILE TYR PRO VAL ARG SER ILE THR LYS TYR
181
AAT GAG AAG TTC AAG AGT AAG GCC ACA CTG ACT CTA GAC ACA TCC AGC ACA GCC TAC
ASN GLU LYS PHE LYS SER LYS ALA THR LEU THR LEU ASP THR SER SER THR ALA TYR
241
ATG CAG CTC AGC AGC CTG ACA TCT GAG GAC TCT GCG GTC TAT TAT TGT TCA AGA GGG GAC
MET GLN LEU SER SER LEU THR SER GLU ASP SER ALA VAL TYR TYR CYS SER ARG GLY ASP
301
GGC AGT GAT TAT TAT GCT ATG GAC TAC TGG GGC CAA GGG ACC ACG GTC ACC GTC TCC TCA
GLY SER ASP TYR TYR ALA MET ASP TYR TRP GLY GLN GLY THR THR VAL THR VAL SER SER
```

FIG. 5B

MAB32-LIGHT CHAIN V-GENE

```
1
GAC ATT GAG CTC ACC CAG TCT CCA GCA ATC CTG TCT GCA TCT CCA GGG GGG AAG GTC ACA
ASP ILE GLU LEU THR GLN SER PRO ALA ILE LEU SER ALA SER PRO GLY GLY LYS VAL THR
61
ATG ACT TGT AGG GCC AGC TCA AGT GTA AGT TAC ATG CAC TGG TAC CAG CAG AAG CCA GGA
MET THR CYS ARG ALA SER SER SER VAL SER TYR MET HIS TRP TYR GLN GLN LYS PRO GLY
121
TCC CCC AAA CCC TGG ATT TAT GCC ACA TCC AAC CTG GCT TCT GGA GTC CCT ACT CGC
SER SER PRO LYS PRO TRP ILE TYR ALA THR SER ASN LEU ALA SER GLY VAL PRO THR ARG
181
TTC AGT GGC ACT GGG TCT GGG ACC TCT TAC TCT CTC ACA ATC AGC AGG GTG GAG GCT GAA
PHE SER GLY THR GLY SER GLY THR SER TYR SER LEU THR ILE SER ARG VAL GLU ALA GLU
241
GAT GCT GCC ACT TAT TAC TGC CAG CAG TGG AGT CGT AAC CCA TTC ACG TTC GGC TCG GGC
ASP ALA ALA THR TYR TYR CYS GLN GLN TRP SER ARG ASN PRO PHE THR PHE GLY SER GLY
301
ACC AAG CTG GAA ATC AAA CGG
THR LYS LEU GLU ILE LYS ARG
```

FIG. 6A

DEDUCED PROTEIN SEQUENCE OF $V_H$ AND $V_L$ GENES OF ANTIBODY FRAGMENTS BINDING TO HUMAN TNF.

A. LIGHT CHAINS

| CLONE | FR1 | CDR1 | FR2 | CDR2 |
|---|---|---|---|---|
| MAB32 | AIELTQPAILSASPGGKVTMTC | RASSSVSYMH | WYQQKPGSSPKPWIY | ATSNLAS |
| Vλ1-1-1 | QSVLTQPPSASGTPGQRVTISC | SGSSSNIGSNYVY | WYQQLPGTAPKLLIY | RNNQRPS |
| VλA2 | -----S-V-AA---K---- | -------N---- | ------------- | ------- |
| VλC4 | -----S------------- | ------------ | ------------- | ------- |
| VλD1 | -----A------------- | ------------ | ------R------ | ------- |

| CLONE | FR3 | CDR3 | FR4 |
|---|---|---|---|
| MAB32 | GVPTRFSGSGTGTSYSLTISRVEAEDAATYYC | QQWSRNPFT | FGSGTKLEIK |
| Vλ1-1-1 | GVPDRFSGSKSGTSASLAISGLRSEDEADYYC | AAWDDSLSG | |
| VλA2 | -------------------------------- | ------RRVV | FGGGTKLTVLG |
| VλC4 | ---------S---------------------- | ------RDVV | FGGGTKLTVLG |
| VλD1 | -------------------------------- | ------RVYV | FGTGTKVTVLG |

FIG. 6B

B. HEAVY CHAINS

| CLONE | FR1 | CDR1 | FR2 | CDR2 |
|---|---|---|---|---|
| MAB32 | QVKLQQSGAELVKPGASVKMSCKASGYTFA | SYWIN | WVKQRPGQGLEWIG | HIYPVRSITKYNEKFKS |
| DP-51 | EVQLVESGGGLVQPGGSLRLSCAASGFTFS | SYSMN | WVRQAPGKGLEWVS | YISSSSSTIYYADSVKG |
| V_H P1 | Q----LQ--------------------- | --A-S | -------------- | ----------------- |
| V_H P2 | Q--------------------------- | ------ | -------------- | -------G--------- |
| V_H P3 | -----Q---------------------- | ------ | -------------- | ----------------- |
| DP-46 | QVQLVESGGGVVQPGRSLRLSCAASGFTFS | SYAMH | WVRQAPGKGLEWVA | VISYDGSNKYYADSVKG |
| V_H LM2 | -----Q------L-K--G---------- | ------ | -------------- | ----------------- |
| V_H LM8 | ---------------------------- | ------ | -------------- | ----------------- |

| CLONE | FR3 | CDR3 | FR4 |
|---|---|---|---|
| MAB32 | KATLTLDTSSSTAYMQLSSLTSEDSAVYYCSR | GDGSDYYAMDY | WGQG |
| DP-51 | RFTISRDNAKNSLYLQMNSLRDEDTAVYYCAR | | |
| V_H P1 | ------------T------------------ | SLVGALDY | WGQG |
| V_H P2 | ------------------------------S | SSWYGGYGDY | WGQG |

FIG. 6C

```
V_H P3    ------------A-------                        SVDSYGMDV          WGQG
DP-46     RFTISRDNSKNTLYLQMNSLRAEDTAVYYCAR
V_H LM2   -------------------------------K           GGLGTYYYDSSGHKGFDP  WGQG
V_H LM8   -------------------------------S           GRYCSGGSCSPFDY      WGQG
```

FR, FRAMEWORK REGION; CDR, COMPLEMENTARY-DETERMINING REGION.

FIG. 9
1. Generation of pHENMBF 58 VL
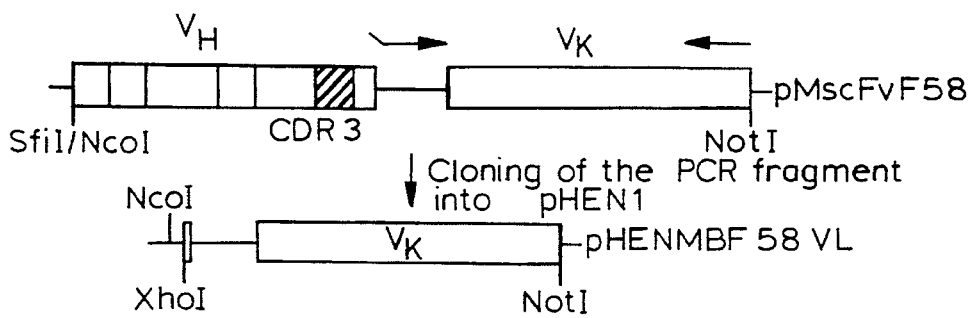
2. Cloning of a CDR3 grafted human VH repertoire
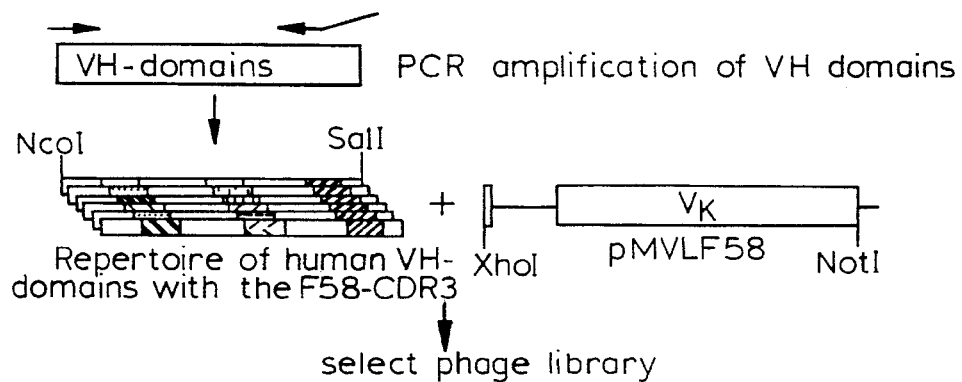
3. PCR assembly of selected VHs with a human VL-repertoire
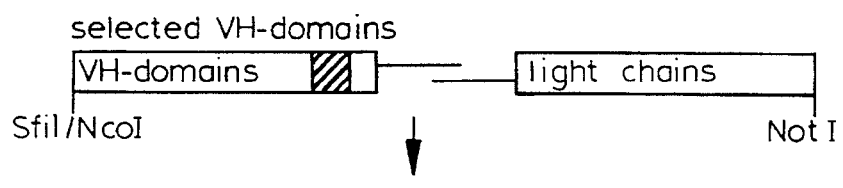
Cloning of the assembled products into pHEN1
4. Select phage library and identify individual binders by ELISA

Fig. 11A

DEDUCED AMINO ACID SEQUENCES OF SELECTED HEAVY CHAINS

A) VH6

```
QVQLQQSGAELASPGASVTLSCKASGYTFT DHIMN  WVKKRPGQGLEWIG RIFPVSGETNYNQFMG  F58
QVQLQQSGPGLVKPSQTLSLTCAISGDSVS SNSAAWN WIRQSPSRGLEWLG RTYYRSKWYNDYAVSVKS DP-74
.....V........................ .......Y..............N............. GRAFT/27
....E................IR....... .K..T.................R..T..T..Q..... GRAFT/2
.......M...................... .S.ST.D.............................. GRAFT/H3
............................... ...................................... GRAFT/H9

KARFSVDRSSSTVSMVLNSLTSE DPAVYYCDL  F58
RITINPDTSKNQFSLQLNSVTPE DTAVYYCAR  DP-74
...I...G...............K.....DL   GRAFT/27
..........S...............   DL   GRAFT/2
............M..............S..DL   GRAFT/H3
....KA........S...............DP   GRAFT/H9
```

```
QVQLQQSGAELASPGASVTLSCKASGYTFT DHIMN WVKKRPGQGLEWIG RIFPVSGETNYNQFMG   F58
QMQLVQSGPEVKKPGTSVKVSCKASGFTFT SSAVQ WVRQARGQRLEWIG WIVVGSGNTNYAQKFQE   DP-2
.VNLRE..A.............A........           .......        P........G.IPIF.TA......G  GRAFT/20

KARFSVDRSSSTVSMVLNSLTSE DPAVYYCDL   F58
RVTITRDMSTSTAYMELSSLRSE DTAVYYCAA   DP-2
....A.E..........G..    .A......DL  GRAFT/20
``` pCANTAB-3myc

FIG. 13

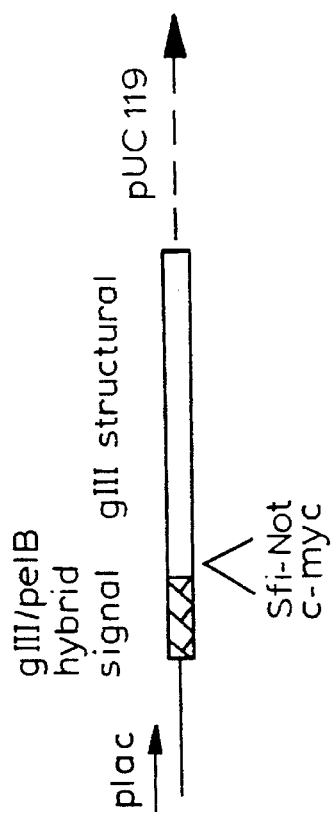

```
                                                                               -1
         V   K   K   L   L   F   A   I   P   L   V   V   F   Y   A   A   Q   P   A   M   A   Q
-----CAT LEADER------- GTG AAA AAA TTA TTA TTC GCA ATT CCT TTA GTT GTT TTC TAT GCG GCC CAG CCG GCC ATG GCC CAG
                                                                                       SfiI          NcoI

A   E   Q   K   L   I   S   E
 GCA GAA CAA AAA CTC ATC TCA GAA
 ======== c-myc tag ========

V   Q   L   Q   V   D   L   E   I   K   R   A   A   A   E
 GTC CAA CTG CAG GTC GAC CTC GAG ATC AAA CGG GCG GCC GCA
     PstI       SalI       XhoI           NotI

E   D   L   N   G   A   A   (E)   T   V   E
 GAG GAT CTG AAT GGG GCC GCA TAG ACT GTT GAA -----
                        |+1  ---- fd gene III
``` pCANTAB-5myc

PRODUCTION OF CHIMERIC ANTIBODIES - A COMBINATORIAL APPROACH

The present invention relates to the production of antibodies. More particularly, it relates to the production of antibodies with increased human characteristics over a parent antibody specific for the same antigen.

Many rodent monoclonal antibodies have been isolated using hybridoma technology and utilised for in vivo therapeutic and diagnostic purposes in humans. For example, an early application of these mouse monoclonal antibodies was as targeting agents to kill or image tumours (F. H. Deland and D. M. Goldenberg 1982 in 'Radionuclide Imaging' ed. D. E. Kuhl pp289–297, Pergamon, Paris; R. Levy and R. A. Miller Ann. Rev. Med. 1983, 34 pp107–116). However, the use of such antibodies in vivo can lead to problems. The foreign immunoglobulins can elicit an anti-globulin response (known as a human anti-mouse antibody (HAMA) response) which can interfere with therapy (R. A. Miller et al, 1983 Blood 62 988–995) or cause allergic or immune complex hypersensitivity (B. Ratner, 1943, Allergy, Anaphylaxis and Immunotherapy Williams and Wilkins, Baltimore).

To overcome these problems, Winter and colleagues (GB2188638B) developed a method of humanising or "reshaping' such antibodies. The complementarity determining regions (CDRs) of the mouse antibody, which comprise the antigen combining site, are inserted into human framework regions thereby generating antibodies in which only the CDR sequences are derived from the original mouse antibody. This is the technique known as "CDR-grafting" or "CDR-imprinting". One such reshaped antibody CAM-PATH-1 (L. Riechmann et al, 1988 Nature 332, pp323–327 has been used successfully in the treatment of B cell lymphoma (G. Hale et al, 1988 Lancet 2, pp1394–1399) and vasculitis (P. W. Mathieson et al New Engl. J. Med. 1990 323, pp250–254) and rheumatoid arthritis (V. Kyle et at 1991 J. Rheumatol. 18, pp1737–1738). This has prompted the humanisation of a large number of antibodies for therapeutic purposes directed against cancer markers, for example the interleukin 2 receptor (C. Queen et al, 1989 Proc. Natl. Acad. Sci. USA, 86, pp10029–10033); epidermal growth factor receptor (C. A. Kettleborough et al 1991 Protein Eng. 4, pp773–783; P. Carter et al 1992 Proc. Natl. Acad. Sci. USA 89, pp4285–4289) and carcinoembryonic antigen (K. Bosslet et al. Brit. J. Cancer 65, pp234–238, 1992). A number of antibodies directed against infectious viruses have also been humanised, for instance antibodies directed against respiratory syncytial virus (P. R. Tempest et al, 1991 Bio/Technology 9, pp266–271); herpes simplex virus (M. S. Co et al 1991 Proc. Natl. Acad. Sci. USA 88, pp2869–2873) and human immunodeficiency virus (H. Maeda et al 1991 Human Antibodies and Hybridomas 2, pp124–134). Humanised antibodies have also been used for imaging tumours after labelling with radioisotopes (V. Hird et al, 1991 Brit. J. Cancer 64 911–914).

Successful reshaping depends on the rodent and human framework regions being structurally conserved both in the orientation of the beta-sheets of each domain and in the packing of the heavy and light chains together; the hypervariable loops making the majority of contacts with antigen and the loops being supported in a similar way by the underlying beta-sheet framework. Although these conditions are likely to be true for some antibodies, the restitution of key contacts between the loops and the framework has proved necessary in others, and has been assisted by molecular modelling (Riechmann et al, 1988 supra; Tempest et al, 1991 supra) and systematic matching of rodent and human framework regions to minimise differences in primary sequences (Queen et al, 1989 supra; Gorman et al, 1991 supra; Maeda et al supra). Studies have shown that there are a number of residues in the 'Vernier' zone underlying the CDRs of both heavy and light chain variable domains which may adjust CDR structure and fine tune to fit the antigen and thus have a strong effect on affinity and specificity (J. Foote and G. Winter 1992 J. Mol. Biol. 224 487–499). A variation of this approach is to transfer the mouse CDRs onto a chimaeric human/mouse framework in which the buried amine acid residues are derived from the mouse antibody and the exposed amine acids are derived from homologous human frameworks (E. A. Padlan et al 1991 Mol. Immunol. 28, 485–498).

The process of CDR grafting involves the transfer of the antigen binding site from a non-human (animal) antibody to the human antibody. In most cases all three CDRs from both heavy and light chains have been transplanted from the animal antibody to a single human framework. It is expected that it should not always be necessary to transplant all the CDRs, as some CDRs may not be involved in binding to antigen, and CDRs with different sequences (and the same length) can have the same folding (and therefore contacts from antigen to the main chain contacts could be retained despite the different sequences). Indeed single domains (Ward et al, 1989, Nature 341, pp.544–546) or even single CDRs (R. Taub et al, 1989, J. Biol Chem 264, pp.259–265) can have antigen binding activities alone. However, whether all or only some of the CDRs are transplanted, the intention of CDR grafting is to transplant the same, or much the same antigen binding site, from animal to human antibodies.

Structurally, the simplest antibody (IgG) comprises four polypeptide chains, two heavy (H) chains and two light (L) chains inter-connected by disulphide bonds (see FIG. 1). The light chains exist in two distinct forms called kappa (K) and lambda ($\lambda$). Each chain has a constant region (C) and a variable region (V). Each chain is organized into a series of domains. The light chains have two domains, corresponding to the C region and the other to the V region. The heavy chains have four domains, one corresponding to the V region and three domains (1, 2 and 3) in the C region. The antibody has two arms (each arm being a Fab region), each of which has a VL and a VH region associated with each other. It is this pair of V regions (VL and VH) that differ from one antibody to another (owing to amino acid sequence variations), and which together are responsible for recognising the antigen and providing an antigen binding site (ABS). In even more detail, each V region is made up from three complementarity determining regions (CDR) separated by four framework regions (FR). The CDR's are the most variable part of the variable regions, and they perform critical antigen binding function. The CDR regions are derived from many potential germ line sequences via a complex process involving recombination, mutation and selection.

It has been shown that the function of binding antigens can be performed by fragments of a whole antibody. Example binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody, (iv) the dab fragment (Ward, E. S. et al., Nature 341, 544–546 (1989) which consists of a VH domain; (v) isolated CDR regions; and (vi) F(ab')$_2$ fragments, a bivalent fragment comprising two Fab fragments linked by a disulphide bridge at the hinge region.

Although the two domains of the Fv fragment are coded for by separate genes, it has proved possible to make a synthetic linker that enables them to be made as a single protein chain (known as single chain Fv (scFv); Bird, R. E. et al., Science 242, 423–426 (1988) Huston, J. S. et al., Proc. Natl. Acad. Sci., USA 85, 5879–5883 (1988)) by recombinant methods.

Experience with humanisation of monoclonal antibodies has shown that these molecules can be of great value in therapy and diagnosis. However, there is a requirement to be able to monitor a number of humanised antibody derivative molecules to obtain one which retains or improves on the original characteristics of the mouse monoclonals. Further there is a requirement to generate such molecules by a rapid and convenient procedure.

TERMINOLOGY

Much of the terminology discussed in this section has been mentioned in the text where appropriate.

Replicable Genetic Display Package (Rgdp)

This describes a biological particle which has genetic information providing the particle with the ability to replicate. The particle can display on its surface at least part of a polypeptide. The polypeptide can be encoded by genetic information native to the particle and/or artificially placed into the particle or an ancestor of it. The displayed polypeptide may be any member of a specific binding pair eg. heavy or light chain domains based on an immunoglobulin molecule, an enzyme or a receptor etc.

The particle may be a virus eg. a bacteriophage such as fd or M13.

Package

This describes a replicable genetic display package in which the particle is displaying a member of a specific binding pair at its surface. The package may be a bacteriophage which displays an antigen binding domain at its surface. This type of package has been called a phage antibody (pAb).

Antibody

This describes an immunoglobulin whether natural or partly or wholly synthetically produced. The term also covers any protein having a binding domain which is homologous to an immunoglobulin binding domain. These proteins can be derived from natural sources, or partly or wholly synthetically produced.

Example antibodies are the immunoglobulin isotypes and the Fab, $F(ab^1)_2$, scFv, Fv, dab, Fd fragments.

Antibody Polypeptide Dimer

An antibody polypeptide dimer is an association of two polypeptide chain components of an antibody, capable of binding an antigen. Thus, it may be one arm of an antibody consisting of a heavy chain and a light chain, it may be a Fab fragment consisting of $V_L$, $V_H$, $C_L$ and $C_H1$ antibody domains, an Fv fragment consisting of a $V_L$ domain and a $V_H$ domain, or a scFv ("single chain Fv") fragment consisting of a $V_L$ domain linked to a $V_H$ domain by a synthetic linker. An scFv fragment is a single polypeptide chain that falls within a definition of an "antibody polypeptide dimer" because it consists of two polypeptide chain components of an antibody, associated by means of the synthetic linker, and is capable of binding an antigen.

Immunoglobulin Superfamily

This describes a family of polypeptides, the members of which have at least one domain with a structure related to that of the variable or constant domain of immunoglobulin molecules. The domain contains two B-sheets and usually a conserved disulphide bond (see A. F. Williams and A. N. Barclay 1988 Ann. Rev Immunol. 6 381–405).

Example members of an immunoglobulin superfamily are CD4, platelet derived growth factor receptor (PDGFR), intercellular adhesion molecule. (ICAM). Except where the context otherwise dictates, reference to immunoglobulins and immunoglobulin homologs in this application includes members of the immunoglobulin superfamily and homologs thereof.

Homologs

This term indicates polypeptides having the same or conserved residues at a corresponding position in their primary, secondary or tertiary structure. The term also extends to two or more nucleotide sequences encoding the homologous polypeptides.

Example homologous peptides are the immunoglobulin isotypes.

Genetically diverse population

In connection with antibodies or polypeptide components thereof, this is referring not only to diversity that can exist in the natural population of cells or organisms, but also diversity that can be created by artificial mutation in vitro or in vivo.

Mutation in vitro may for example, involve random mutagenesis using oligonucleotides having random mutations of the sequence desired to be varied. In vivo mutagenesis may for example, use mutator strains of host microorganisms to harbour the DNA (see Example 38 of WO 92/01047). The words "unique population" may be used to denote a plurality of e.g. polypeptide chains, which are not genetically diverse i.e. they are all the same. A restricted population is one which is diverse but less so than the full repertoire of an animal. The diversity may have been reduced by prior selection, eg using antigen binding specificity.

Domain

A domain is a part of a protein that is folded within itself and independently of other parts of the same protein and independently of a complementary binding member.

Folded Unit

This is a specific combination of an alpha-helix and/or beta-strand and/or beta-turn structure. Domains and folded units contain structures that bring together amino acids that are not adjacent in the primary structure.

Free Form

This describes the stare of a polypeptide which is not displayed by a replicable genetic display package.

Conditionally Defective

This describes a gene which does not express a particular polypeptide under one set of conditions, but expresses it under another set of conditions. An example, is a gene containing an amber mutation expressed in non-suppressing or suppressing hosts respectively.

Alternatively, a gene may express a protein which is defective under one set of conditions, but not under another set. An example is a gene with a temperature sensitive mutation.

Suppressible Translational Stop Codon

This describes a codon which allows the translation of nucleotide sequences downstream of the codon under one set of conditions, but under another set of conditions translation ends at the codon. Example of suppressible translational stop codons are the amber, ochre and opal codons.

Mutator Strain

This is a host cell which has a genetic defect which causes DNA replicated within it to be mutated with respect to its parent DNA. Example mutator strains are NR9046mutD5 and NR9046 mut T1 (See Example 38 of WO 92/01047).

Helper Phage

This is a phage which is used to infect cells containing a defective phage genome and which functions to complement the defect. The defective phage genome can be a phagemid or a phage with some function encoding gene sequences removed. Examples of helper phages are M13KO7, M13K07 gene III no. 3; and phage displaying or encoding a binding molecule fused to a capsid protein.

Vector

This is a DNA molecule, capable of replication in a host organism, into which a gene is inserted to construct a recombinant DNA molecule.

Phage Vector

This is a vector derived by modification of a phage genome, containing an origin of replication for a bacteriophage, but not one for a plasmid.

Phagemid Vector

This is a vector derived by modification of a plasmid genome, containing an origin of replication for a bacteriophage as well as the plasmid origin of replication.

Secreted

This describes a rgdp or molecule that associates with the polypeptide displayed on the rgdp, in which the polypeptide and/or the molecule, have been folded and the package assembled externally to the cellular cytosol.

Repertoire of Rearranged Immunoglobulin Genes

A collection of naturally occurring nucleotides eg DNA sequences which encoded expressed immunoglobulin genes in an animal. The sequences are generated by the in vivo rearrangement of eg V, D and J segments for H chains and eg the V and J segments for L chains. Alternatively the sequences may be generated from a cell line immunised in vitro and in which the rearrangement in response to immunisation occurs intracellularly. The word "repertoire" is used to indicate genetic diversity.

Library

A collection of nucleotide eg DNA, sequences within clones; or a genetically diverse collection of polypeptides, or specific binding pair members, or polypeptides or sbp members displayed on rgdps capable of selection or screening to provide an individual polypeptide or sbp members or a mixed population of polypeptides or sbp members.

Repertoire of Artificially Rearranged Immunoglobulin Genes

A collection of nucleotide eg DNA, sequences derived wholly or partly from a source other than the rearranged immunoglobulin sequences from an animal. This may include for example, DNA sequences encoding VH domains by combining unrearranged V segments with D and J segments and DNA sequences encoding VL domains by combining V and J segments.

Part or all of the DNA sequences may be derived by oligonucleotide synthesis.

Secretory Leader Peptide

This is a sequence of amine acids joined to the N-terminal end of a polypeptide and which directs movement of the polypeptide out of the cytosol.

Eluant

This is a solution used to breakdown the linkage between two molecules. The linkage can be a non-covalent or covalent bond(s). The two molecules can be members of a sbp.

Derivative

This is a substance which derived from a polypeptide which is encoded by the DNA within a selected rgdp. The derivative polypeptide may differ from the encoded polypeptide by the addition, deletion, substitution or insertion of amine acids, or by the linkage of other molecules to the encoded polypeptide. These changes may be made at the nucleotide or protein level. For example the encoded polypeptide may be a Fab fragment which is then linked to an Fc tail from another source. Alternatively markers such as enzymes, floursceins etc may be linked to eg Fab, scFv fragments.

According to one aspect of the present invention there is provided a method of producing antibody polypeptide dimers specific for an antigen of interest, the method having the following steps:

(i) providing nucleic acid expression vectors which are capable of being packaged using a component of a replicable genetic display package (rgdp);

(ii) combining (a) a genetically diverse repertoire of nucleic acid sequences which each encode a first component part of an antigen-binding site of a human antibody with (b) nucleic acid which encodes a unique or genetically diverse population of a second component part of an antigen-binding site of a non-human antibody known to bind said antigen of interest, to form a library of nucleic acid sequences on said expression vectors encoding antibody polypeptide dimers, which dimers each consist of a first polypeptide chain component and a second polypeptide chain component, a first antigen-binding site component part and a second antigen-binding site component part in combination forming an antigen-binding site of an antibody polypeptide dimer;

(iii) expressing said library from said vectors in recombinant host organism cells, each of the said first polypeptide chain components being expressed as a fusion with a component of an rgdp which thereby displays said first polypeptide chain component at the surface of rgdps;

(iv) selecting from said expressed library by binding with antigen a unique or restricted population of said antibody polypeptide dimers which have binding specificity for said antigen of interest, each selected antibody polypeptide dimer being associated in its respective rgdp with nucleic acid encoding a said first component part of the antigen-binding site thereof.

Antibody polypeptide dimers are defined elsewhere in the text. The term is broad enough to encompass Fab, Fv and scFv fragments of antibodies as well as a complete arm of anantibody.

A "component part of an antibody antigen-binding site" may be or correspond to a polypeptide chain component, eg a VH or a VL domain. However, it may be a CDR, or a VL sequence plus CDR of a VH, a VH sequence plus CDR of a VL, a VH plus VL sequence lacking only a CDR, and so on. The proviso is that the first and second component parts of an antigen-binding site of an antibody must in combination (together) form an antigen-binding site. Thus, if the second component part of an antigen-binding site of a non-human antibody specific for an antigen of interest is a CDR, then the first component part of an antigen-binding site of a human antibody will comprise the remainder of a VH and VL region required to form a antigen-binding site (with or without associated antibody constant domains (in a Fab format), or with or without a linker peptide sequence (in a Fv format). (In a scFv format a linker peptide links a light chain domain to a heavy chain domain.) The second component part of an antigen-binding site of a non-human antibody may comprise a VL domain plus part of a VH domain, that part being one or more CDRs, for instance, perhaps CDR3. In such case, the first component part of an antigen-binding site of a human antibody would comprise the remainder of a VH sequence which in combination with the second component part forms an antigen-binding site. Of course, the converse situation holds and the person skilled in the art will be able to envisage other combinations of first and second component parts which together form an antigen-binding site.

There may be an additional step (v) wherein antibody polypeptide dimers selected in step (iv) are modified to remove or reduce non-human characteristics. This modification may be by genetically altering the dimers or a component thereof. This genetic alteration may be mutation, point mutation, insertion or deletion, for instance, specifically to remove or mask non-human residues, particularly those residues which might invoke an anti-idiotypic immune response upon administration of the non-human/human hybrid antibody polypeptide dimers to a human.

The modification of step (v) may comprise:

(a) combining a unique or restricted population of nucleic acid encoding said first antigen-binding site component parts selected in step (iv) with a genetically diverse repertoire of nucleic acid sequences each encoding a second component part of an antigen-binding site of human antibody, to form a second library of nucleic acid sequences encoding antibody polypeptide dimers, each antibody polypeptide dimer comprising a second antibody polypeptide chain component which is expressed from nucleic acid which is capable of being packaged using a component of an rgdp, said second chain component being expressed as a fusion with a component of an rgdp which thereby display it at the surface of rgdps, so that antibody polypeptide dimers specific for said antigen of interest, are selectable from said second library by binding with said antigen of interest. each antibody polypeptide dimer being associated in its rgdp with nucleic acid encoding a second polypeptide component thereof.

Selected antibody polypeptide dimers may be expressed as soluble polypeptides or in free form.

As explained, said second component part of an antigen-binding site of a non-human antibody may be an antibody region which makes contact with antigen, that region perhaps being a complementarity determining region (CDR).

Said second component part of an antigen-binding site of a non-human antibody may be a second polypeptide chain component of an antibody.

The sequence encoding each said second component part of non-human antibody may be genetically altered to increase its hemology to a second component part of a human antibody prior to said combination in step (ii) of the method.

Each antibody polypeptide dimer of any of said libraries of antibody polypeptide dimers may be expressed as a single polypeptide chain, which could be a scFv fragment (preferably). An scFv fragment meets the requirements of the definition of an antibody polypeptide dimer.

On the other hand, each antibody polypeptide dimer of any of said libraries of antibody polypeptide dimers may be expressed as two polypeptide chains, preferably as a Fv or a Fab fragment, but also perhaps as polypeptides with additional, non-antibody domains which will interact, either covalently or non-covalently, to hold the variable domains in a conformation which allows them to form an antigen-binding site.

According to an aspect of the present invention there is provided a method of producing human antibody polypeptide dimers specific for an antigen of interest, comprising (i) combining a diverse population of polypeptides each comprising a variable domain of a first polypeptide chain of a human antibody (population A) with a unique or restricted population of polypeptides each comprising a variable domain of a second polypeptide chain of a non-human antibody specific for said antigen (population B), thereby forming a library of antibody polypeptide dimers each consisting of a polypeptide which comprises a variable domain of a first polypeptide chain of a human antibody and a polypeptide which comprises a variable domain of a second polypeptide chain of a non-human antibody;

(ii) selecting from said library a unique or restricted population of said antibody polypeptide dimers which have binding specificity for said antigen (population C);

(iii) combining a unique or restricted population of polypeptides derived from polypeptide dimers selected in step (ii) each comprising a human first polypeptide chain (population D) with a diverse population of polypeptides each comprising a variable domain of a second polypeptide chain of a human antibody (population E), thereby forming a library of human antibody polypeptide chain dimers from which a unique or restricted population of human antibody polypeptide dimers specific for said antigen (population F) are selectable.

In a preferred embodiment of this aspect:

(a) said polypeptides of population A are each expressed from a vector (X) in recombinant host organism cells as a fusion with a component of a replicable genetic display package (rgdp) which thereby displays said polypeptide at the surface of rgdps in a first population of rgdps;

(b) nucleic acid of said vector (X) is capable of being packaged using said rgdp component, whereby the genetic material of each said rgdp encodes a said polypeptide of population A, so that the antibody polypeptide dimers of population C are each associated in their respective rgdp with nucleic acid encoding a polypeptide comprising a variable domain of a first polypeptide chain of a human antibody;

(c) each of said polypeptides of population E is expressed from a vector (Y) in recombinant host organism cells as a fusion with a component of a rgdp which thereby displays it at the surface of rgdps in a second population of rgdps; and (d) nucleic acid of said vector (Y) is capable of being packaged using said rgdp component, whereby the genetic material of each said rgdp in the second population of rgdps encodes a said polypeptide of population E.

Said population A may be expressed from the same vector as said population B, or these populations may be not expressed from the same vector. Said population D may be expressed from the same vector as said population E, or these populations D and E may be not expressed from the same vector. In other words, the method might be in a dual combinatorial format or not, perhaps being in a hierarchical format, as discussed elsewhere, amongst other possibilities.

Each antibody polypeptide dimer of any of said libraries of antibody polypeptide dimers may be expressed as a single polypeptide chain, which may be a scFv fragment.

Each antibody polypeptide dimer of any of said libraries of antibody polypeptide dimers may be expressed as two polypeptide chains, preferably a Fv or Fab fragment, as discussed already above in the context of another aspect of the present invention.

Polypeptides of said population B may be chimaeric, each comprising a human antibody constant domain (along with a non-human, eg. rodent, variable domain).

The polypeptides of said population E may each comprise a region from a non-human antibody specific for said antigen, which region is one which makes contact with antigen, such as a complementarity determining region (CDR), particularly CDR3.

Said first polypeptide chain may be antibody light chain, said second polypeptide chain being antibody heavy chain, or vice versa.

There may be an additional step of selecting said population F of human antibody polypeptide dimers specific for said antigen.

Any one of said populations C and F may be selected by binding with said antigen.

The present invention also encompasses kits comprising vectors and reagents for use in any of the methods. It further extends to libraries and antibodies or antibody fragments produced by any of the methods. Also encompassed by the present invention is a method wherein nucleic acid encoding any selected polypeptide components of an antibody polypeptide dimer, or encoding a selected antibody polypeptide dimer, is used to express said polypeptide component or polypeptide dimer or a derivative thereof in a recombinant host organism. Any polypeptide or dimer from a library produced using a method according to the present invention may be modified to produce a derivative thereof, or used to prepare a therapeutic or prophylactic medicament or a diagnostic product.

Demonstrated here are new methods of making antibodies, by utilising sequences from the antigen binding site of an antibody or population of antibodies directed against an antigen of interest. This offers another means of humanising animal antibodies with defined antigen binding activities. Thus for a single rodent antibody, sequences comprising part of the antigen binding site of the antibody may be combined with diverse repertoires of sequences of human antibodies that can in combination create a complete antigen binding site. The original rodent (and human) sequences could comprise entire chains or parts of chains. For example the light chain of a rodent antibody could be combined with a repertoire of human heavy chain variable domains; or the third CDR of the heavy chain of a rodent antibody could be combined with a repertoire of human heavy chains encoding the rest of the heavy chain variable domains and a repertoire of human light chain variable domains. The antigen binding sites comprising these sequences are then selected for binding to antigen.

The sequences comprising a component part of the antigen binding site could be a portion of primary sequence generally thought to be involved in antigen binding, for example a CDR or CDRs, or the residues at the tip of the loop of (a) CDR(s). Alternatively, the sequences could be sequences of the antibody that are known to contact the antigen, as determined for example from the structure of a complex of antigen and antibody solved by X-ray crystallography or NMR, or as determined from site directed mutagenesis of the antibody.

The antigen binding sites created by this process differ from those created by CDR grafting, in that only the portion of sequence of the original rodent antibody is likely to make contacts with antigen in a similar manner. The selected human sequences are likely to differ in sequence and make alternative contacts with the antigen from those of the original binding site. However, the constraints imposed by binding of the portion of original sequence to antigen and the shapes of the antigen and its antigen binding sites, are likely to drive the new contacts of the human sequences to the same region or epitope of the antigen. We have therefore termed the process "epitope imprinted selection" (EIS).

Starting with an animal antibody, one process results in the selection of antibodies that are partly human antibodies. Such antibodies may be sufficiently similar in sequence to human antibodies to be used directly in therapy or after alteration of a few key residues. For example, antibodies created with human heavy and light chain variable domains that also comprise the VH-CDR3 region from a rodent antibody will closely resemble genuine human antibodies as the CDR3 region of both human and rodent antibodies is highly variable. Likewise the light chains of some rodent antibodies are very similar in sequence to the light chains of human anitbodies. Thus antibodies created from these rodent light chains in combination with a repertoire of human heavy chains may closely resemble human antibodies. Sequence differences between the rodent component of the selected antibody with human sequences could be minimised by replacing those residues that differ with the residues of human sequences, for example, by site directed mutagenesis of individual residues, or by CDR grafting of entire loops. Instead of starting with an animal antibody, it should also be possible to start with an genetically engineered antibody derived from an animal antibody. The starting engineered antibody might for example be a CDR grafted antibody with human framework regions and mouse complementarity regions (as described in GB2188638B, for instance). Alternatively the starting engineered antibody could comprise heavy or light chains in which residues had been altered to maximise sequence homology with human antibodies.

However, the invention may also be used to create antibodies with entirely human sequences. For example, starting with a partly human antibody with human heavy chain non-human, e.g. mouse, light chain, the non-human light chain could be replaced by repertoires of human light chains. In this way, the sequences of the selected antibodies will be entirely human and yet the antigen binding site should be directed towards the same epitope of the antigen. EIS therefore offers a method for making partly human or entirely human antibodies that bind to the same epitope as animal or partly human antibodies respectively.

In CDR grafting the entire antigen binding site is transplanted, and it is usually necessary to test only one or a few antibodies for binding to antigen. However, EIS may use only part of the antigen binding site in combination with a, perhaps very large, repertoire of human sequences, when there is a requirement for the screening of a much larger number of antibodies. Indeed in a preferred embodiment, repertoires of antibody fragments are displayed on the surface of filamentous phase and the genes encoding fragments with antigen binding activities are selected by binding of the phase to antigen. It was disclosed in patent application WO 92/01047 that antibody fragments can be displayed on phase and that they will bind antigen and that they can be selected. The ability to select antibodies provided by the use of display on phase as described in WO 92/01047 allows the rapid screening of large numbers of humanised antibody derivatives which can be generated using insertion of CDRs at restriction sites or in vitro mutagenesis techniques (Riechmann et al, 1988 supra; Patent GB2188638B) or using PCR technology (B. L. Daugherty et al 1991 Nucl. Acids Res. 19, pp2471–2476). In the application WO 92/01047, the generation of hierarchical libraries was described in which one antibody heavy or light chain variable domain was kept constant and displayed on phase with a library of the complementary chain variable domain for the selection of partners that bind to antigen. Such an approach generates a highly diverse pool of heavy and light chain variable domain combinations from which antibody specificities can be selected. Chain shuffling has been applied, for example, to obtaining further light chain and heavy chain partners for the complementary chain of a hapten binding antibody (Clackson et al, 1991, Nature, 352, 624–628) and to build high affinity human antibodies (J. D. Marks et al, 1992 Bio/Technology 10, 779–783). In these cases, the new partner chains were highly related in sequence to those chains seen in the original combination.

In these examples, chains of different species were not combined. However, there is a report of an attempt to shuffle the heavy chains of a mouse antibody directed against a hapten with a repertoire of human light chains (and also with a repertoire of mouse light chains), and screening for binding of individual clones to antigen using nitrocellulose filters. However, no binders were detected, nor was the process proposed as a means to "humanise" mouse antibodies (A. S. Kang et al, Proc. Natl. Acad. Sci. USA 1991, 88, 11120–11123). The authors concluded that the "redesign of antibodies through recombination of a somatically mutated chain with a naive partner may be a difficult process". The use of EIS (as illustrated by chain shuffling using chains from different species) therefore appears to be a novel concept. Furthermore, in view of the example from Kang et al, 1991 supra, it is surprising that antigen binding combinations can be produced by combining the chains from a mouse antibody with repertoires of chains from unimmunised human sources (as described in Example 1 below).

There are a wide range of formats for use of methods according to the present invention. For example:

(1) the use of Fv, single chain Fv and Fab fragments is favoured for expression in bacteria or display on filamentous phage (for Fab fragments see Examples 1 and 2; for scFv see Examples 3 and 4). Most preferably, the antibody fragments are displayed on filamentous phage, and the phages selected directly to binding to antigen. The antibodies selected by these procedures may be used directly, or fused with further coding sequences, for example with human constant regions to generate antibody molecules with human effector functions. The variable domains could also be fused to sequences encoding an enzyme or a toxin molecule to allow antibody directed targeting of drugs or toxins to particular cell types.

(2) The repertoires of human chains may be readily provided from any of several possible repertoires of V-genes, for example from the rearranged V-genes of unimmunised humans (Marks et al, 1991, J. Mol. Biol., 222, pp581–597; and Example 1), or from immunised humans, or from synthetic V-gene repertoires. For instance, libraries of human germ line heavy and light chain V-genes may be generated with synthetic CDR3 regions incorporating human J regions and antibody specificities isolated (Hoogenboom and Winter, 1992, J. Mol Biol., 227, pp381–388). Furthermore, it may be possible to use repertoires of human V-genes (for example made synthetically) which are closely related in sequence (perhaps the most homologous) to each of the chains of a mouse antibody. (See Example 5).

(3) The heavy and light chains of the original antibody may be provided by their encoding V-genes (isolated for example by PCR, Orlandi et al., 1989) (Examples 1, 2 and 3) However, it is also possible to start with a repertoire of mouse chains, preferably raised by immunisation (Example 4). For example, a repertoire of mouse heavy chains could be combined with mouse light chains and selected for binding (as in Clackson et al., 1991 supra): the selected repertoires of paired chains could then be recombined with repertoires of complementary human chains to force new pairings. Alternatively, the repertoire of mouse chains from the mRNA of an immunised mouse could simply be combined with a repertoire of complementary human chains.

(4) It is possible to use entire heavy and light chain variable domains, as in "chain shuffling" methods or component parts of the chains, for example as in Marks et al, 1992 supra, by retaining the light chain and CDR3 of the heavy chain of an antibody (and shuffling this sequence with a repertoire of chains comprising the remainder of the heavy chain variable domain CDRs 1 and 2). One embodiment of the present invention, illustrated by examples 2 and 3, involves retaining at least one region from the original parent non-human antibody, which region contacts antigen, when shuffling with human chains, or component parts of human antibody antigen-binding site. This region may be a CDR, in which case the procedure is "CDR-imprinted selection".

Indeed, in examples 2 and 3, the CDR3 of the original mouse heavy chain was retained, and combined with a repertoire of human heavy chain variable domains by PCR amplification of a repertoire of human heavy chain variable domains with a primer incorporating the mouse CDR3. The retention of mouse VH-CDR3 may be particularly advantageous in that CDR3 of the heavy chain is often most important for antigen binding.

This principle could be extended to a mouse CDR3 repertoire by amplifying the rearranged mouse VH genes with human JH primers (forward primers) and human VH framework 3 primers (backward primers). These primers would have to be designed with homology to both mouse and human V-genes. The amplified DNA repertoire of mouse CDR3s could then be assembled by PCR with a repertoire of human heavy chain genes.

(5) The chain shuffling could be performed using two replicons, for example using a dual combinatorial procedure as described in Hoogenboom et al, 1991 Nucleic Acids Research, 19, pp4133–4137, in which the chain which is to be kept constant is cloned in one replicon, for instance a phage, and then combined with a repertoire of chains in another replicon, for instance a plasmid, as illustrated in Example 1. Alternative methods enabling both chains to be cloned on the same replicon with high efficiency have also been devised. These again rely on cloning heavy and light chain genes on separate replicons, but this time with the aim of promoting recombination between two vectors so that both chains are placed on the same replicon. An example system is based on the lox P/Cre recombinase system of coliphage P1 (Hoess and Abremski, 1990, in "Nucleic acids and Molecular Biology", Eckstein and Lilley, eds. Vol 4, pp99–109, Springer-Verlag, Berlin, Heidelberg). For the dual combinatorial procedure the antibody may be expressed as a Fv fragment or as a Fab fragment (as in Example 1). In the case of a Fab fragment, the VH1CH1 portion of the heavy chain is expressed on one replicon, eg. phage, and the light chain on the other, eg. plasmid. The V domains of the Fab fragment to be used in the shuffling procedures as a source of new specificities may optionally be fused to cloned human domains eg. Cγ1 and Ck domains. (The V-domains can also be fused directly to the CH1, Ck or Cλ domains by amplifying directly from the human antibody mRNA repertoire.)

Alternatively, the chain shuffling can be performed in a single replicon using a PCR assembly process as in Clackson et al, 1991, supra, or by sequential cloning of libraries of restriction fragments at appropriate sites which have been incorporated into the original constructs, for instance into the linker region of a single chain Fv.

The present invention encompasses the replacement of both chains by two shuffle steps and in one embodiment to the development of a human antibody with similar or improved characteristics to a non-human, eg. rodent, antibody. In this embodiment, the parent eg rodent antibody would be made into a "phage antibody". A phage antibody (pAb) is defined as a bacteriophage virus particle which displays at its surface an antibody, an antibody derivative or fragment, such as Fab, Fv, scFv etc, or a domain homologous to an immunoglobulin domain: see WO 92/01047. One chain would be replaced with a repertoire of chains derived from a human immunoglobulin repertoire, for example from an adult lymphocyte population or from fetal or artificially derived sources. This mixed population of phage can be selected by binding to antigen to derive a population of phage antibodies that bind to the original antigen but now consists of one (eg) rodent and one human antibody chain. The remaining rodent chain can be replaced by a repertoire of similar chains derived from a human repertoire, either the same or a different source as was used in the initial shuffle. After selection a population of antibodies is obtained which still binds antigen, a population consisting of antibodies containing two human antibody chains. Thus the original rodent antibody has been converted into a human antibody that binds the same antigen.

The generation of a large number of humanised antibodies by methods according to the present invention may have advantages beyond allowing selection of antibodies of desired affinity and specificity. When humanised antibodies are used in humans in therapy it is possible that there may be an anti-idiotype response. The antibodies isolated may be surveyed for anti-idiotype response when administered in vivo and those with the lowest response selected. Alternatively, one antibody may be administered therapeutically until an anti-idiotype response is detected at which time the antibody used is switched to a second, equally effective antibody with a different idiotype.

Humanised antibodies which may be obtained using the present invention are likely to be better than conventional CDR-grafted humanised antibodies, in the sense that they will be less likely to invoke an anti-idiotypic response.

The antibodies selected by the procedures of the present invention may be used directly in the single chain Fv or Fab format. Alternatively, the variable domains may be fused with further coding sequences, for example with human constant regions to generate antibody molecules with, for example, human effector functions. The variable domains could be fused to sequences encoding an enzyme or a toxin molecule to allow antibody directed targeting of drugs or toxins to particular cell types (although if these molecules are not of human origin some of the advantages of humanising are lost).

Although the isolation of antibodies by selection for binding to antigen may be performed using phage display at each stage, where chain shuffling is performed by PCR assembly or insertion of restriction fragments, particularly when the numbers have been reduced the antibodies may be screened for antigen binding using a filter assay (A. Skerra et al 1991 Anal Biochem 196 151–155; M. L. Dreher et al 1991 J. Immunol Methods 139 197–205; PCT/GB90/01476). These procedures will be effective with a relatively small number of clones compared with the number which can be handled using phage display.

Aspects and embodiments of the present invention will now be explained further by means of the following examples. These are intended to illustrate the invention without limitation. In addition to the documents mentioned throughout the text, attention is drawn to WO 92/01047 wherein many of the materials and methods used here were described. The disclosure of WO 92/01047 is herein incorporated by reference. Readers of the present document are urged to consult WO 92/01047 for further details and explanation of functional display of antibodies and antibody fragments, including antibody polypeptide dimers, on the surface of rgdps.

Throughout the text there are references to figures, wherein:

FIG. 2 shows the polylinker region of vector pUC19-pelB-myc. (SEQ.ID NO: 126)

FIG. 5 shows nucleotide and deduced amino-acid sequences of the V-genes of Mab32. The CDR-regions are in bold. (Heavy chain nucleotides SEQ ID NO:2; Light chain amino acids SEQ ID NO:3.; Light chain nucleotides SEQ ID NO:4).

FIG. 6 shows the deduced protein sequences of $V_H$ and $V_L$ antibody genes of antibody fragments binding to human TNF.

(Light chains: Mab32 SEQ ID NO:110; Vλ1-1-1 SEQ ID NO:111; VλAZ SEQ ID NO:112; VλC4 SEQ ID NO:113; VλD1SEQ ID NO:114. Heavy chains: Mab32 SEQ ID NO:115; DP-51 SEQ ID NO:116; VHP1SEQ ID NO:117; VHP2 SEQ ID NO:133; VHP3 SEQ ID NO:134; DP-46 SEQ ID NO:118; VHLM2 SEQ ID NO:135; VHLM8 SEQ ID NO:141).

Figure 7:
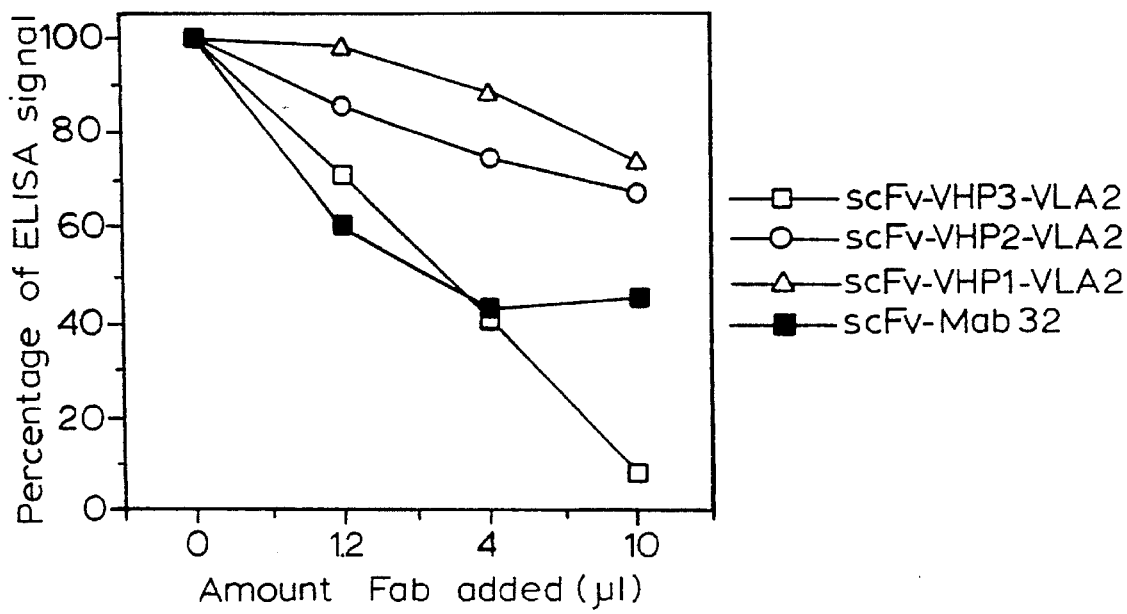

FIG. 7 shows the results of a competition ELISA between FabMab32 and single chain Fv fragments.

Figure 8:
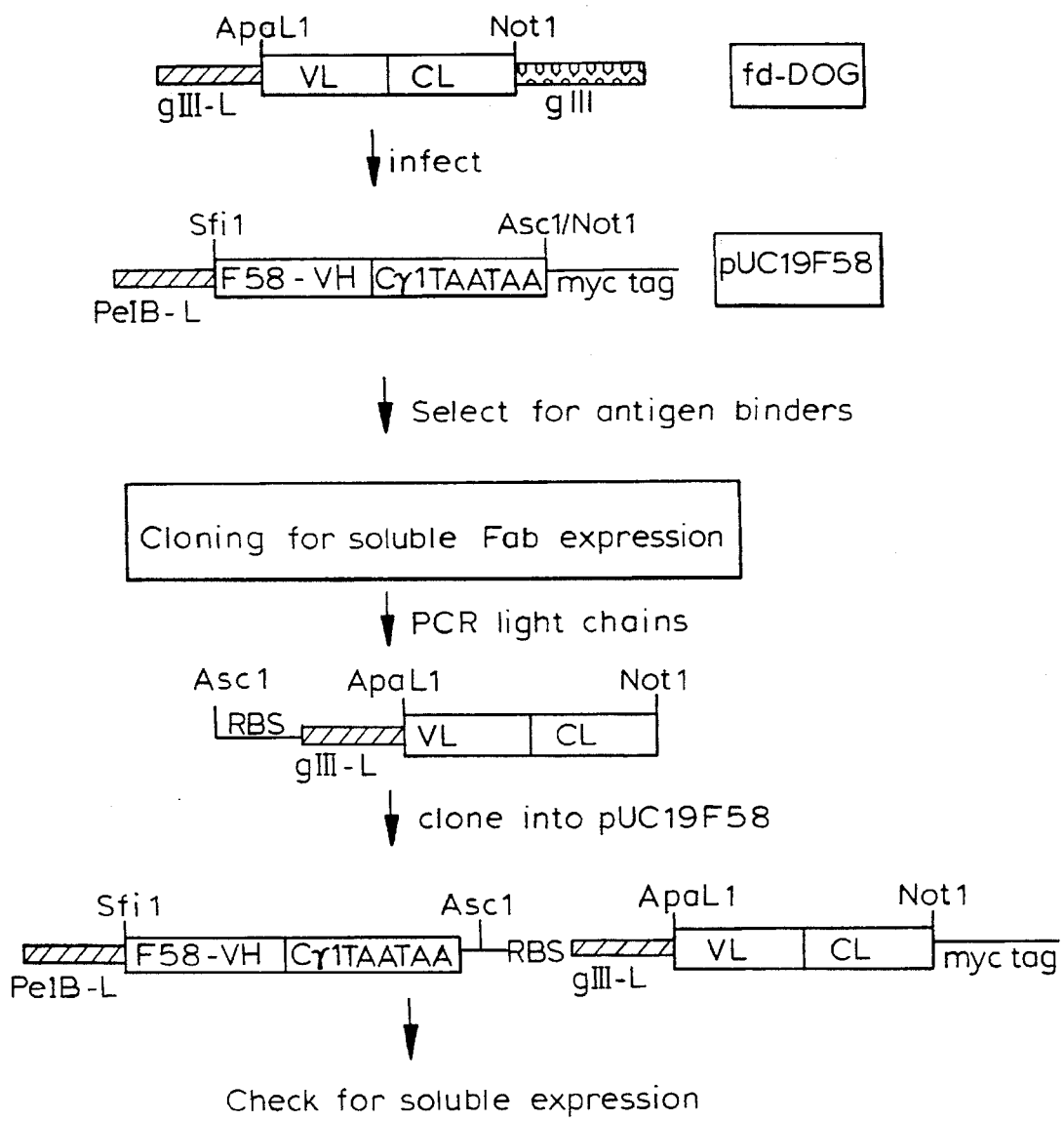
Figure 8B:
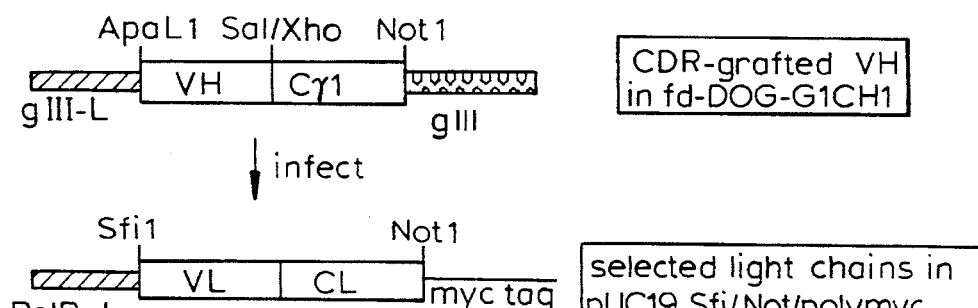

FIGS. 8(i) and 8(ii) show an example of a scheme for humanising a mouse antibody using CDR imprinted selection using a dual combinatorial method.

FIG. 9 shows an example of a scheme for humanising a mouse antibody using CDR imprinted selection using combinatorial libraries in a single replicon, single chain Fv format.

Figure 10:
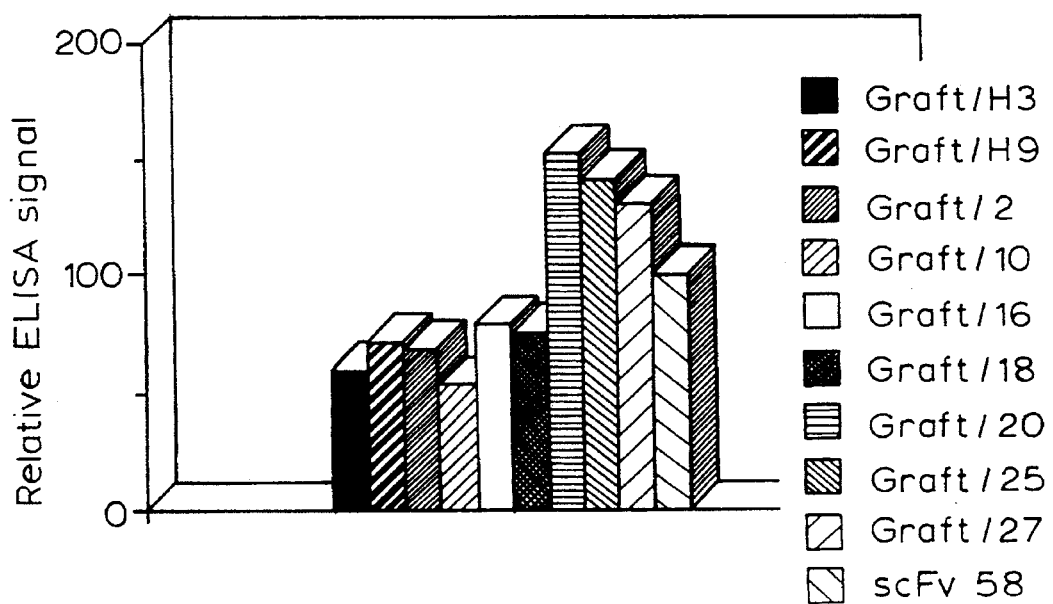

FIG. 10 shows relative ELISA signals obtained with scFv fragments selected by CDR imprinted selection compared to the original F58 single chain Fv fragment.

FIG. 11 shows the deduced amino acid sequences of the selected heavy chains Graft/27, Graft/2, Graft/H3 and Graft/H9 in comparison to the original F58 heavy chain and to the most closely related human germ line VH genes. (VH6:F58 SEQ ID NO:127; DP-74 SEQ ID NO:128; Graft/27 SEQ ID NO:136; Graft/2 SEQ ID NO:137; GRAFT/H3 SEQ ID NO:138; GRAFT/H9 SEQ ID NO:139. VH1: F58 SEQ ID NO:129, DP-2 SEQ ID NO:130; Graft/20 SEQ ID NO:140).

Figure 12:
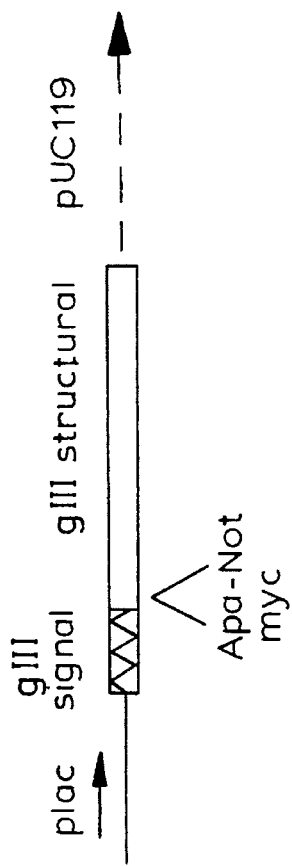

FIG. 12 shows the vector pCANTAB3-myc and the DNA and amino acid sequences in the region of the cloning site. (SEQ ID NO:131).

FIG. 13 shows the vector pCANTAB5-myc and the DNA and amino acid sequence in the region of the cloning site. (SEQ ID NO:132).

Figure 14:
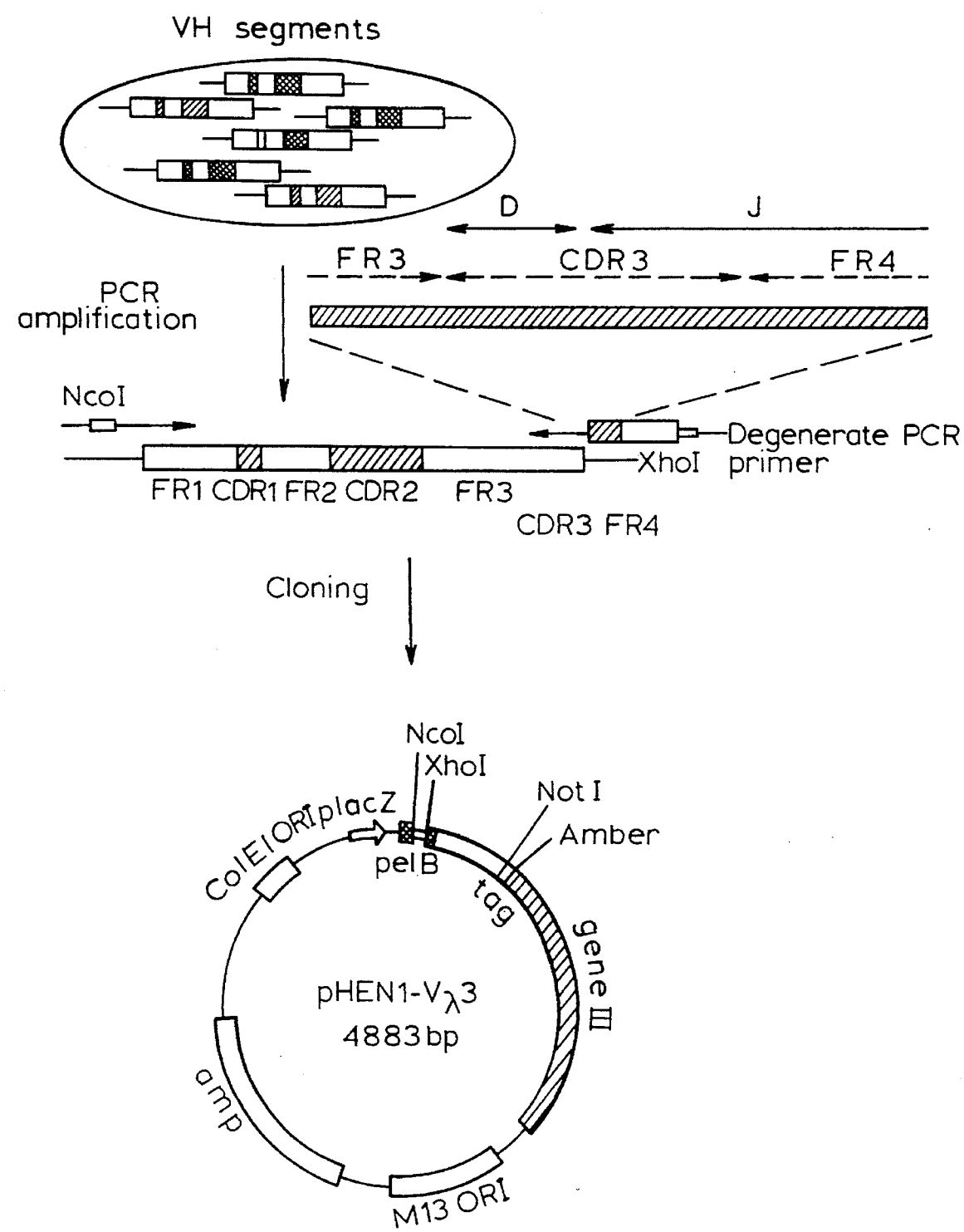

FIG. 14 shows the assembly of rearranged VH genes.

Table 1 lists oligonucleotide primers and peptides mentioned in the text. The attention of readers of this document is directed to table 1 for sequence information on these oligonucleotides and peptides, complete with the SEQ ID NO of sequences in the listing.

TABLE 1

Oligonucleotides Used

| PRIMER | | SEQUENCE |
|---|---|---|
| SEQ ID NO: 5 | MOJK1FORNX | 5'-CCG TTT GAT TTC CAG CTT GGT GCC-3' |
| SEQ ID NO: 6 | MVKBASFI | 5'-CAT GAC CAC GCG GCC CAG CCG GCC ATG GCC GAC ATT GAG CTC ACC CAG TCT CCA-3' |
| SEQ ID NO: 7 | MOVK-HUCK-BACK | 5'-GGC ACC AAG CTG GAA ATC AAA CGG ACT GTG GCT GCA CCA TCT GTC TTC-3' |
| SEQ ID NO: 8 | HUCKNOT16NOMYC | 5'-GAG TCA TTC TCG ACT TGC GGC CGC TTA TTA ACA CTC TCC CCT GTT GAA GCT CTT-3' |
| SEQ ID NO: 9 | VH1FOR-2 | 5'-TGA GGA GAC GGT GAC CGT GGT CCC TTG GCC CC-3' |
| SEQ ID NO: 10 | Mo-VH-Hu-CH1 | 5'-GGG ACC ACG GTC ACC GTC TCC TCA GGA AGT GCA TCC GCC CCA ACC CTT TTC-3' |
| SEQ ID NO: 11 | HCM1FONO | 5'-CCA CGA TTC TGC GGC CGC CAC TGG AAG AGG CAC GTT CTT TTC TTT-3' |
| SEQ ID NO: 12 | HUCKCYSNOT | 5'-GAG TCA TTC TCG ACT TGC GGC CGC ACA CTC TCC CCT GTT GAA GCT CTT-3' |
| SEQ ID NO: 12 | HUCLCYSNOT | 5'-GAG TCA TTC TCG ACT TGC GGC CGC TGA ACA TTC TGT AGG GGC CAC TGT CTT-3' |
| SEQ ID NO: 14 | MVKBAAPA | 5'-CAC AGT GCA CTC GAC ATT GAG CTC ACC CAG TCT CCA-3' |
| SEQ ID NO: 107 | VH1BACKAPA | 5'-CAT GAC CAC AGT GCA CAG GTS MAR CTG CAG SAG TCW GG-3' |
| SEQ ID NO: 15 | HCM1FONO | 5'-CCA CGA TTC TGC GGC CGC CAC TGG AAG AGG CAC GTT CTT TTC TTT-3' |
| SEQ ID NO: 16 | HCM1FO | 5'-TGG AAG AGG CAC GTT CTT TTC TTT-3' |
| SEQ ID NO: 17 | HUCLCYS | 5'-TGA ACA TTC TGT AGG GGC CAC TGT CTT-3' |
| SEQ ID NO: 18 | HUCKCYS | 5'-ACA CTC TCC CCT GTT GAA GCT CTT-3' |
| SEQ ID NO: 19 | fd-PCR-BACK | 5'-GCG ATG GTT GTT GTC ATT GTC GGC-3' |
| SEQ ID NO: 20 | fd-SEQ1 | 5'-GAA TTT TCT GTA TGA GG-3' |
| SEQ ID NO: 21 | HULAMBDASEQ | 5'-GTG TGG CCT TGT TGG CTT G-3' |
| SEQ ID NO: 22 | pHEN-SEQ | 5'-CTA TGC GGC CCC ATT CA-3' |
| SEQ ID NO: 23 | LINKSEQ | 5'-CGA TCC GCC ACC GCC AGA G-3' |
| SEQ ID NO: 24 | Hu-MCH1FORSEQ2 | 5'-AGG AAG TCC TGT GCG AGG CAG-3' |
| SEQ ID NO: 25 | HuVL1BACKSFI | 5'-GTC CTC GCA ACT CGC GCC CAG CCG GCC ATG GCC CAG TCT GTG TTG ACG CAG CCG CC-3' |
| SEQ ID NO: 26 | HuCL1FORAMBNOT | 5'-CCA CGA TTC TGC GGC CGC CTA TGA ACA TTC TGT AGG GGT CAC TGT-3' |
| SEQ ID NO: 108 | VH1BACKSFI15 | 5'-CAT GCC ATG ACT CGC GGC CCA GCC GGC CAT GGC CSA GGT SMA RCT GCA GSA GTC (A/T)GG |
| SEQ ID NO: 27 | HuJH4FORASSXHoI | 5'-GCCTGAACCGCC TCCACCTCTCGAGAA CGGTGACCAGGG-3' |
| SEQ ID NO: 28 | HuVBLBACK-XhoI | 5'-CTGGTCACCGTC TCGAGAGGTGGA GGC-3' |
| SEQ ID NO: 29 | HuJH4FORSalI | 5'-GGAGGATGCACT TGTCGACACGGT GACCAG-3' |

Human VH Back Primers

| SEQ ID NO: 30 | HuVH1aBACK | 5'-CAG GTG CAG CTG GTG CAG TCT GG-3' |
| SEQ ID NO: 31 | HuVH2aBACK | 5'-CAG GTC AAC TTA AGG GAG TCT GG-3' |
| SEQ ID NO: 32 | HuVH3aBACK | 5'-GAG GTG CAG CTG GTG GAG TCT GG-3' |
| SEQ ID NO: 33 | HuVH4aBACK | 5'-CAG GTG CAG CTG CAG GAG TCG GG-3' |
| SEQ ID NO: 34 | HuVH5aBACK | 5'-GAG GTG CAG CTG TTG CAG TCT GC-3' |
| SEQ ID NO: 35 | HuVH6aBACK | 5'-CAG TGA CAG CTG CAG CAG TCA GG-3' |

Human IgM Constant Region Primer

| SEQ ID NO: 36 | HuIgMFOR | 5'-TGG AAG AGG CAC GTT CTT TTC TTT-3' |

Human κ Constant Region Primer

| SEQ ID NO: 37 | HUCκFOR | 5'-AGA CTC TCC CCT GTT GAA GCT CTT-3' |

Human λ Constant Region Primer

| SEQ ID NO: 38 | HUCλFOR | 5'-TGA AGA TTC TGT AGG GGC CAC TGT CTT-3' |

Human JH Forward Primers

| SEQ ID NO: 39 | HuJH1-2FOR | 5'-TGA GGA GAC GGT GAC CAG GGT GCC-3' |
| SEQ ID NO: 40 | HuJH3FOR | 5'-TGA AGA GAC GGT GAC CAT TGT CCC-3' |
| SEQ ID NO: 41 | HuJH4-5FOR | 5'-TGA GGA GAC GGT GAC CAG GGT TCC-3' |
| SEQ ID NO: 42 | HuJH6FOR | 5'-TGA GGA GAC GGT GAC CGT GGT CCC-3' |

VH BACK PRIMERS WITH APA LI SITES

| SEQ ID NO: 43 | HUVH1BAAPA | 5'-CAT GAC CAC AGT GCA CAG GTG CAG CTG GTG CAG TCT GG-3' |
| SEQ ID NO: 44 | HUVH2BAAPA | 5'-CAT GAC CAC AGT GCA CAG GTC AAC TTA AGG GAG TCT GG-3' |
| SEQ ID NO: 45 | HUVH3BAAPA | 5'-CAT GAC CAC AGT GCA CAG GTG CAG CTG GTG GAG TCT GG-3' |
| SEQ ID NO: 46 | HUVH4BAAPA | 5'-CAT GAC CAC AGT GCA CAG GTG CAG |

TABLE 1-continued

Oligonucleotides Used

| PRIMER | | SEQUENCE |
|---|---|---|
| SEQ ID NO: 47 | HUVH5BAAPA | 5'-CAT GAC CAC AGT GCA CAG GTG CAG CTG TTG CAG TCT GC-3' |
| SEQ ID NO: 48 | HUVH6BAAPA | 5'-CAT GAC CAC AGT GCA CAG GTA CAG CTG CAG CAG TCA GG-3' |

JHSAL primers

| SEQ ID NO: 49 | HUJH1–2FORSAL | 5'-GAG TCA TTC TCG TGT CGA CAC GGT GAC CAG GGT GCC-3' |
| SEQ ID NO: 50 | HUJH3FORSAL | 5'-GAG TCA TTC TCG TGT CGA CAC GGT GAC CAT TGT CCC-3' |
| SEQ ID NO: 51 | HUJH4–5FORSAL | 5'-GAG TCA TTC TCG TGT CGA CAC GGT GAC CAG GGT TCC-3' |
| SEQ ID NO: 52 | HUJH6FORSAL | 5'-GAG TCA TTC TCG TGT CGA CAC GGT GAC CGT GGT CCC-3' |

LAMBDA BACK PRIMERS WITH SFI SITES

| SEQ ID NO: 53 | HUVL1BASFI: | 5'-GTC CTC GCA ACT GCG GCC CAG CCG GCC ATG GCC CAG TCT GTG TTG ACG CAG CCG CC-3' |
| SEQ ID NO: 54 | HUVL2BASFI: | 5'-GTC CTC GCA ACT GCG GCC CAG CCG GCC ATG GCC CAG TCT GCC CTG ACT CAG CCT GC-3' |
| SEQ ID NO: 55 | HUVL3aBASFI: | 5'-GTC CTC GCA ACT GCG GCC CAG CCG GCC ATG GCC TCC TAT GTG CTG ACT CAG CCA CC-3' |
| SEQ ID NO: 56 | HUVL3bBASFI: | 5'-GTC CTC GCA ACT GCG GCC CAG CCG GCC ATG GCC TCT TCT GAG CTG ACT CAG GAC CC-3' |
| SEQ ID NO: 57 | HUVL4BASFI: | 5'-GTC CTC GCA ACT GCG GCC CAG CCG GCC ATG GCC CAG GTT ATA CTG ACT CAA CCG CC-3' |
| SEQ ID NO: 58 | HUVL5BASFI: | 5'-GTC CTC GCA ACT GCG GCC CAG CCG GCC ATG GCC CAG GCT GTG CTC ACT CAG CCG TC-3' |
| SEQ ID NO: 59 | HUVL6BASFI: | 5'-GTC CTC GCA ACT GCG GCC CAG CCG GCC ATG GCC AAT TTT ATG CTG ACT CAG CCC CA-3' |

KAPPA BACK PRIMERS WITH SFI SITES

| SEQ ID NO: 60 | HUVK1BASFI: | 5'-GTC CTC GCA ACT GCG GCC CAG CCG GCC ATG GCC GAC ATC CAG ATG ACC CAG TCT CC-3' |
| SEQ ID NO: 61 | HUVK2BASFI: | 5'-GTC CTC GCA ACT GCG GCC CAG CCG GCC ATG GCC GAT GTT GTG ATG ACT CAG TCT CC-3' |
| SEQ ID NO: 62 | HUVK3BASFI: | 5'-GTC CTC GCA ACT GCG GCC CAG CCG GCC ATG GCC GAA ATT GTG TTG ACG CAG TCT CC-3' |
| SEQ ID NO: 63 | HUVK4BASFI: | 5'-GTC CTC GCA ACT GCG GCC CAG CCG GCC ATG GCC GAC ATC GTG ATG ACC CAG TCT CC-3' |
| SEQ ID NO: 64 | HUVK5BASFI: | 5'-GTC CTC GCA ACT GCG GCC CAG CCG GCC ATG GCC GAA ACG ACA CTC ACG CAG TCT CC-3' |
| SEQ ID NO: 65 | HUVK6BASFI: | 5'-GTC CTC GCA ACT GCG GCC CAG CCG GCC ATG GCC GAA ATT GTG CTG ACT CAG TCT CC-3' |
| SEQ ID NO: 66 | HUCLFORSERASCNOT | 5'-GAG TCA TTC TCG ACT TGC GGC CGC CTG CTA TTA TCG GGC GCG CCT TTA TTA TGA AGA TTC TGT AGG GGC CAC TGT CTT-3' |
| SEQ ID NO: 67 | HUCKFORSERASCNOT | 5'-GAG TCA TTC TCG ACT TGC GGC CGC CTG CTA TTA TCG GGC GCG CCT TTA TTA AGA CTC TCC CCT GTT GAA GCT CTT-3' |
| SEQ ID NO: 68 | HUCKFORSER | 5'-AGA CTC TCC CCT TTT GAA GCT CTT-3' |
| SEQ ID NO: 69 | HUCLFORSER | 5'-TGA AGA TTC TGT AGG GGC CAC TGT CTT-3' |
| SEQ ID NO: 70 | HUCKFORSERNOT | 5'-GAG TCA TTC TCG ACT TGC GGC CGC AGA CTC TCC CCT GTT GAA GCT CTT-3' |
| SEQ ID NO: 71 | HUCLFORSERNOT | 5'-GAG TCA TTC TCG ACT TGC GGC CGC TGA AGA TTC TGT AGG GGC CAC TGT CTT-3' |

Human Vκ Back Primers

| SEQ ID NO: 72 | HuVk1aBACK | 5'-GAC ATC CAG ATG ACC CAG TCT CC-3' |
| SEQ ID NO: 73 | HuVk2aBACK | 5'-GAT GTT GTG ATG ACT CAG TCT CC-3' |
| SEQ ID NO: 74 | HuVk3aBACK | 5'-GAA ATT GTG TTG ACG CAG TCT CC-3' |
| SEQ ID NO: 75 | HuVK4aBACK | 5'-GAC ATC GTG ATG ACC CAG TCT CC-3' |
| SEQ ID NO: 76 | HuVk5aBACK | 5'-GAA ACG ACA CTC ACG CAG TCT CC-3' |
| SEQ ID NO: 77 | HuVk6aBACK | 5'-GAA ATT GTG CTG ACT CAG TCT CC-3' |

Human λ Back Primers

| SEQ ID NO: 78 | Huλ1BACK | 5'-CAG TCT GTG TTG ACG CAG CCG CC-3' |
| SEQ ID NO: 79 | HuλBACK | 5'-CAG TCT GCC CTG ACT CAG CCT GC-3' |
| SEQ ID NO: 80 | Huλ3aBACK | 5'-TCC TAT GTG CTG ACT CAG CCA CC-3' |
| SEQ ID NO: 81 | Huλ3bBACK | 5'-TCT TCT GAG CTG ACT CAG GAC CC-3' |
| SEQ ID NO: 82 | Huλ4BACK | 5'-CAC GTT ATA CTG ACT CAA CCG CC-3' |
| SEQ ID NO: 83 | Huλ5BACK | 5'-CAG GCT GTG CTC ACT CAG CCG TC-3' |
| SEQ ID | Huλ6BACK | 5'-AAT TTT ATG CTG |

TABLE 1-continued

Oligonucleotides Used

| PRIMER | | SEQUENCE |
|---|---|---|
| SEQ ID NO: 84 | | ACT CAG CCC CA-3' |
| SEQ ID NO: 85 | G3LASCGTGBACK | 5'-GTC CTC GCA ACT GGC GCG CCA CAA TTT CAC AGT AAG GAG GTT AAA CTT GTG AAA AAA TTA TTA TTC GCA ATT-3' |
| SEQ ID NO: 86 | F58GRAFTJH4SAL | 5'-GGA TGC ACT TGT CGA CAC GGT GAC CAG GGT ACC TTG GCC CCA GTA GTC AAA GTA GTC CTC TTC GTA ATC ATA GTA GAT CAG GTC ACA GTA ATA CAC GGC CGT GTC-3' |
| SEQ ID NO: 87 | F58GRAFTSAL | 5'-GGA TGC ACT TGT CGA CAC GGT GAC CAG GGT ACC TTG GCC CCA GTA GTC AAA GTA GTC CTC TTC GTA ATC ATA GTA GAT CAG GTC ACA GTA ATA CAC GGC CGT GTC-3' |

LAMBDA BACK PRIMERS WITH APA LI SITES

| SEQ ID NO: 88 | HUVL1BAAPA: | 5'-TGA GCA CAC AGT GCA CTC CAG TCT GTG TTG ACG CAG CCG CC-3' |
| SEQ ID NO: 89 | HUVL2BAAPA: | 5'-TGA GCA CAC AGT GCA CTC CAG TCT GCC CTG ACT CAG CCT GC-3' |
| SEQ ID NO: 90 | HUVL3aBAAPA: | 5'-TGA GCA CAC AGT GCA CTC TCC TAT GTG CTG ACT CAG CCA CC-3' |
| SEQ ID NO: 91 | HUVL3bBAAPA: | 5'-TGA GCA CAC AGT GCA CTC TCT TCT GAG CTG ACT CAG GAC CC-3' |
| SEQ ID NO: 92 | HUVL4BAAPA: | 5'-TGA GCA CAC AGT GCA CTC CAG GTT ATA CTG ACT CAA CCG CC-3' |
| SEQ ID NO: 93 | HUVL5BAAPA: | 5'-TGA GCA CAC AGT GCA CTC CAG GCT GTG CTC ACT CAG CCG TC-3' |
| SEQ ID NO: 94 | HUVL6BAAPA: | 5'-TGA GCA CAC AGT GCA CTC AAT TTT ATG CTG ACT CAG CCC CA-3' |

KAPPA BACK PRIMERS WITH APA LI SITES

| SEQ ID NO: 95 | HUVK1BAAPA: | 5'-TGA GCA CAC AGT GCA CTC GAC ATC CAG ATG ACC CAG TCT CC-3' |
| SEQ ID NO: 96 | HUVK2BAAPA: | 5'-TGA GCA CAC AGT GCA CTC GAT GTT GTG ATG ACT CAG TCT CC-3' |
| SEQ ID NO: 97 | HUVK3BAAPA: | 5'-TGA GCA CAC AGT GCA CTC GAA ATT GTG TTG ACG CAG TCT CC-3' |
| SEQ ID NO: 98 | HUVK4BAAPA: | 5'-TGA GCA CAC AGT GCA CTC GAC ATC GTG ATG ACC CAG TCT CC-3' |
| SEQ ID NO: 99 | HUVK5BAAPA: | 5'-TGA GCA CAC AGT GCA CTC GAA ACG ACA CTC ACG CAG TCT CC-3' |
| SEQ ID NO: 100 | HUVK6BAAPA: | 5'-TGA GCA CAC AGT GCA CTC GAA ATT GTG CTG ACT CAG TCT CC-3' |

Human VH Back Primers

| SEQ ID NO: 101 | HuVH1aBACKSfi | 5'-GTC CTC GCA ACT GCG GCC CAG CCG GCC ATG GCC CAG GTG CAG CTG GTG CAG TCT GG-3' |
| SEQ ID NO: 102 | HuVH2aBACKSfi | 5'-GTC CTC GCA ACT GCG GCC CAG CCG GCC ATG GCC CAG GTC AAC TTA AGG GAG TCT GG-3' |
| SEQ ID NO: 103 | HuVH3aBACKSfi | 5'-GTC CTC GCA ACT GCG GCC CAG CCG GCC ATG GCC CAG GTG CAG CTG GTG GAG TCT GG-3' |
| SEQ ID NO: 104 | HuVH4aBACKSfi | 5'-GTC CTC GCA ACT GCG GCC CAG CCG GCC ATG GCC CAG GTG CAG CTG CAG GAG TCG GG-3' |
| SEQ ID NO: 105 | HuVH5aBACKSfi | 5'-GTC CTC GCA ACT GCG GCC CAG CCG GCC ATG GCC CAG GTG CAG CTG TTG CAG TCT GC-3' |
| SEQ ID NO: 106 | HuVH6aBACKSfi | 5'-GTC CTC GCA ACT GCG GCC CAG CCG GCC ATG GCC CAG GTA CAG CTG CAG CAG TCA GG-3' |
| SEQ ID NO: 109 | SYNLIB1 | 5'-GCC TCC ACC TCT CGA GAC GGT GAC CAG GGT ACC TTG GCC CCA ATA GTC AAA ((A/C)NN)5 TCT TGC ACA GTA ATA CAC GGC CGT GTC-3' |

The examples illustrate embodiments of processes according to the present invention as follows:

In the work described in example 1, a mouse antibody directed against an epitope of TNF was cloned as a Fab fragment for display on phage, and by combining the heavy chain with repertoires of human light chains (or indeed the light chain with repertoires of human heavy chains), it was possible to select phage bearing Fab fragments with one mouse and one human chain. These antibody fragments bound to the same epitope of TNF as the original mouse antibody. The new human chain (heavy or light) was then combined with a repertoire of human partner chains to create an entirely human antibody Fab fragment which binds to the same epitope of TNF.

Example 2 illustrates CDR imprinted selection in a dual combinatorial format. An anti-HIV gp120 antibody was humanised by epitope imprinted selection with retention of the original mouse heavy chain CDR3. The VH and VL domains of the mouse antibody were cloned as fusions with mouse CH1 and Ck chains. The resulting heavy chain VHCH1 fragment was displayed on phage in combination with a repertoire of human light chains expressed as a g3p fusion from phage vector. Human light chains displayed on phage were selected and the selected chains displayed in phage in combination with a library of human naive heavy chain VHCH1 fragments amplified so as to comprise the CDR3 of the original mouse heavy chain, expressed as g3p fusions. Selected phage were obtained displaying antibody polypeptide dimers which retain the original specificity against gp120 but are now of fully human origin apart from retaing the mouse heavy chain CDR3.

Example 3 illustrates CDR imprinted selection in a single replicon, single chain Fv format. An anti-HIV gp120 antibody was humanised by epitope imprinted selection with retention of the original mouse heavy chain CDR3. A single chain Fv library was displayed on phage, the fragments comprising the original mouse light chain and CDR3 of the heavy chain but with the remainder of the light being of human origin, derived from a library of human naive heavy chains. The heavy chain variable domain of selected phage was then combined with a repertoire of human light chain variable domains to generate a scFv library on phage. Phage selected from this library displayed scFv fragments in which the variable domains were of fully human origin except for the retention of CDR3 of the mouse heavy chain.

Example 4 illustrates the isolation of human antibodies derived from the immune repertoire of an immunised mouse. A repertoire of mouse heavy and light chain V genes derived from a mouse immunised with TNF are displayed as single chain Fv fragments and phage selected for binding to TNF. VH genes derived from this selected mouse population are then combined with VL genes derived from a human naive library as single chain Fv fragments and phage selected. Selected semi-humanised antibody polypeptide dimers are then fully humanised by pairing the human VLs with human VHs derived from a human naive library. Fully humanised antibody polypeptide dimers specific for TNF may then be selected from the resulting library.

Example 5 illustrates creation of a synthetic library.

EXAMPLE 1

Humanisation of a murine antibody: Isolation of human antibodies directed against a specific epitope on tumour necrosis factor alpha (TNF-alpha) using epitope imprinted selection We chose a murine monoclonal antibody directed against human TNF as our target antibody for humanisation by double chain shuffling. The antibody Mab32 (class IgG2b, k) (D. Rathjen et al., 1991Mol. Immunol. 28, p79; D. Rathjen et al, 1992 Brit. J. Cancer 65, pp852–856; Australian Patent Application 7,576; EP 486,526) does not inhibit the cytolytic effect of TNF (presumably because it does not inhibit the binding of TNF to its receptors), but it enhances the in vivo anti-cancer and anti-viral effects of the cytokine. The antibody binding site is localised in a region of the TNF-trimer, which encompasses the first 18 residues of TNF. This example demonstrates that epitope imprinted selection can be used to generate human antibodies specifically recognising this same epitope on human TNF-alpha.

Experimental and Results

General methods used are given at the end of this section.
1 Cloning and display of the V genes of Mab 32 on phage
  Cloning of the V-genes of Mab32:
    The genes of the mouse Mab32 antibody (IgG2b, Kappa) were rescued by PCR essentially as described (Clackson et al., 1991, supra, Clackson et al in "PCR: a practical approach, eds Mr Phenox et al, IRL Press, Oxford pp 187–214) using the primers VH1BACk and VH1FOR2 for the VH gene and VK2BACK and VK4FOR for the VL gene and the polymerase chain reaction (PCR, R. K. Saiki et al., 1985, Science 230, p1350). The mouse VH and Vk genes were assembled for expression as scFv fragments by PCR assembly (Clackson et al., supra) amplified with VH1BACKSfi and VKFOR4NOT and ligated into phagemid pHEN1 (H. R. Hoogenboom et. al., 1991 Nucl. Acids. Res. 19, pp4133–4137) as a SfiI-NotI cut restriction fragment, and electroporated into E. coli HB2151 cells. Of 96 clones analysed by ELISA (see below), 9 secreted TNF-binding soluble scFv fragments. Sequencing revealed in all clones a mouse VH of family IIB and a mouse Vk of family VI (E. A. Kabat et al., 1991 Sequences of Proteins of Immunological Interest, U.S. Public Health Services). Nucleotide mutations which were probably introduced by the PCR were detected by comparing the 9 sequences, and a clone with 'consensus' sequence and binding activity (scFv-Mab32) chosen for further cloning experiments (FIG. 5).

Reclonning of the Mab32 V-genes for soluble expression:
  The murine V-genes were recloned for soluble expression of heavy (Fd, VHCH1) or light chain, by linking the mouse V-genes to the human CH1 (of the mu-isotype) or human Ck gene respectively by splice overlap extension. The mouse Vk gene was amplified from scFv-Mab32 DNA with oligonucleotides MOJK1FORNX (binds in joining region of V-gene; the sequences of all oligonucleotides used in these examples are shown in Table 1) and MVKBASFI (binds in 5' region and adds SfiI restriction site); the human Ck was obtained by PCR from a mouse-human chimaeric light chain gene (of NQ10.12.5, described in Hoogenboom et al., 1991, supra), with oligonucleotides MOVK-HUCK-BACK (binds in 5' of human Ck and is partially complementary with mouse Jk 1 region) and HUCKNOT16NOMYC (sits in 3' end of human Ck, retains the terminal cysteine, and tags on a NotI restriction site) as in Clackson et al, 1991 using a two fragment assembly. For linkage of the DNA fragments, the two PCR fragments were mixed and amplified with MVK-BASFI and HUCKNOT16NOMYC. The chimaeric VkCk gene was subsequently cloned as a SfiI-NotI fragment in pUC19 derivative containing the pelB signal peptide sequence and appropriate cloning sites for soluble expression of the light chain (pUC19-pelB-myc, FIG. 2). Similarly, the mouse VH gene (amplified from scFv-Mab32 with LMB3 and VH1FOR-2) was combined by splicing by overlap extension PCR with the human u-CH1 domain (amplified from human IgM-derived cDNA (Marks et al., 1991, supra WO 92/01047) with Mo-VH-Hu-CH1 and HCM1FONO, and cloned as SfiI-NotI fragment into a pUC19-pelB-myc for soluble expression of a tagged chain.

Display of the Mab32 antibody on phage:
  The chimaeric light chain was displayed on phage fd by reamplification of the mouse/human chimaeric chain with HUCKCYSNOT and MVKBAAPA and cloning into fd-tet-DOG1 as an ApaLI-NotI fragment. Cells harbouring a plasmid with the heavy Fd chain gene were grown in 2xTY containing AMP-GLU (1%) to logarithmic phase (OD600 of 0.5) and infected with a 20-fold excess of light-chain displaying phage. After 45 min at 37'C. without shaking and 45 min at 37'C. with shaking in the 2xTY, ampicillin (100 ug/ml), Glucose 1% medium, a sample was diluted into 50-fold volume of prewarmed (37'C.) 2 x TY, ampicillin (100 ug/ml) and tetracyclin (15 ug/ml), grown for 1 hr at 37'C. and then overnight at 30'C. (shaking). Phage particles collected from the supernatant of such culture displayed TNF-binding Fab fragments anchored through the light chain on their surface.

Similarly, the reversed configuration was made. The heavy chain VHCH1 fragment was cloned into fd-tet-DOG1 (after amplification of the Fd chain gene from the mouse/human chimeric construct with VH1BACKAPA and HCM1FONO), and phage used to infect cells capable of producing soluble light chain. Phage particles collected from the supernatant of such culture displayed TNF-binding Fab fragments anchored through the heavy chain VHCH1 fragment on their surface.

Figure 3:
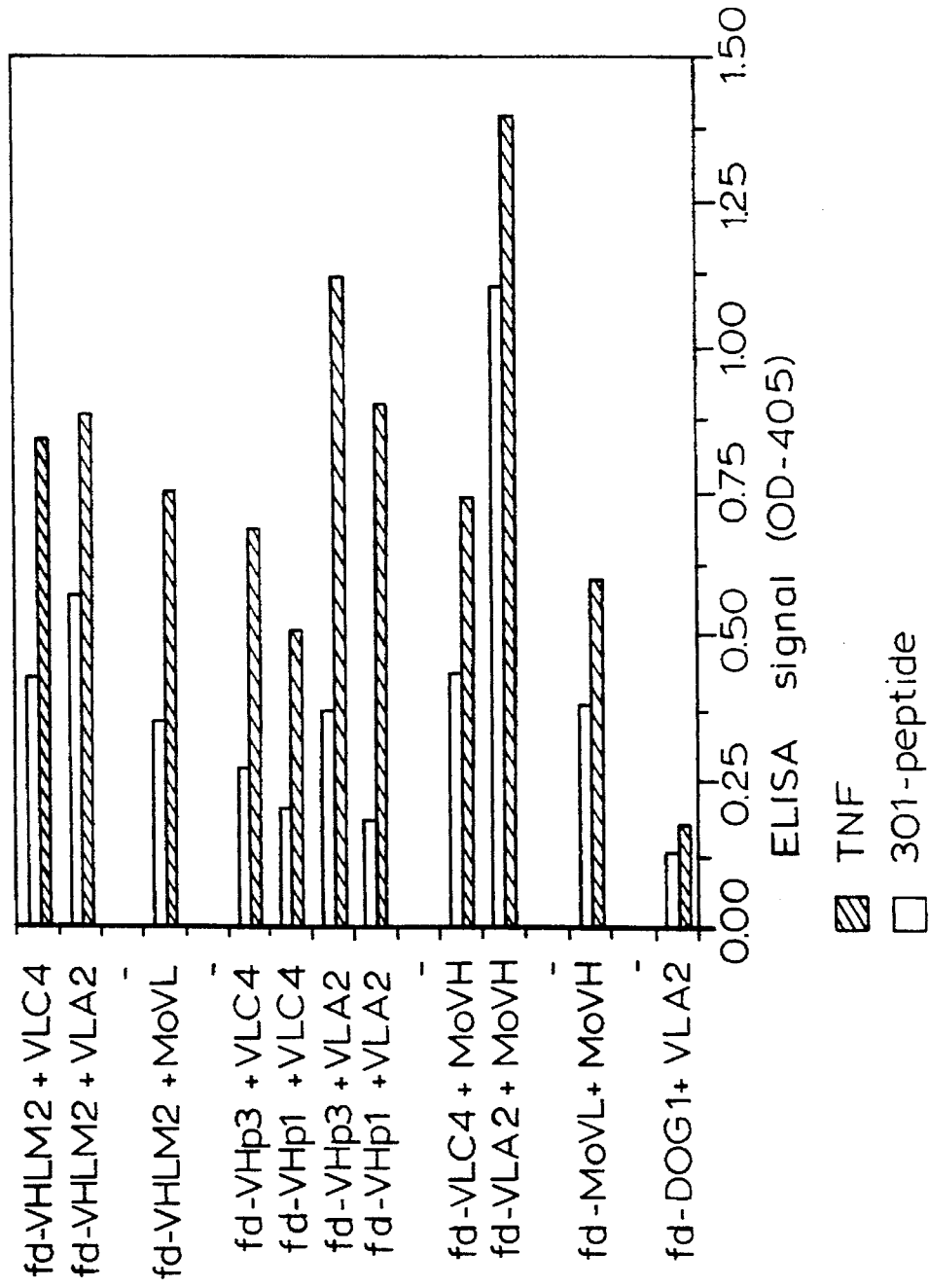
FIG. 3 shows results of ELISA of phage displaying Fab fragments, with one chain displayed on phage as a g3p fusion (indicated by fd- . . . ), and the other chain provided as a secreted, soluble chain partner.

Properties of Mab32 fragments displayed on phage:

The V-genes of the murine antibody Mab32 were cloned by amplifying the hybridoma V-genes, cloning the VH and Vk genes as scFv fragments in phagemid pHEN1 as above. Antibody scFv fragments which bind to TNF were identified by ELISA (see below for details). The mouse VH gene was recloned in pUC19-pelB-myc (FIG. 2) for soluble expression as a mouse VH linked to human mu-CH1, while the light chain was recloned with the human Ck domain in vector fd-tet-DOG1 as a fusion with g3p. When cells harbouring the heavy chain construct were infected with the fd-phage carrying the light chain, phage particles emerged which carried light chain-g3p associated with the Fd heavy chain. Indeed, binding to TNF and the 301 peptide was retained, as judged by ELISA with phage displaying the mouse-human chimaeric Fab fragment (FIG. 3). In the phage ELISA, the background signal of phage carrying the light chain only was s lightly higher than wild-type fd-tet-DOG1 phage, but always lower than the signal obtained with Fab-displaying phage. Similarly, TNF binding phage was made with the heavy chain VHCH1 fragment anchored on phage, and the light chain provided as a soluble fragment. Hence, Mab32 is functional in the dual combinatorial format in both display orientations.

2 Chain shuffling by epitope imprinted selection (EIS)

Figure 1:
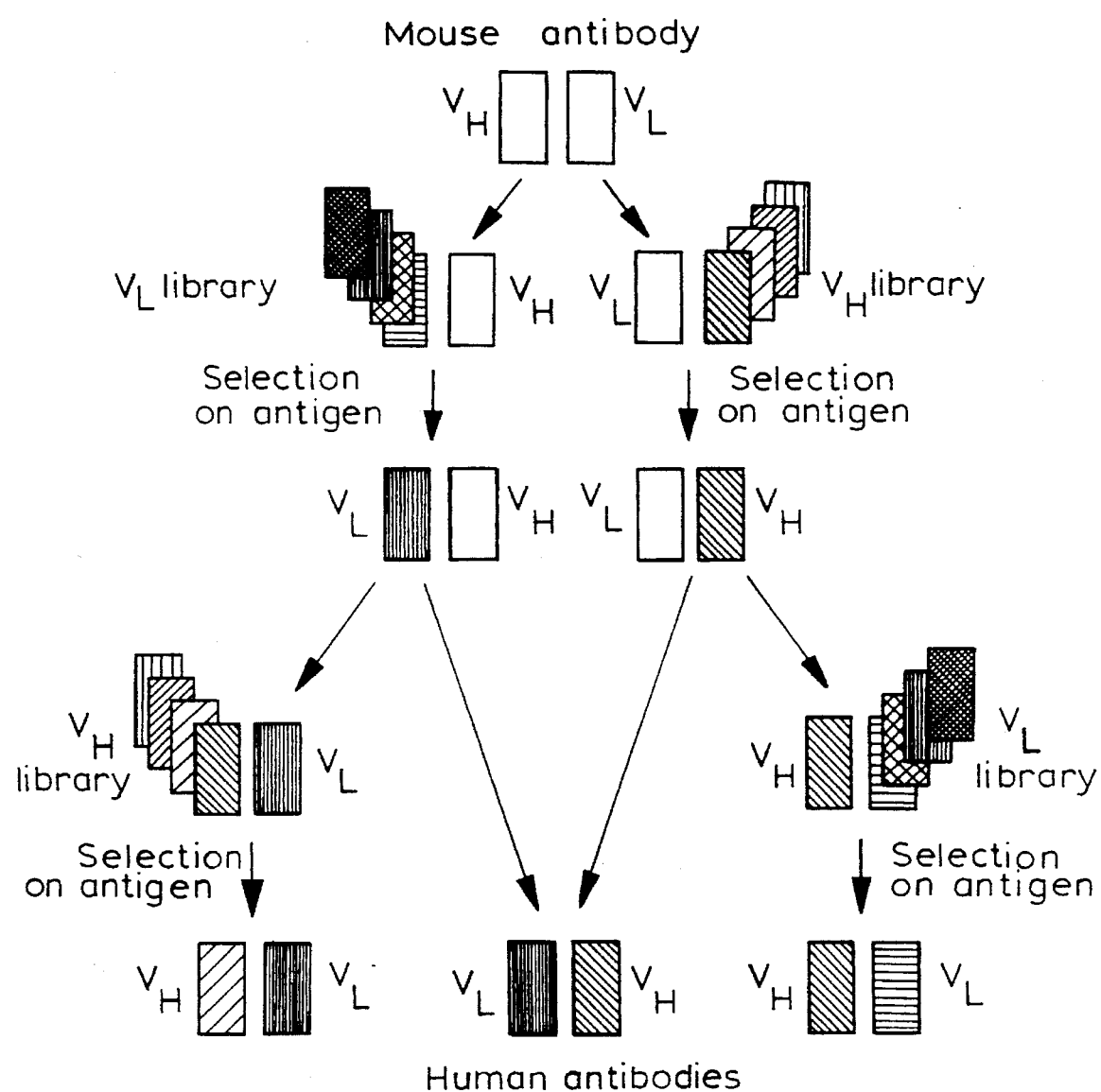
FIG. 1 shows the principle of Epitope Imprinted Selection.

Construction of One chain-Libraries:

Kappa, lambda light chain and Mu-specific cDNA was made from the mRNA prepared from the peripheral blood lymphocytes from two healthy donors essentially as in Marks et al., 1991, supra. The first-strand cDNA synthesis was performed with oligonucleotides HCM1FO, HUCLCYS and HUCKCYS for Mu-specific, lambda and kappa libraries respectively. The VH-CH 1 repertoire was amplified from this cDNA with oligonucleotides HCM1FO and six family specific VHBACK primers (as in Marks et al., 1991, supra), reamplified with a NotI-tagged forward primer (HCM1FONO) and ApaLI tagged VHBACK primers (6 primers HuVH1BAAPA to HuVH6BAAPA: Table 1). Similarly, the light chain repertoires were amplified with HUCLCYS or HUCKCYS forward primers and HUVλ1BACK to HuVλ6BACK or HuVk1BACK to HuVk6BACK back primers described in Marks et al., 1991, supra and PCT/GB91/01134 (WO 92/01047). In each case described in this section the lambda and kappa chain variable repertoires were amplified separately. The amplified repertoires were reamplified with ApaLI and NotI tagged versions of these oligonucleotides (13 back primers HuVλ1BAAPA to HuVλ6BAAPA or HuVk1BAAPA to HuVkBAAPA and two forward primers HuCLCYSNOT and HuCKCYSNOT, respectively). All three repertoires were cloned into vector fd-tet-DOG1 as ApaLI-NotI fragments, and electroporated into E. coli MC1061 cells, to obtain libraries of $1.0 \times 10^7$ clones for VλCλ, $1.4 \times 10^7$ clones for VkCk, and $5 \times 10^6$ clones for IgM-derived VHCH1. The presence of insert was checked and the frequency of inserts in the library found to be higher than 95% in all three cases. Selecting a human VL using the mouse VH domain as docking chain:

When chain shuffling using epitope imprinted selection, there are two routes from the mouse to the human antibody, depending on which mouse V-gene is kept constant in the first rounds of selection (see FIG. 1). The influence of the mouse heavy and light chain in binding to antigen and their influence on docking human partner chains onto the original epitope may vary considerably between antibodies, perhaps depending on which domain forms most of the antigen-binding contacts.

FIG. 1 shows the principle of Epitope Imprinted Selection, as exemplified using a mouse antibody to start with. The clear rectangles represent the original mouse antibody VH and VL domains. Shaded rectangles represent human VH and VL domains. The human antibodies derived shown on the left on the bottom line are produced by a procedure involving:

(a) (i) retention of the original mouse VH and shuffling with a library of human VL domains followed by selection by binding to antigen.

(a) (ii) shuffling of these selected human VL domains with a library of human VH domains followed by selection by binding to antigen.

The human antibodies derived shown on the right on the bottom line are derived by the alternative pathway involving:

(b) (i) retention of the original mouse VL and shuffling with a library of human VH domains followed by selection by binding to antigen.

(b) (ii) shuffling of these selected human VH domains with a library of human VL domains followed by selection by binding to antibody.

The human antibodies in the middle of the bottom line are derived by;

(c) shuffling the selected human VL chains derived in (a) (i) with the selected human VH chains derived in (b) (i) and then selecting by binding to antigen.

VH chains derived in (b) (ii) can be-combined with VL chains derived in (a) (ii) and vice versa.

The current section describes procedure (a) and subsequent sections procedures (b) and (c). This example describes the procedures in a dual replicon, dual combinatorial format although the methods are equally applicable to a single replicon, single chain Fv format.

In the first chain shuffling experiment, the mouse VH (linked to the human CH1 domain), expressed from pUC19-pelB-myc, was paired as Fab fragment with a library of $10^7$ different human VλCλ domains. Phage displaying the antibody fragments were subjected to rounds of panning on TNF-coated tubes. By following the titre of the eluted phage, the extent of selection can be monitored. After 4 rounds (with a 100-fold increase in the titre of eluted phage), 24 out of 28 individual clones were found to be binding to TNF in an ELISA with phage expressing Fab fragments (all with the mouse VH-human CH1). Phage only displaying the selected human VλCλ domains gave a background similar to phage displaying only the chimaeric mouseVk-human Ck. Sixteen clones taken after the first round of selection were found to be negative.

Only three different BstNI fingerprints were found amongst the 24 binders, with one pattern dominating (21/24). Light chains VλA2, VλC4 and VλD1 were found with frequencies of 21/24, 2/24. and 1/24 respectively. Sequencing revealed that all three light chains are derived from the same germline gene, a human Vλ1-1. Clone VλC4 has 1, clone VλD1 has 2 and clone VλA2 7 amino-acid residue differences from the germline (FIG. 6). However, clone VλA2 uses a framework-1 region which more closely resembles the germline sequence of a related Vλ1, humv1117, and therefore may be the result of a cross-over. The germline character of the clones is also noted in the CDR3 sequence, with minimal variation in sequence and no length variation between the three clones. Apparently, only a very limited number of genes with very similar sequences fit the stringent requirements (being compatible with the mouse VH and forming an antigen-binding pair). One of the surprises is that human germline encoded V-genes can supply domains that fit those conditions. However, the starting material of this library has proven to be very diverse in other experiments. For example, from an unimmunised scFv library made from the same two donors, we derived many different λ chains with a range of nucleotide mutations compared to known germline genes (Marks et al., 1991, supra). In addition, light chain genes derived from the same donors were used in a chain shuffling experiment for affinity maturation, and light chain variants (all Vλ1) with numerous mutations isolated (Marks et al., 1992, supra).

Selecting a human VH using the selected human VL domains as docking chains:

The 3 selected Vλ genes were recloned in pUC19-pelB-myc for soluble expression as VλCλ chains. *E. coli* cells harbouring the three light chain plasmids were mixed, infected with a phage library of human VHCH1 genes, expressed from the fd-tet-DOG1 library described earlier and the library subjected to rounds of panning on TNF-coated Immuno tubes. Clones were picked after 5 rounds, when the titre of eluted phage increased 100-fold. Fifteen out of 20 clones analysed by BstNI fingerprint of the DNA insert used one of two patterns (with approximately the same frequency). The 15 clones when combining their heavy chain VHCH1 fragments with the VλA2 light chain gave stronger phage ELISA signals than when combined with the VλC4 or VλD1 light chain (FIG. 3). Background signals obtained with phage displaying the heavy chain VHCH1 fragment only were similar to the signal of the murine VH-human CH1.

Sequencing revealed that the two patterns could be assigned to three unique human VH sequences (clones VHP1/2/3, with clone VHP1 having a BstNI fingerprint which is nearly identical to that of clone VHP2). Like the selected light chain genes, the selected heavy chain genes are derived from the same germline VH gene (germline DP-51 from the VH3 family, Tomlinson et al., J. Mol. Biol. 227, pp776–798 1992; FIG. 6), with minimal residue differences. FIG. 6 shows the deduced protein sequences of $V_H$ and $V_L$ antibody genes of antibody fragments binding to human TNF. The selected human V-genes were aligned to their closest germline homologue; identical residues in the selected genes are represented by hyphens. Framework 4 of the $V_H$ genes has been truncated at 4th residue. Clone VHP1 most likely is a cross-over between DP-51 and a related germline, DP-47. All three selected VH-genes have relatively short CDR3 loops (8,9 and 10 residues), but share little homology in this sequence. Since the VH-CDR3 is naturally the most diverse region of all six antibody variable loops, the chance of selecting clones with a consensus in that region is very low indeed.

Figure 4:
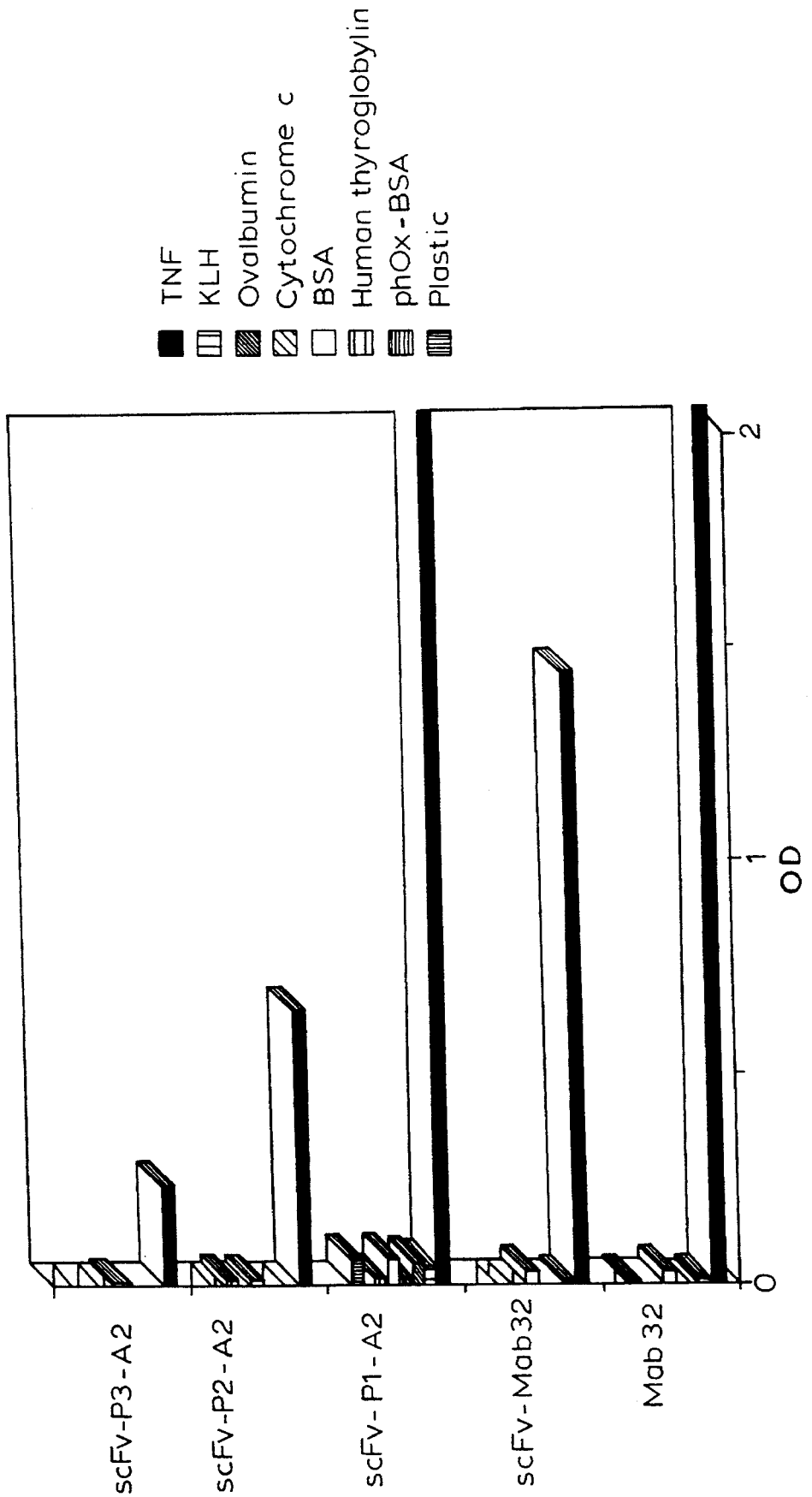
FIG. 4 shows a specificity ELISA of the original Mab32 antibody and a range of mouse (scFv-Mab32) and human (other scFv) antibodies.

Specificity of binding of the selected V-gene pairs:

A specificity ELISA with Mab32 and soluble scFv fragments on a number of antigens showed that the original Mab32 antibody, its scFv-derivative and three of the humanised TNF-binders (as scFv-fragments) bind specifically to TNF (FIG. 4). No significant binding was obtained to ELISA plates coated with keyhole limpet haemocyanin, ovalbumin, cytochrome c, bovine serum albumin, human thyroglobulin, or 2-phenyloxazol-5-one-BSA or to plastic only. Proof that the humanised antibodies bind to the same epitope came first from phage ELISA with peptide.301-coated plates and phage displaying the original mouse/human chimaeric Fab or the humanised Fab fragments (this assay is not sensitive enough to allow the detection of soluble scFv fragments) (FIG. 3). FIG. 3 shows results of ELISA of phage displaying Fab fragments, with one chain displayed on phage as a g3p fusion (indicated by fd- . . . ), and the other chain provided as a secreted, soluble chain partner. Clones display a combination of the following chains: fd-DOG 1 (no antibody); light chains: mouse $MoV_L$ (from Mab32), human VλA2 and VλC4 (selected with mouse $V_H$),; heavy chains: mouse $MoV_H$ (from Mab32), human $V_H$P1,2,3 (selected with human VλA2, VλD1, VλC4), human $V_H$LM2, $V_H$LM8 (selected with mouse $V_L$). Vλ chains are indicated as VL. Fully humanised clones were obtained which bound to both peptide 301 and TNF.

In addition, to show that the human scFv fragments compete with the original antibody for binding to TNF, we analysed binding of the scFv constructs in a competition ELISA with the Fab fragment derived by proteolytic cleavage of Mab32. Single chain Fv fragments were incubated on a TNF-coated surface with increasing amounts of the Fab fragment and the amount of bound scFv detected in ELISA (FIG. 7). Each of the scFv fragments competes with the FabMab32 for binding to TNF, including both the original scFv-Mab32 and the humanised scFv fragments.

Thus the fine specificity of Mab32 for peptide 301 of TNF is retained through the humanisation process.

Affinity of binding of the selected V gene pairs:

The mouse Mab32 antibody and purified, monomeric forms of the recombinant mouse scFv-Mab32 and the human scFv antibodies VHP1-VλA2, VH}P2-VλA2 and VHP3-VλA2, were subjected to competition ELISA for the determination of the relative affinity for TNF. Antibodies were incubated on a TNF-coated surface in the presence of increasing amounts of soluble TNF. All the clones showed a roughly similar decrease in the ELISA signal over the same range of increasing TNF concentrations (with an IC50 in the 10 nM to 100 nM range). Although the parent Mab32 has been reported to bind more strongly (affinity constant for binding to human TNF of $8.77 \times 10^9 M^{-1}$) this reflects the bivalency of the whole antibody molecule compared to the monovalency of a scFv fragment.

The Mab32 and VHP3VλA2 fragments were also analysed for binding properties using the Pharmacia BIAcore. TNF was indirectly immobilised on the surface, and the binding of antibody monitored. The properties of the original mouse antibody were analysing two monomeric forms of Mab32. On the TNF surface, the Fab fragment from Mab32 by proteolytic cleavage and the scFv Mab32 showed very similar fast off rates (approximately $10^{-2}$ s$^{-1}$). The human VHP3-VλA2 antibody has an off rate in the same range as the original scFv-Mab32. On rates for antibody protein interactions are in the range seen for the interaction between other proteins and their receptors, and cover a 100 fold range between $10^4$ and $10^6 M^{-1} s^{-1}$ (Mason D. W. and Williams, A. F., 1986, Kinetics of Antibody Reactions and the Analysis of Cell Surface Antigens, Blackwell, Oxford; Pecht, I., 1992 in Sela, M. (ed), Dynamic Aspects of Antibody Function, Academic Press Inc., New York, Vol. 6, pp 1–68). Assuming the on rates of the antibody TNF interactions are typical of antibody protein interactions, the off rate derived by the BIACore analysis is consistent with the affinity indicated by the competition ELISA (Kd=$10^{-7}$ to $10^{-8}$M).

Thus, these determinations are consistent with scFvMab32 and the humanised scFv clone VHP3-VλA2 having a similar affinity and thus with the retention of affinity, as well as specificity, through epitope imprinted selection.

Selection of humanised antibodies by alternative pathway of epitope imprinted selection; selecting human VH then VL chains:

To answer the question of whether further human chains could be selected using the alternative pathway, we first selected a human VH using the mouse VL domain as imprinting chain. After four rounds of panning, two human VH domains dominated the population (VH-LM2 and VH-LM8). Both VH genes show minimal differences compared with the germline (DP-46), which is of the VH3 family. Compared with the VHP1, 2 and 3 sequences, VH-LM2 and VH-LM8 use a germline of the same (VH3) family, and share the same canonical loop structure for CDR1 and CDR2 (I. M. Tomlinson et al., 1992, supra; C. Chothia et al., 1992 J. Mol. Biol. 227, pp789–817). However, clones VH-LM2 and VH-LM8 use a rather long VH}-CDR3 compared with VH} P1, 2 and 3 (18 and 14 amino acid residues compared to 8,9 and 10 residues respectively), and their respective germlines differ in 15 amino-acid residues. To test the complementarity of the chains selected on different (but complementary moulds), the VH-LM2 domain was combined with the human VλA2 domain either as a Fab on phage or in a scFv configuration. Both yielded binding combinations (FIG. 3 and results not shown). In addition, the mouse VL forms a relatively weak binder in combination with the human VHP3 (as Fab fragments on phage).

General Methods

Preparation of phage displaying Fab fragments on the surface using a two replicon system:

E. coli cells containing plasmid encoding the antibody chain for soluble expression were grown at 37'C. in 10 ml 2 x TY containing 100 ug/ml ampicillin and 1% glucose to an OD600 of 0.5. The cells were infected with either $10^{11}$ tranforming units (TU) prepared from the original library (by growing libraries at 37'C. in 2 x TY with tetracyclin at 15 ug/ml and collecting phage by two rounds of PEG precipitation), or with 1 ml eluate (variable titre) from the panning experiments, by incubating at 37'C. for 45 min without and 45 min with shaking. Subsequently the cells were inoculated into 500 ml of prewarmed medium with ampicillin (100 ug/ml) and tetracyclin (15 ug/ml), and after growing for 1 hour at 37'C. transferred to a 30'C. shaker for an overnight incubation. Phage was prepared by two rounds of PEG-NaCl precipitation, and resuspended in water to approximately $10^{13}$ TU/ml before selection.

Selection of binders:

Immuno tubes (Nunc) were coated overnight with 2 ml of a 10 ug TNF per ml of 50 mM bicarbonate buffer (pH 9.6). Incubation with phage, washing and elution conditions were as described by Marks et al., 1991. E. coli cells expressing the soluble complementary chain were infected with the eluted phage and grown in 2 x TY medium with tetracyclin ug/ml) for amplification of the selected phage population (as described above).

Screening clones for binding:

Individual clones were assayed for binding in phage ELISA, by preparing one-chain phage stocks, and using this phage to infect cells harbouring a gene encoding a partner chain (the one(s) which was (were) used to select the clones). Phage displaying Fab fragments prepared from such (2 ml) overnight cultures as decribed above, was 10-fold concentrated by PEG precipitation and 50 ul assayed in ELISA. Recombinant human TNF-α (produced in yeast, specific activity of $3.2 \times 10^7$ units/mg, Peptide Technology) was coated onto plastic flat-bottomed microtiterplates (Falcon 3912) at 10 ug/ml in 50 mM bicarbonate buffer (pH 9.6) or PBS, at 50 ul/well overnight at room temperature. After washing with PBS, blocking for 2 hours with 2% Dried Skimmed Milk Powder (Marvel), 50 ul phage per well was added to 50 ul 4% Marvel, after which the ELISA was continued (with anti-phage antiserum) as described (Marks et al., 1991 and PCT/GB91/01134). For the detection of binding to the Mab32 epitope, the 301-peptide (gift from Peptide Technology, sequence H-VRSSSRTPSDKPVAH-VVA-OH SEQ ID NO 119) was coated by overnight incubation at room temperature with 100 µl per well of 10 ug/ml peptide in PBS. The wells were blocked for 2 hours with 3% BSA, and the ELISA continued as above (using incubations with Marvel).

Alternatively, soluble antibody fragments were made by r ecloning the selected chains in one plasmid (either as scFv fragments), inducing expression in the appropriate strain and detecting bound antibody fragments in the supernatant of the E. coli cultures with the anti-myc-tag antibody. Purified monomeric scFv fragments (see below for purification) were used for competition ELISA experiments and to check the specificity of binding. For the specificity ELISA, plates were coated with various proteins as described (Marks et al., 1991, supra and WO 92/01047). In all cases where soluble fragments were assayed in ELISA, Marvel was replaced by BSA.

For competition ELISA, we used Fab fragment derived by proteolytic cleavage of Mab32 (gift of Peptide Technology) and either the 9E10-protein A purified mouse scFv-Mab32 or the protein A-purified human scFv fragments (VHP1/2/3-VλA2). To a TNF coated plate (blocked with 3% BSA in PBS), a mixture was added of one of each of the four scFv fragments and increasing amounts of the mouse Fab fragment (in 100 ul total volume, 1.2 ul, 4 ul and 10 ul of a 1 mg/ml solution. After incubation for 2 hours, the plate was washed, and bound scFv detected with the antibody 9E10 (which recognises the C-terminal myc-tag of the scFv fragments; Munro and Pelham 1986 Cell 46 291–300) and peroxidase labelled goat anti-mouse antibody (Fc specific). As negative control, the same antibodies were used to detect increasing amounts of Fab fragment only (the anti-mouse (Fc specific) cross-reacts weakly with the mouse Fab). Experiments were done with a range of concentrations of scFv fragments (up to 250 ug/mL), to establish the minimal detectable amount of scFv where competition was visible (when an excess of scFv is used, no competition is visible).

DNA fingerprinting and sequencing of clones:

The V-gene DNA of phage clones positive in TNF-ELISA was analysed by DNA-fingerprinting (as in Clackson et al., 1991, supra). Briefly, the genes were amplified with fd-PCR-BACK and, for heavy chains, fd-SEQ1, or, for light chains, HULAMBDASEQ, for 25 cycles (94'C., 1 min; 50'C., 1 min and 72'C., 2 min), and the DNA cut with BstNI. Analysis of the digest by agarose gelelectrophoresis allowed then to identify major differences between the positive clones. The nucleic acid sequences of selected V-regions were determined by the dideoxy chain termination method (F. Sanger et al., 1977 Proc. Natl. Acad. Sci. USA 74, pp5463–5467) using a Sequenase kit (USB) and appropriate sequencing primers. Murine V-genes cloned into pHEN1 were sequenced with pHEN-SEQ and LINKSEQ; human VH genes were sequenced with a primer sited in the human CH1(mu) region (Hu-MCH1FORSEQ2), while for human Vλ genes, HULAMBDASEQ was taken.

Recloning selected chains for soluble expression:

Selected light chains were amplified with SfiI-tagged backward and NotI tagged forward primers for cloning into pUC19-pelB-myc. Human light chains VλA2, VλD1 and VλC4 were amplified from fd with HuVL1BACKSFI and HuCL1FORAMBNOT and cloned into pUC19-pelB-myc (as SfiI-NotI fragments) for soluble expression as tag-less light chains (in non-suppressor strains).

Alternatively, selected V-genes were assembled as scFv genes essentially as described (Clackson et al., 1991, supra; Marks et al., 1991, supra and WO 92/01047) using oligonucleotides described in Marks et al. (1991, supra and WO 92/01047) and cloned into pHEN1 (Hoogenboom et al., 1991, supra) for expression in HB2151 *E. coli* cells as soluble scFv fragments with a C-terminal myc-tag.

Purification of scFv fragments:

The original mouse scFv-Mab32-c14 fragment with the C-terminal myc-tag was purified from *E. coli* supernatant using an affinity 9E10-Protein A column (as described in Clackson et al., 1991, supra). The human scFv fragments (all with VH3 genes) were purified on Protein A-sepharose columns (H. R. Hoogenboom and G. Winter, J. Mol. Biol. 227, pp381–388, 1992). All proteins were further purified using gelfiltration (Superdex-75, Pharmacia), and the monomeric fraction taken for BIAcore analysis.

Standard polymerase chain reaction

The standard reaction mixture for the polymerase chain reaction was: 5 µl template DNA; 20 pmol back primer(s); 20 pmol forward primer(s); 10 mM KCl; 10 mM $(NH_4)_2SO_4$; 20 mM Tris HCl (pH88); 2 mM $MgCl_2$; 100 µg BSA/ml and 1 unit Taq DNA polymerase (Perkin Elmer Cetus). The reaction mixture was overlaid with mineral oil and subjected to 30 cycles of amplification using a Techne thermal cycler (Duxford, England). The cycle was 94° C. for 1 min (denaturation), 55° C. for 1 min (annealing) and 72° C. for 1.5 min (extension). Other PCR conditions are given in the text or in references.

Purification of DNA products

Products were purified following agarose gel electrophoresis using Geneclean (Bio101) or by electroelution and ethanol precipitation (J Sambrook et al 1989 Molecular Cloning: A Laboratory Manual, Cold Spring Harbor Laboratory Press, Cold Spring Harbor, N.Y.)

Restriction enzyme digests

Were performed according to the manufacturers instructions (New England Biolabs, CP Labs, Bishops Stortford, Herts). Ligations were performed according to Sambrook et al (1989 supra).

Conclusion

We have shown that a mouse antibody can be rebuilt into a human antibody with the same specificity by the process of epitope imprinted selection (EIS).

A library of human light chains were shuffled with a mouse VH domain, binding combinations selected and then used in a second shuffle as 'docking domains' for a library of human VH genes. Completely human antibodies were isolated from such 'genuine' human library. The antibodies were shown to bind retain binding specificity. Alternatively, the mouse VL was used as docking chain for selecting human VH partners. Such VH domains can be used to find human VL genes, or, alternatively, can be combined with human VL domains selected with the mouse VH domain. Indeed, binding activity was obtained by combining two independently selected V-genes, pointing towards potential additivity of the EIS procedure.

The EIS approach may serve to humanise antibodies more rapidly than by CDR-grafting (Riechmann et al., 1988, supra), as this method requires very often a detailed knowledge of the 3-D structure of the antibody. However, the EIS method can be extended to for example antibody repertoires obtained by phage selection from immunised rodents. Following immunisation with antigen, a repertoire of V-genes with high affinity and specificity may be selected and then used in a epitope imprinted selection (see example 4) to generate a range of human antibodies of high affinity and enriched for the desired specificity.

EXAMPLE 2

Humanising rodent antibodies using polycombinatorial libraries and CDR imprinting CDR 3 of the heavy chain is generally found to be the most variable of all CDRs in terms of both length and sequence, and can make important contacts with antigen (Winter, G. and Milstein C. Man-made Antibodies. (1991) Nature 349, pp293–299). This is an important consideration when humanising, whether by CDR-grafting (Patent GB2188638B) or as described in this application using chain-shuffling. It may be advantageous to apply the polycombinatorial approach to humanising by a chain-shuffling process in which the VHCDR3 sequence of the rodent antibody is imprinted upon the human VH segments.

In the polycombinatorial approach, one fragment eg VHCH1, is displayed on phage as a fusion from a phage vector and the other, eg light chain, is expressed as a soluble fragment from eg a plasmid. Super-infection with phage is used to display both fragments on phage as a Fab fragment.

In this example a mouse anti-HIVgp120 monoclonal antibody was humanised. The VH domain of this mouse antibody was fused to the human Cgamma1 domain and cloned into pUC19Sfi/Not/polymyc.

A repertoire of naive human light chains cloned as g3 fusions in fd-DOG-1 (also known as fd-CAT-2 in WO 92/01047) was then infected into the cells carrying the chimaeric heavy chain, and phage selected on antigen. These phage have both heavy and light chains on their surface, though the phage genome encodes just the light chain; this is not a problem since the only heavy chain is the one provided.

Light chains selected this way were then paired with a library of naive human VH domains, PCR-amplified in such a way that CDR3 of the human antibodies were replaced with that of the original mouse heavy chain.

Section (a) deals with construction of a chimaeric Fab fragment in which the mouse F58 VH and VL domains are fused to human CH1 and CK sequences. This clone was used in early characterisation of the antibody and served as a template for subsequent PCR amplification of the heavy chain, which was then cloned into pUC19 Sfi-Not polymyc as a PstI-Not I fragment (section (b)). Section (c) describes construction of a human light chain repertoire in fdDOG, which was then infected into cells containing the chimaeric heavy chain on pUC19 (section (d)). The resulting phage were panned against the peptide (section (e)) and the selected light chains PCR-amplified and cloned as Asc I-Not I fragments alongside the chimaeric heavy chain (section (f)) and assayed for their ability to bind antigen by ELISA (section (g)). Selected light chains were recloned in pUC (section (h)) and naive human VH domains amplified with a mutagenic primer imposing the F58 CDR3 sequence on the domains, and the resulting fragments cloned in phage (section (i)). This repertoire of imprinted heavy chain phage was then used to infect cells carrying the selected light chains on pUC and the resulting phage panned on antigen. Finally, the selected heavy and light chains are cloned together on the same replicon and assayed for binding to antigen (section (j)).

(a) Cloning of F58 chimaeric heavy chain (i) cDNA synthesis and primary PCR.

Five ml of cultured hybridoma cells (approximately $2 \times 10^6$ cells) were washed in PBS, pelleted, resuspended in 200 ul 0.1% diethylpyrocarbonate in water and immediately boiled for 5 minutes. After centrifugation, 68 ul of the 'boilate' supernatant was added to a 28 ul reaction mixture resulting in a 96 ul reaction mixture containing 140 mM KCl, 50 mM Tris.HCl (pH8.1@42'C.), 8 mM $MgCl_2$, 10 mM DTT, 500 uM deoxythymidine triphosphate, 500 uM deoxycytidine triphosphate, 500 uM deoxyadenine triphosphate and 500 uM deoxyguanine triphosphate nucleotide triphosphate (500 uM dNTPs), 160 units of human placental RNAse inhibitor and 10 pmol of forward primer. Four ul (100 units) of avian myeloblastosis virus (AMV) reverse transcriptase was added, the reaction incubated at 42'C. for 1 hour, heated to 100'C. for 3 minutes, quenched on ice and centrifuged for 5 minutes. The supernatant was then used immediately for PCR.

Separate PCR amplifications were performed for the heavy and light chains. Fifty ul reaction mixtures were prepared containing 5 ul of the supernatant from the cDNA synthesis, 250 uM dNTPs, 50 mM KCl, 100 mM Tris.HCl (pH 8.3), 1.5 mM $MgCl_2$, 175 ug/ml BSA, 20 pmol each of the appropriate mixtures of forward and back primers (Clackson, T et al. (1991) supra.) and 1 ul (5 units) Thermus aquaticus (Taq) DNA polymerase (Cetus, Emeryville, Calif.). The reaction mixture was overlaid with paraffin oil and subjected to 30 cycles of amplification using a Techne PHC-2 thermal cycler. The cycle was 94'C. for 1 minute (denaturation), 55'C. for 1 minute (annealing) and 72'C. for 1 minute (extension). The product was analyzed by running 5 ul on a 2% agarose gel. The remainder was extracted twice with ether, once with phenol/chloroform, ethanol precipitated and resuspended in 50 ul of water.

(ii) Cloning and sequencing of amplified VH and Vk DNA.

The amplified VH DNA was digested with PstI and BstEII, purified on a 2% low melting point agarose gel and ligated into M13VHPCR1 digested with PstI and BstEII (Orlandi, R., D. H. Gussow, P. T. Jones and G. Winter. (1989). Cloning immunoglobulin variable domains for expression by the polymerase chain reaction. Proc. Natl. Acad. Sci., USA, 86 (10), pp3833–7). The amplified VK DNA was digested with PvuII and Bgl II and ligated into M13VKPCR1 digested with Pvu II and Bcl I. The ligation mixtures were used to transform competent TG1 cells. Two clones from separate amplifications were sequenced for each VH and Vk chain using the dideoxynucleotide chain termination method.

(iii) Generation of an Fab construct for expression in *E. coli*

A chimaeric Fab containing the F58 variable domains and the human IgG1 CH1 and Ck domains was constructed by ligating the F58 V-domains into a vector containing the constant domains. M13VHPCR1 containing the F58 VH was digested with PstI and BstEII. The resulting F58VH fragment was then purified on a 1.5% agarose gel, isolated from the gel with Geneclean and ligated into pJM-1FabD1.3 (PCT/GB91/01134) digested with PstI and BstEII. The ligation mixture was used to transform competent *E. coli* N4830-1 cells (Gottesman, M. E., Adhya, S. and Das, A. (1980) J. Mol. Biol. 140, pp57–75) and clones containing the F58 VH identified by restriction analysis of RF DNA. The F58 Vk was amplified by PCR with the primers Vk2BACK and Vk3FOR2 (Clackson, T. et al. (1991) supra.) using M13VkPCR containing the F58 Vk as template. The PCR product was digested with SacI and XhoI, purified on a 1.5% agarose gel, isolated from the gel with Geneclean and ligated into pJM-1 Fab vector containing the F58 VH digested with SacI and XhoI. The ligation mixture was used to transform competent *E. coli* N4830-1 cells and clones containing the F58 Vk identified by restriction analysis of RF DNA.

(b) PCR and cloning of F58 chimaeric heavy chain

The F58 chimaeric heavy chain derived above was PCR amplified from F58 Fab clone DNA, using the primers VH1BACKSFI15 and HUCH1FORASCNOT (Table 1). The resulting ca. 700 bp fragment was digested with Pst I and Not I and cloned into Pst I and Not I-cut pUC19Sfi/Not/polymyc plasmid using standard procedures (Sambrook, J. et al. 1989, supra. and example 1).

(c) Construction of light chain repertoire

Kappa and lambda-chain genes were amplified separately using an equimolar mixture of the appropriate family based BACK and FORWARD primers (Table 1). Kappa-chain genes were amplified from the cDNA synthesis using HUCKFOR primer, using an equimolar mixture of the 6 HUVKBACK 1a–6a primers in conjunction with the HUCKFORSER primer. Lambda-chain genes were amplified from the cDNA synthesis using the HUCLFOR primer, and amplified using an equimolar mixture of the 7 HULBACK 1-6 primers -in conjunction with the HUCLFORSER primer. In each case 50 µl reaction mixtures were prepared containing 5 µl of the supernatant from the appropriate cDNA synthesis, 20 pmol total concentration of the BACK primers, 20 pmol total concentration of the FORWARD primers, 250 µM dNTPs, 10 mM KCl, 10 mM $(NH_4)_2SO_4$, 20 mM Tris.HCl (pH 8.8), 2.0 mM $MgCl_2$, 100 mg/ml BSA and 1 µl (1 unit) Vent DNA polymerase (New England Biolabs). The reaction mixture was overlaid with mineral (paraffin) oil and subjected to 30 cycles of amplification using a Techne thermal cycler. The cycle was 94° C. for 1 minute (denaturation), 57° C. for 1 minute (annealing) and 72° C. for 2.5 minutes (extension). The products were purified on a 2% agarose gel, isolated from the gel by Geneclean (Bio-101) and resuspended in 25 µl of $H_2O$.

Two different pullthrough reactions were now performed on each of the two light chain preparations. Kappa-chain genes were amplified in two reactions, using an equimolar mixture of the 6 HUVKBAAPA primers in conjunction with HUCKFORSERNOT. Lambda-chain genes were also amplified in two reactions, using an equimolar mixture of the 7 HUVLBAAPA primers in conjunction with HUCLFORSERNOT. Pullthrough conditions were performed as for the primary light chain PCRs above except that 25 cycles of amplification were used.

PCR products were digested with Apa LI and Not I using the standard format and cloned into Apa LI and Not I-cut fd-DOG as described in example 1. Phage were prepared from the library clones as described in example 1 and used to infect cells containing the heavy chain (see below).

(d) Production of shuffled Fab phase.

Cells containing the F58 chimaeric heavy chain were grown overnight at 37'C. in 2YTAG and 500 ul added to 50 mls fresh 2YTAmp medium, prewarmed to 37'C., in a conical flask. The cells were grown with shaking to OD600 of about 0.5 before adding a total of $10^{11}$ phage from the light chain repertoire. The culture was left at 37'C. for 45 minutes without shaking then shaken vigorously for another 45 minutes at 37'C. before adding tetracyline to 15 ug/ml and shaking overnight.

Phage were harvested by PEG precipitation of the culture supernatant as previously described (example 1) and used for selection experiments.

(e) Panning of shuffled Fab phage.

This was performed on maxisorb plates as previously described (Marks 3. et al., 1991, supra.), with the exception that the Tubes were coated with env gp120 V3 loop peptide of HIV-1 isolate IIIB dissolved to 10 ug/ml in water. This peptide was obtained from the AIDS-directed program (repository ref: ADP737) and has the sequence: CTRPNNNTRRSIRIQRGPGRAFVTIGKIGNMRQAHCN (SEQ ID NO 120) The phage eluted from the tubes were used to re-infect fresh cells containing the F58 chimaeric heavy chain and the panning/reinfection procedure repeated another three times.

(f) Recloning of selected light chains.

Selected light chains were PCR-amplified from fd-DOG Light chain DNA using primers G3LASCGTGBACK and HUCLFORSERNOT or HUCKFORSERNOT. The G3LASCGTGBACK primer anneals upstream of the translational start of the gIII signal in fd, brings in an Asc I site and a ribosome binding site (RBS). These fragments were digested with Asc I and Not I and cloned into Asc I and Not I-cleaved pUC19F58 plasmid (as shown in FIG. 8) so as to create a cistron, enabling soluble Fab to be produced. This was analysed for peptide binding in ELISA and bound antibody detected by virtue of the myc tag peptide on the end of the light chain.

(g) ELISA

This was performed as described below.

1 Inoculate 100 ul 2 x TY, 100 µg/ml ampicillin, 1% glucose in 96-well plates ('cell \tab wells', Nuclon) and grow with shaking (300 r.p.m.) overnight at 37'C.

2 Use a 96-well transfer device to transfer small inocula from this plate to a second 96-well plate containing 200 ul fresh 2 x TY, 100 ug/ml ampicillin, 0.1% glucose per well. Grow at 37'C., shaking until OD600 nm is approximately 0.9 (about 3 hrs). To the wells of the original plate, add 25 ul 60% glycerol per well and store at −70'C.

3 Add 25 ul 2 x TY, 100 ug/ml ampicillin, 9 mM IPTG (final concentration 1 mM IPTG). Continue shaking at 30'C. for a further 16 to 24 hrs.

4 Spin 4,000 r.p.m. for 10 min and use 100 ul supernatant in ELISA.

5 Coat plate (Falcon 3912) with 50 ul per well of peptide at 10 ug/ml in water. Leave overnight at room temp.

6 Rinse wells 3× with PBS, and block with 200 ul per well of 1%BSA/PBS, for 1 hr at 37'C.

7 Rinse wells 3× with PBS, then add 25 ul 6% BSA/PBS to all wells.

8 Add 100 ul culture supernatant containing soluble Fab to the appropriate wells. Mix, leave 1.5 hrs room temp.

9 Discard test solution, and wash out wells 3 times with PBS, 0.05% Tween 20 and 3 times with PBS. Pipette 100 ul of 4 ug/ml purified 9E10 antibody, in 2% Marvel/PBS, into each well. Incubate at room temp. for 1.5 hrs.

10 Discard 9E10 antibody, and wash out wells with 3 times with PBS, 0.05% Tween 20 and 3 times with PBS. Pipette 100 ul of 1:500 dilution of anti-mouse antibody (peroxidase-conjugated anti-mouse immunoglobulins, Dakopats/ICN, or peroxidase-conjugated anti-mouse IgG, Fc-specific, Sigma. A-2554). Incubate at room temp. for 1.5 hrs.

11 Discard 2nd antibody, and wash wells 3 times with PBS, 0.05% Tween 20 and 3 times with PBS.

12 Add one 10 mg ABTS (2,2'-azino bis(3-ethylbenzthiazoline-6-sulphonic acid), diammonium salt) tablet to 20 ml 50 mM citrate buffer, pH4.5. (50 mM citrate buffer, pH4.5 is made by mixing equal volumes 50 mM trisodium citrate and 50 mM citric acid).

13 Add 2 ul 30% hydrogen peroxide to the above solution immediately before dispensing.

14 Add 100 ul of the above solution to each well. Leave room temp. 20–30 min.

15 Quench by adding 50 ul 3.2 mg/ml sodium fluoride. Read at 405 nm.

Note 1: Alternatively, inoculate clones from transformation plate into 100 ul 2 x TY, 100 ug/ml ampicillin, 0.1% glucose in 96-well plates ('cell wells', Nuclon) and grow with shaking (300 r.p.m.) 37'C., shaking until OD600 nm is approximately 0.9 (about 6 hrs). Continue with step 3.

Note 2: This method is based on that of DeBellis D. and Schwartz I., 1990 Nucl. Acids Res. 18: p1311, and relies on the low levels of glucose present in the starting medium being metabolised by the time the inducer (IPTG) is added.

Note 3: 'Marvel' is dried milk powder. PBS is 5.84 g NaCl, 4.72 g $Na_2HPO_4$ and 2.64 g $NaH_2PO_4.2H_2O$, pH 7.2, in 1 liter. BSA is Bovine Serum Albumin.

(h) Subcloning selected light chains.

Light chains were PCR-amplified from DNA of selected clones using an equimolar mix of the 7 HUVLBAS FI primers in conjunction with HUCLFORSERASCNOT or an equimolar mix of the 6 HUVKBASFIprimers in conjunction with HUCKFORSERASCNOT. Reaction conditions were as described for the primary PCR reactions above except that 25 cycles of amplification were used. PCR fragments were cut with Sfi I and Not I and cloned into Sfi I and Not I-cut pUC19Sfi/Not/polym yc then transformed into TG1.

The panning/infection process described above is essentially repeated again, this time with the positions of the heavy and light chains reversed.

(i) CDR-imprinting VH

VH domains were amplified from the pooled primary PCR material prepared as described below.

Two preparations of PCR-amplified VH genes were made. Both preparations used an equimolar mixture of the HUJH-FOR primers (Table 1); in one of the preparations, 6 separate PCR amplifications were performed with each of the HUVHBACK primers individually (Table 1), and in the other, a single PCR reaction was performed with an equimolar mix of all 6 HUVHBACK primers. For all seven PCRs, 50 µl reaction mixtures were prepared containing 5 µl of the supernatant from the cDNA synthesis using the HUIGM-FOR primer, 20 pmol total concentration of the BACK primers, 20 pmol total concentration of the FORWARD primers, 250 µM dNTPs, 10 mM KCl, 10 mM $(NH_4)_2SO_4$, 20 mM Tris.HCl (pH 8.8), 2.0 mM MgCl2, 100 mg/ml BSA and 1 µl (1 units) Vent DNA polymerase (New England Biolabs). The reaction mixture was overlaid with mineral (paraffin) oil and subjected to 30 cycles of amplification using a Techne PHC-2 thermal cycler. The cycle was 94° C. for 1 minute (denaturation), 57° C. for 1 minute (annealing) and 72° C. for 1 minute (extension). The products were purified on a 1.5% agarose gel, isolated from the gel by Geneclean (Bio-101) and resuspended in 25 μl of H₂O. The seven products were then pooled and 'pullthrough' PCR reactions performed.

Six separate pullthrough reactions were performed with the mutagenic F58GRAFTJH4SAL primer and each of the HUVHBAAPA1-6 primers individually.

Pullthrough reactions were set up with the primers HUVHBAAPA (equimolar mix of all 6 primers) and HUJH-FORSAL (equimolar mix of all 4 primers). 50 μl reactions of containing 5 μl of the pooled PCR products from the previous step were amplified using the same conditions as for the primary PCR except that 25 cycles of amplification were used, and the annealing temperature was 45° C.

The resulting VH fragments were pooled and cut with Apa LI and Sal I using standard conditions and cloned into Apa LI and Xho I-cut fd-DOG-G1CH1 using standard protocols (Sal1 and Xho I produce compatible CTAG overhangs). Phage were prepared from this library as described above, this time using the heavy chain phage to infect cells carrying the selected light chains expressed in pUC19Sfi/Not/polymyc.

(j) Screening of final heavy-light combinations.

The end result of this process is a pool of selected heavy chains and a pool of selected light chains. These are now combined at random. Heavy chain clones are now PCR-amplified using an equimolar mix of all 6 HUVHBACKSFI primers in conjunction HUCH1FORA SCNOT using the procedure described in example 1. These fragments are cut with Sfi I and Asc I and gel-purified using standard procedures (Example 1), then ligated to equimolar quantities of Asc I-Not I -cut light chains produced in step f) above and Sfi I and Not I-cut pUC 19Sfi/Not/polymyc vector, also produced earlier. Alternatively, these Sfi I-Asc I fragments replace the F58 heavy chain in the constructs shown at the end of FIG. 8 (A). These constructs were then transformed into TG1 and analysed for peptide binding activity by ELISA as described above.

The end-products are completely human Fab fragments With the same or similar antigen-specificity as the parent rodent antibody.

EXAMPLE 3

Humanising rodent antibodies using random combinatorial phage display libraries and CDR grafting (CDR imprinted selection)

In the work described in this example the mouse anti-HIV-1 gp120 monoclonal antibody F58 was humanised as shown schematically in FIG. 9. A vector (pHENMBF58VL) was constructed carrying the F58 Vk-domain, the single chain Fv linker and the first residues of a human VH-framework 4 with a XhoI restriction site. This vector allows the cloning of VH repertoires as Nco I/Sal I fragments to give complete scFvs. A human repertoire of VHs was amplified by PCR in such a way that each heavy chain contained the CDR3 of the original mouse mab F58 and a human framework 4 and was finally cloned into pHENMBF58VL. The scFv library was selected for binding to a HIV-1 gp120 derived peptide. Heavy chain variable domains from selected scFvs were then combined by PCR-assembly with a repertoire of human light chain variable domains to give fully humanised scFvs and again selected for antigen binding. The procedure illustrated here is therefore a synthesis of CDR-grafting and combinatorial phage display libraries.

1. PCR amplification, cloning and sequencing of the F58 variable domains were described in example 2. Standard PCR conditions are as in example 1.

2. Construction of the F58 scFv

The VH and VL domains characterised above were assembled to form, scFv fragments, basically as described by Clackson et al, 1991, supra.

Sequences of the primers mentioned in section 2.1 are given in Clackson et al (1991 supra) except for VH1BACKSfi which is described in Hoogenboom et al, supra.

2.1 PCR amplification of the F58 VH and VL and the PCR-assembly procedure

About 1 ng of M13VHPCR1 (Orlandi et al, 1989 supra) containing the F58 VH and 1 ng of M13VkPCR (Orlandi et al, 1989 supra) containing the F58 Vk were used as template in two separate, but in terms of cycling Conditions identical, PCR amplifications: Two 50 ul reactions were prepared containing 1 ng of either the above mentioned templates, 20 pmol VH1BACK and 20 pmol VH1FOR-1 (20 pmol VK2BACK and 20 pmol VK4FOR to amplify the VL), 25.0 uM dNTPs, 5 ul 10xVent polymerase reaction buffer (as obtained from the supplier New England Biolabs) and 2 units Vent DNA polymerase. The amplifications were performed with 25 cycles of PCR (94'C. for 1 min, 55'C. for 1 min, 72'C. for 2 min).

The linker DNA was similarly amplified from about 1 ng of template DNA pSW2scD1.3 (McCafferty et al., Nature 348, 552–554, 1990) using the primers LINKBACK and LINKFOR (Clackson et al., 1991, supra).

After gel purification 1 ug each of the VH and the Vk product were mixed with 300 ng of linker in a 25 ul PCR mix without primers. and cycled 7 times (94'C. 2 min, 72'C. 4 min) to join the fragments, then amplified for 20 cycles (94'C. 1.5 min, 72'C. 2.5 min) using 25 pmol each of VH1BACK and VK4FOR primers. Finally, the assembled product was gel purified and reamplified with the primers VH1BACK-SfiI and VK4FOR-NotI to append restriction sites (Note VK4FOR and VK4FOR-NotI are equimolar mixture of 4 different primers). The F58 scFv was then digested with SfiI and NotI and cloned into the similarly digested vector pUC119Sfi-Notpolymyc. Recombinants were subsequently verified by DNA sequencing.

3. Construction of the vector pHENMBF58VL 10 ng of purified pUC119F58scFv DNA from the clone isolated above was used as template in a standard PCR amplification with the primers HuVHLBACK-XhoI and VK4FOR-NotI. The PCR product was purified, digested with XhoI and Not1 and cloned into the similarly digested vector pHEN1 to generate the new vector pHENMBF58VL.

4. Amplification and cloning of the human heavy chain repertoire 4.1. Preparation of the cDNA template The procedure was exactly as described in example 2(a)(i) using the IgM constant region forward primers described by Marks et al, 1991, supra and in WO 92/01047.

4.2. PCR of Heavy chain variable domains

The 6 separate reactions to amplify the heavy chain variable domains contained each 2 ul of the cDNA synthesis from above, 20 pmol of the individual HUVHBACKSfi primers and 20 pmol of the primer F58GRAFTSAL in an otherwise standard PCR mixture. Since the primer F58GRAF TSAL had to anneal to the framework 3 regions of the 6 human VH families, the annealing temperature for the PCR cycling was reduced to 45'C. The PCR was run for 25 cycles (94'C. 1 min, 45'C. 1 min, 72'C. 1 min), after which the products were gel purified. To obtain more material for the subsequent cloning steps a secondary PCR was performed using the same series of HuVHBACKSfi primers and the primer HuJH4FORSalI, the conditions were as above with the exception of an annealing step at 52'C. instead of 45'C.

5. Generation of the scFv library

Equal amounts each of the PCR products from above were pooled and digested with NcoI and SalI. 1 ug of this material was ligated into 3 ug of NcoI/SalI digested vector pHENMBF58VL. The Ligation reaction was processed and used for the transformation of TG1 cells as described in Hoogenboom et al supra and WO 92/01047.

6. Selection of the scFv library for antigen binders

The infection of the library in TG1 with helper phage VCSM13 and the processing of the phages for the subsequent rounds of selection was done as described (Hoogenboom et al, 1991, supra and WO 92/01047). For each selection, 8 wells of a Maxisorp plate (NUNC) were inoculated with a 50 ul solution of 3 ug/ml peptide in water. The wells were allowed to dry completely over night, blocked with 1% BSA in PBS for 30 min at room temperature and finally washed 2× with PBS. To each well were added 50 ul of phage and 150 ul of Tris-HCl, pH 8.3, 0.5M NaCl, 4% BSA. After 2 hrs the wells were washed 3× with Tris-HCl, pH 8.3, 0.1M NaCl and 3× with Tris-HCl, pH 8.3, 0.5M NaCl. Elution of bound phages and infection TG1 cells was performed as described (WO 92/01047). Briefly: Phages were eluted with 50 ul of 100 mM Triethylamine per well for 10 min. The eluted material was than immediately neutralized with ½ volume of 1M Tris-HCl, pH 7.4 and used to infect logarithmically growing TG1 cell.

The peptide antigen corresponds to the gp120 V3 loop of the HIV-1 isolate IIIB and was obtained from the AIDS-directed program of the MRC (repository reference ADP737). The sequence is:

YCTRPNNNTRRSIRIQRGPGRAFVTIGKIGNMRQAHCY (SEQ ID NO 121)

7. Analysis of selected scFvs

After 3 rounds of selection an aliquot of the eluted phages was used to infect HB2151 cells to allow for expression of soluble scFvs. The identification of individual binding clones by peptide. ELISA was done as described previously in example 2 except that scFv fragments rather than Fab fragments were prepared.

About 15% of the analysed clones scored positive at this stage, giving ELISA signals of 50%–150% of the signal obtained with the original F58 scFv which was run as a control on the same plate (see FIG. 10). None of the positive scFvs reacted with plastic, Hen eggwhite lysozyme or human thyroglobulin.

Nucleotide sequence analysis revealed that the positive clones contained somatically mutated human VH-genes derived from germ line genes of the VH-families 1 and 6 (see FIG. 11).

8. Replacing the F58 light chain variable domain by a repertoire of human light chain variable domains About 10 ng of the pooled clones, which have been shown to be active in the peptide ELISA, were used as template in a 50 ul standard PCR amplification to obtain the selected heavy chain variable domains. As primers were used 20 pmol of each LMB3 and HuJH4FORASSXhoI. The human light chain variable domains were amplified from an IgG-scFv library (WO 92/01047 example 42) using 50 ng of DNA as template with the primers fdSEQ1 and HuVHL-BACK in a standard PCR amplification. The products of both heavy and light chain amplifications were gel purified and used in a PCR assembly (1 ug each) for 7 cycles essentially as described above. Cycling conditions were 94'C. 1 min, 55'C. 1 min and 72'C. 2 min. After completing the assembly reaction the primers LMB3 and fdSEQ1 were added (20 pmol each) and the PCR was continued for further 20 cycles. The assembled products were gel purified and digested with NcoI and NotI. Finally 1 ug of cut scFvs were ligated into 3 ug of the NcoI/NotI digested vector pHEN1. The resulting library scFv was selected as described above (step 6). Finally individual clones were screened for binding to the V3 loop peptide as mentioned before (step 7).

The end products are completely human scFv fragments with the same or very similar specificity as the parent murine antibody F58, ie they bind to gp120 V3 loop but not to heterologous proteins.

EXAMPLE 4

Isolation of human antibodies derived from the immune repertoire of an immunised mouse, by epitope imprinted selection This example describes the generation of human antibodies specific for TNF-alpha from an original library of mouse antibodies derived from an immunised mouse by successive rounds of chain shuffling, illustrating a further embodiment of the present invention. The method depends upon the fact that an intermediate VH/VL combination, where one chain is mouse and the other is human, binds to the antigenic epitope to which the original mouse VH/VL pairings are directed.

In this example, it is preferable to increase the frequency of antibodies to the antigen, here TNF-alpha, in the mouse library by preselecting the mouse library for binding to the antigen. This population of mouse antibodies can then be humanised by chain shuffling. The VH chains from the selected mouse population are kept fixed and assembled with a set of human VL chains from a naive human library. This mouse VH/human VL library is then subjected to rounds of selection for binders to the antigen of interest. This selected population of semi-humanised antibodies is then fully humanised by pairing these human VLs with human VHs again derived from a naive human library. The resulting library can then be selected for binders specific for the antigen. Conversely, in the first instance mouse VL chains can be fixed and assembled with human VH chains, and after selection for binding to antigen fully humanised by pairing the isolated human VH chains with VL from the naive human library.

1. Preparation of single chain Fv phage display library from an immunised mouse

RNA is extracted from lymphocytes prepared from the spleen of a mouse hyperimmunised with TNF-alpha. DNA sequences encoding variable regions of the heavy and light chains are amplified by PCR and assembled as single chain Fv fragments as described in WO 92/01047. Sites are incorporated into the 5' and 3' ends for restriction endonucleases ApaL1 and Not1. Following digestion with ApaL1 and Not1 the assembled DNA is ligated into ApaL1/Not1 digested pCANTAB3-myc (FIG. 12) and electroporated into E. coli TG1 cells and plated on ampicillin selection media (see protocol (h) below).

2. Selection of phage displaying mouse scFv fragments binding to TNF.

Phagemids are rescued by superinfection with M13KO7 helper phage and precipitated using ⅕ volume 20% polyethylene glycol/2.5M NaCl. A selected population of TNF-alpha binding phage antibodies is prepared by panning the phage antibodies on TNF-alpha coated immunosorb tubes (1 mL, 10 ug/mL in PBS) and eluting with 1 mL 100 mM triethylamine for 5 minutes followed by neutralisation with 0.5 mL TRIS (1M, pH 7.4).

The eluted phage is used to infect 10 mL TG1 cells in logarithmic growth for 30 minutes at 37'C. and plated for ampicillin resistant colonies. The resulting colonies are scraped into 2YT media and rescued with M13KO7. Phage antibodies are selected once again on TNF-alpha coated immunosorb tubes as above. E. coli TG1 cells are infected with the eluted phage and plated and ampicillin resistant colonies are scraped into 2YT media and glycerol added to 15% and stored at −70'C. The frequency of clones binding to TNF in the selected population is checked at this stage by ELISA as described in example 1.

3. Preparation of DNA as source of fragments for chain shuffling

Human heavy and light chain DNA

A library encoding scFv fragments derived from the V genes of unimmunised humans has been constructed in the vector pHEN1 (WO 92/01047, example 42).

DNA preparation

Miniprep DNA was prepared by alkaline lysis from the colonies of the second round of selection (mouse DNA) and from the naive human library (human DNA).

Approximately $5 \times 10^7$ cells from glycerol stocks are grown overnight at 30'C. in 10 mL 2YT media containing 100 ug/mL ampicillin, 2% glucose. The cells are pelleted by centrifugation (3500 rpm, 15 minutes) and DNA prepared from the cell pellet by alkaline lysis using a commercially available kit (Promega).

4. Preparation of DNA encoding chain shuffled scFv fragments

The following primers are used:

| LMB3 | 5'CAG GAA ACA GCT ATG AC 3' | SEQ ID NO: 122 |
|---|---|---|
| FDTSEQ1 | 5'GTC GTC TTT CCA GAC GTT AGT 3' | SEQ ID NO: 123 |
| PCRHLINK | 5'ACC GCC AGA GCC ACC TCC GCC 3' | SEQ ID NO: 124 |
| LINKPCRL | 5'GGC GGA GGT GGC TCT GGC GGT 3 | SEQ ID NO: 125 |

LMB3 and FDTSEQ1 anneal, respectively, to sequences 5' and 3' flanking the antibody cloning sites of the pCANTAB series of vectors. PCRHLINK and LINKPCRL and anneal with the sequence encoding the (gly4ser3) peptide linker. Using the primers in pairs LMB3/PCRHLINK and FDTSEQ1/LINKPCRL in PCT amplifications, heavy and light chain fragments will be generated that have complementary 3'/5' ends and restriction recognition sites at the 5'/3' ends.

In this procedure the human library described by Marks et al., 1991 (supra) is used as the source of heavy chain and light chain variable domain encoding DNA. The following chain shuffling protocol is used for each shuffle. It is followed once for, e.g. shuffling human naive light chain variable domains with the mouse heavy chain variable domains and then again with the selected human light chain variable domains with the human naive heavy chain variable domains. The DNA encoding shuffled scFv fragments produced by this procedure is inserted into pCANTAB3-myc or pCANTAB5-myc (FIG. 13) depending on whether mouse VH genes or human VH genes have been used in the shuffle respectively.

(a) Primary PCR

Prepare primary heavy and light chain products in the following reactions:

| HEAVY | | LIGHT | |
|---|---|---|---|
| Miniprep DNA (e.g. mouse) | 2 ng | Miniprep DNA (e.g. human) | 2 ng |
| LMB3 primer (10 pmoles/µl) | 2.5 µl | FDTSEQ1 primer (10 pmoles/µl) | 2.5 µl |
| PCRHLINK primer (10 pmoles/µl) | 2.5 µl | LINKPCRL primer (10 pmoles/µl) | 2.5 µl |
| 10X PCR reaction buffer[1] | 5.0 µl | 10X PCR reaction buffer[1] | 5.0 µl |
| 5 mM each dNTP's | 2.5 µl | 5 mM each dNTP's | 2.5 µl |
| Taq polmerase (5 U/µl) | 0.3 µl | Taq polymerase (5 U/µl) | 0.3 µl |
| water | 37 µl | water | 37 µl |

The "reaction buffer" is 10X PCR reaction buffer: 0.1M TRIS pH 8.3, 0.5M KCl, 15 mM MgCl$_2$, 0.1% gelatine. PCR conditions are 25 cycles of 94'C. 1 minute, 60'C. 1 minute, 72'C. 2 minutes with a final 10 minutes at 72'C.

(b) Product purification

Primary PCR products are purified on agarose gels and purified using 5 ul of "glass milk" (Geneclean, Bio 101) with two elutions in water of 10 ul each.

(c) Assembly by PCR

Assembly is carried out as follows:

| purified heavy | 2.5 ul |
|---|---|
| purified light | 2.5 ul |
| 10X reaction buffer | 2 ul |
| 5 mM each dNTP's | 1.0 ul |
| Taq polymerase | 0.2 ul |
| water | 37 ul |

PCR conditions are 25 cycles of 94'C. 1 minute and 65'C. for 4 minutes, followed by a final 10 minutes at 72'C. The PCR conditions given for the primary PCR will also work, but 65'C. is preferred for the linkage reaction.

(d) Secondary PCR

For secondary PCRs use 1 ul of the linked material from (c) as template. Set the reaction up as follows:

| linked PCR product | 1 µl |
|---|---|
| LMB3 primer 10 pmoles/µl) | 2.5 µl |
| FDTSEQ1 primer (10 pmoles/µl) | 2.5 µl |
| 10X PCR reaction buffer | 5.0 µl |
| 5 mM each dNTP's | 2.5 µl |
| Taq polmerase (5 U/µl) | 0.3 µl |
| water | 37 µl |

PCR conditions are 25 cycles of 94'C. 1 minute, 60'C. 1 minute, 72'C. 2 minutes with a final 10 minutes at 72'C.

(e) Digestion of secondary PCR product (insert)

Extract the secondary PCR product with phenol:chloroform and ethanol precipitate, to remove Taq polymerase. Dissolve the PCR product in 270 ul of water, add 30 ul of 10X reaction buffer. Add 50 units Not1 and digest at 37'C. for 3 hours. Extract with phenol:chloroform and ethanol precipitate. Resuspend the pellet in 270 uL water, and add 30 uL 10X reaction buffer. If the VH used is human use Sfi1 (50 units) and digest overnight at 50'C., whereas if the VH is mouse use ApaL1 (50 units) and digest overnight at 37'C.

10X ApaL1 buffer: 0.5M potassium acetate, 0.2M TRIS-acetate, 100 mM magnesium acetate, 10 mM dithiothreitol (pH 7.9@25'C.).

10X Not1 buffer: 1.5M NaCl, 100 mM TRIS-HCl, 100 mM MgCl$_2$, 0.1% Triton X-100 (pH 7.9@25'C.).

10X Sfi1 buffer: 0.5M NaCl, 100 mM TRIS-HCl, 100 mM MgCl$_2$, 10 mM dithiothreitol (pH 7.9@25'C.).

(f) Purification of digested product

The digest is treated with phenol:chloroform, ethanol precipitated and dissolved in 20 ul water. The product is run out on a 1.5% agarose gel, the band at approximately 750 bp is excised from the gel and purified using a geneclean kit. The DNA is eluted into a final volume of 10–15 ul water and is ready for cloning.

5. Preparation of vector DNA and cloning Preparation of vector DNA

Plasmid DNA is prepared by the alkaline lysis method and is purified by cesium chloride centrifugation. The purified DNA is digested using a DNA concentration of 100 ug/ml with Sfi1 (for pCANTAB5-myc) or ApaL1 (for pCANTAB3-myc) according to manufacturers instructions (50'C. for Sfi1, overnight if convenient) followed by a 3 hour digestion with NOt 1. The digestion product is loaded on directly on to a Chromaspin 1000 column to remove the stuffer fragment and spun for 3 minutes at 2200 r.p.m. in a bench top centrifuge. The DNA was then phenol:chloroform extracted and dissolved at 100 ug/ml for use.

Ligation and transformation

Ligations are carried out using an Amersham ligation kit as follows:

| Vector DNA | 1 µl (100 ng) |
| insert DNA | 2 µl (10–50 ng) |
| 10 mMMgCl, 200 mM Tris pH 7.4 | 3 µl |
| buffer A | 24 µl |
| buffer B | 6 µl |

Incubate for 30–60 minutes at 16'C. For library preparation, use 5 times the volumes shown above. The ligation product is concentrated and purified using Geneclean and eluted into a volume of 10–15 ul of water. This is introduced into electrocompetent TG1 cells where typical transformation efficiencies are as follows:

| pUC119 | $1.6 \times 10^9$ transformants/µg |
| ligated vector with insert | $1.0 \times 10^7$ transformants/µg |
| ligated vector without insert | $2.0 \times 10^6$ transformants/µg |

6. Selection of chain shuffled clones

After each chain shuffling procedure clones which bind to TNF-a are selected by the procedure described in 2 above for selection from the mouse antibody library and binding assayed by ELISA.

7. Further shuffles

Following the initial shuffle e.g. of a selected population of mouse heavy chain variable domains with human naive light chain variable domains, the selected clones from this first shuffle are used as a source of miniprep DNA to repeat the chain shuffling and cloning procedure described in 4 and 5 above, e.g. with the human naive heavy chain variable domains of the library derived in WO 92/01047, example 42. Selection is then performed on this second shuffled library to isolate fully humanised antibodies binding to TNF-alpha derived by this repertoire imprinted selection procedure.

EXAMPLE 5

Creation of a Synthetic Library

By display of antibody repertoires on the: surface of filamentous phage and selection of the phage with antigen[1], we can mimic immune selection[2,3] and make human antibodies from the rearranged V-genes of unimmunised donors[4]. Human antibodies have now been made by synthesis from defined V-gene elements. A repertoire of 49 human germ line $V_H$ gene segments was rearranged in vitro by joining to a synthetic "D-segment" of five random amino acid residues and a J-segment, to create a synthetic third complementarity determining region[5] (CDR) of eight residues. The rearranged $V_H$ genes were cloned with a human Vλ3 light chain as single-chain Fv fragments for phage display. The library of $10^7$ phages was panned with a hapten 2-phenyl-oxazol-5-one (phOx) conjugate to bovine serum albumin (BSA), and phage isolated that encoded fragments with specific binding activity to phOx-BSA, and with affinities to phOx-gamma-aminobutyric acid (phOx-GABA) in the micromolar range. Comparison of twenty one clones with unique sequences showed that the in vitro "immune response" to the hapten was largely restricted to the $V_H 26$ segment ($V_H 3$ family)[6] with an invariant aromatic residue (Tyr, Phe, Trp) at residue 98 of CDR3. The use of V-genes rearranged in vitro may allow the design of antibody libraries biased towards the binding of antigens of known structure, and the creation of therapeutic human antibodies with reduced immunogenicity.

Antibody variable domains consist of a β-sheet framework with three loops of hypervariable sequence or CDRs[5]. The loops create antigen binding sites of a variety of shapes, ranging from flat surfaces[7] to pockets[8]. For human heavy chains, the sequence diversity of the first two CDRs are encoded by a repertoire of about fifty germ line $V_H$ segments. (I. M. Tomlinson et al., supra). The third CDR is generated from the recombination of these segments with about thirty D and six J segments[9], and although its sequence is highly variable, it often includes a salt bridge from Asp101 of the loop to Arg94 of the framework[10]. The structures and lengths of the first two CDRs are restricted[10,11], but those of CDR3 differ greatly, with lengths ranging from 4 to 25 residues[5].

A library was created of rearranged $V_H$ genes with a CDR3 of eight residues including Asp101, in combination with a single Vλ (ref.12) light chain. Forty nine germ line $V_H$ segments encoding most of the human $V_H$ repertoire (Tomlinson et al., supra) were each amplified using the polymerase chain reaction[13] and oligonucleotide primers that introduce a synthetic D-segment (of 15 bases of random sequence at the 3' end of the $V_H$ segment) and a J-segment, together encoding a CDR3 loop of eight residues (FIG. 14). The rearranged segments were pooled and cloned for phage display with a human Vλ3 light chain, creating a synthetic library of $10^7$ phage clones. Like the immune system, the synthetic library of $10^7$ phage clones can tap only a small fraction of the potential diversity. Thus the diversity is potentially $49 \times 32^5 = 1.6 \times 10^9$ different nucleotide sequences, or $49 \times 20^5 = 1.6 \times 10^8$ different amino acid sequences.

The library was subjected to four rounds of growth and panning on phOx-bovine serum albumin (BSA) coated tubes, and clones screened as soluble[14] single chain Fv fragments[15,16] for binding activity to phOx-BSA by ELISA[4]. After the third and fourth rounds, 14/96 and 61/96 clones respectively were identified with binding activities to phOx-BSA and of these (29 tested) none bound to other proteins (see legend Table 4). Furthermore their binding to phOx-BSA coated plates could be competed with the soluble hapten (Table 4).

Sequencing revealed that many (21/29) of the phOx binders were unique, with an eight residue CDR3, and utilised either a segment from the $V_H 4$ family, or one of three segments from the $V_H 3$ family (Table 4). Together these segments use three of the seven "canonical" folds available to the first two hypervariable loops of human $V_H$ segments. (C. Chothia, et al., supra). The majority of the unique clones (16/21) were derived from the VH26 segment[6] and have related sequences in the third hypervariable loop: in this group the first residue tends to have a branched aliphatic side chain (15/16), the second residue tends to be lysine or arginine (11/16), while the fourth residue is always an aromatic residue (most frequently tyrosine).

The affinities ($K_d$) of two of the stronger binders (Ox 13 and Ox-31, Table 4) for phOx-GABA were determined by fluorescence quench titration[17] as 3.1±0.2 μM and 6.7±0.7 μM respectively. Although the synthetic antibody library lacks the diverse VH-CDR3 lengths and the different light chains of antibodies made in vivo, the affinities for phOx-GABA compare with 0.5 μM for a (phage) antibody made from unimmunised human donors[4], or 1 μM for several hybridomas from a mouse primary immune response[18] (but see caveat, Table 3 legend). To improve these affinities, one could systematically alter (see below) the many different phOx antibodies selected (Table 3).

In principle, the use of phage display libraries of V-genes rearranged in vitro offers an attractive alternative to those rearranged in vivo[4]. Firstly the framework regions and first two hypervariable loops of both heavy and light chains of the synthetic human antibodies created from the library are essentially germ line. This contrasts with the "primary" phage antibodies tapped from human V-genes rearranged in vivo, in which the extent of somatic mutation varied widely[4]. Leaving aside polymorphism, the VH gene segments are identical in different individuals, and the synthetic antibodies are potentially less immunogenic. By altering the lengths and sequences of the heavy and light chain CDR3 loops, or by localising the minimal mutations in the other CDR loops, or by shuffling with synthetic "germ line" light chains[19,20], it may be possible to improve their affinities while retaining their germ line character.

Secondly both kinds of libraries are highly biased. In the "natural" libraries, the bias is outside our control, and is imposed for example by allelic variation, deletion polymorphism and deletion of self-reactive clones. In the synthetic library, the bias can be introduced systematically. Here for example, all the VH-gene segments, were chosen and thereby the folding of the first and second hypervariable loops: also fixed were the length and diversity of VH-CDR3 and the light chain. Although several ways of making diverse synthetic libraries have been suggested[2], it should also be possible to incorporate design principles into the encoded structures. If the shape of the antigen were known, an envelope of roughly complementary binding sites might be designed and built with defined V-gene elements. Use of such "designer" libraries would favour the isolation of antibodies with higher affinities.

TABLE 3

| Family | No. of genes | VH segments* | Library size × $10^{-6}$ (%) |
|---|---|---|---|
| $V_H1$ | 14 | 1–5, 7, 8, 10, 12, 14, 15, 20, 21, 25 | 2.3 (20) |
| $V_H2$ | 1 | 27 | 1.0 (9) |
| $V_H3$ | 23 | 29–33, 35, 38–40, 42, 44–54, 58, 59 | 2.1 (19) |
| $V_H4$ | 9 | 63–71 | 2.6 (23) |
| $V_H5$ | 1 | 73 | 1.4 (12) |
| $V_H6$ | 1 | 74 | 1.9 (17) |
| Total: | 49 | | 11.3 (100) |

*for simplicity $V_H$ segments are listed according to DP nomenclature of Tomlinson et al., supra.

Table 3

Composition of the Synthetic Library

Forty nine human $V_H$ segments (Tomlinson et al, supra) were used, one for each of the $V_H2$, $V_H5$ and $V_H6$ gene families and multiple segments for the other three families, and cloned according to family. Clones from the $V_H$ segments of each family (see legend FIG. 1) were checked for presence of insert (on average 85%) and pooled into a single large library as in Table 4, creating a (controlled) bias for certain gene families. The segments from the $V_H2$, $V_H5$, $V_H6$ families are thereby "overrepresented" with respect to the segments from other families. Sequencing of thirty five clones from the unselected library confirmed that $V_H$ segments from each family were present, and that the nucleotides were present in the expected ratios in the D-segment, but with a slight bias for C. (At the first and second position of each codon, A, 21.3%; G, 17.9%; C33.7% and T, 27.1%; at the third position, G, 42.6% and T, 57.4%). The expression levels of the antibody fragments were also checked, and $V_H$ segments were identified in clones with detectable expression levels, for example $V_H1$ (DP-7), $V_H2$ (DP-27), $V_H3$ (DP-29,35,38,44,47,51,53), $V_H4$ (DP-63,69), $V_H5$ (DP-73) and $V_H6$ (DP-74).

Methods

The clones were checked for presence of insert by 'PCR-screening'[21] with oligonucleotides LMB3 and pHEN-SEQ (ref.4) and sequenced from double-stranded DNA by the dideoxy chain termination method[22] with oligonucleotide LINKSEQ (5'-CGA TCC GCC ACC GCC AGA G-3'). (The numbers in the tables are corrected for insert). Expression of soluble scFv fragments was checked by spotting 10 μl supernatant of induced overnight Cultures in E. coli HB2151 (ref.14) onto a nitrocellulose filter using a slot-blot device (Minifold II, Schleicher and Schuell), and detecting the bound peptide-tagged scFv fragments with 9E10 antibody[23] and peroxidase labelled anti-mouse antibodies (Sigma).

TABLE 4

| Clone | Family | Germline gene* | Canonical Loop structure* | $I_{50}^\phi$ |
|---|---|---|---|---|
| Ox-31 | $V_H3$ | DP-42 | 1-1 | 26 |
| Ox-15 | $V_H3$ | DP-45 | 1-1 | >300 |
| Ox-18 | " | " | " | >300 |
| Ox-33 | $V_H3$ | DP-47 | 1-3 | 20 |
| Ox-13 | " | " | " | 50 |
| Ox-9 | " | " | " | 80 |
| Ox-7 | " | " | " | 86 |
| Ox-30 | " | " | " | 86 |
| Ox-12 | " | " | " | 86 |
| Ox-5 | " | " | " | 100 |
| Ox-3 | " | " | " | 125 |
| Ox-20 | " | " | " | 125 |
| Ox-21 | " | " | " | 125 |
| Ox-4 | " | " | " | 130 |
| Ox-10 | " | " | " | 150 |
| Ox-14 | " | " | " | 180 |
| Ox-19 | " | " | " | 250 |
| Ox-25 | " | " | " | >400 |
| Ox-27 | " | " | " | ¶ |
| Ox-2§ | $V_H4$ | DP-67 | 2-1 | >400 |
| Ox-1 | " | " | " | >400 |

*Tomlinson et al., supra, Chothia et al., supra.
$^\phi$in μM, according to competition ELISA with phOx-GABA.
§shows V67A mutation in FR3.
¶Not determined.

Table 4 phOx-Binders Isolated from the Synthetic Library

Phage were prepared from the library by rescue with VCS-M13, and subjected to rounds of panning in phOx-BSA coated tubes as in ref.4. The sequences of 21 phage binding to phOx revealed four germ line VH segments, DP-42,45,47 (VH3 family) and DP-67 (VH4 family). DP-47 is identical to VH26 (ref.6, corrected in ref.24), while DP- 42, DP-45 and DP-67 only differ in one or a few framework residues from 8-1B (ref.25), 65-2 (ref.26) or VH4.22 (ref.27) respectively. Clones from the unselected library using the DP47 $V_H$ segment and lacking the characteristic pattern of CDR3 did not bind to phOx. Of the 21 phOx binders tested, none bound to BSA, NIP-BSA, plastic, chymotrypsinogen A, cytochrome c, bovine thyroglobulin, keyhole limpet haemocyanin or turkey egg white lysozyme. Four clones that bound to BSA (but not to phOx) were found to be contaminants (αBSA3 clones, from ref.4).

Methods

As in ref.4. The relative affinities of the scFv fragments were determined by inhibition ELISA[28]. A serial dilution of 4-gamma-amino-butyric acid methylene12-phenyloxazol-5-one (phOx-GABA), with concentrations ranging from 6 to 400 μM, was made in 4% Marvel-PBS, and scFv supernatant added. The concentration of phOx-GABA resulting in a 50% reduction of the signal ($I_{50}$) for binding to phOx-BSA was noted. The affinities of the clones Ox-13 and Ox-31 for phOx-GABA were determined by fluorescence quench titration using scFv purified by the c-myc tag (ref.4). Ideally, the affinity for the phOx-BSA conjugate would have been measured directly, or that for phOx-caproic acid, but phOx-GABA was used here to allow comparison with the hybridoma data of ref.18. The affinities of the antibodies for the phOx conjugate, or for phOx-caproic acid are likely to be better than those measured for phOx-GABA.

FIG. 14

Assembly of Rearranged VH Genes (See Text)

Methods

A synthetic oligonucleotide SYNLIB15' GCC TCC ACC TCT CGA GAC GGT GAC CAG GGT ACC TTG GCC CCA ATA GTC AAA ([A/C]NN)$_5$ TCT TGC ACA GTA ATA CAC GGC CGT GTC 3' (SEQ ID NO: 109, see Table 1) introduced a D-segment with a five residue random amino acid sequence, a J-segment and an XhoI restriction site, to the 3' end of each of 49 human $V_H$ germline segments (Tomlinson et al., supra). The primer was used in the polymerase chain reaction[13] with a $V_H$ family based back primer (VHBACK) incorporating an NcoI site[4]. Each $V_H$ segment clone (provided as single stranded template in M13 vector) was amplified separately at 94° C. for 1 min, 50° C. for 1 min, and 72° C. for 1.5 min, for 25 cycles, on a PHC-3 thermocycler (Techne). Each amplification was checked by electrophoresis on agarose gel, and similar amounts of DNA from $V_H$ segments of the same family were pooled, digested with NcoI and XhoI, and cloned into the vector pHEN1 (ref.14) carrying a rearranged Vλ3 light chain variable domain (IGLV3S1; ref.12) taken from a scFv fragment binding to BSA[4].

If, instead of a random oligonucleotide, an oligonucleotide encoding a CDR, eg rodent, is used, this would imprint that non-human CDR on the product synthetic human library.

References Mentioned in Example 5

1. McCafferty, J., Griffiths, A. D., Winter, G. & Chiswell D. J. (1990). *Nature*, 348, 552–554.
2. Milstein, C. (1990). *Proc R Soc Lond Biol*, 239, 1–16.
3. Winter, G. & Milstein, C (1991). *Nature*, 349, 293–299.
4. Marks, J. D., et al (1991). *J Mol Biol*, 222, 581–597.
5. Kabat, E. A., Wu, T. T., Reid-Miller, M., Perry, H. M. & Gottesman, K. S. *Sequences of proteins of immunological interest* (U.S. Department of Health and Human Services, U.S. Government Printing Office, 1987).
6. Matthyssens, G. & Rabbits, T. H. (1980). *Proc Natl Acad Sci U.S.A.*, 77, 6561–6565.
7. Amir, A. G., Mariuzza, R. A., Phillips, S. E. & Poljak, R. J. (1986). *Science*, 233, 747–753.
8.
8. Alzari, P. M., et al (1990). *Embo J*, 9, 3807–3814.
9. Ichihara, Y., Matsuoka, H. & Kurosawa, Y (1988). *Embo J*, 7, 4141–4150.
10. Chothia, C. & Lesk, A. M. (1987). *J Mol Biol*, 196, 901–917.
11. Chothia, C., et al (1989). *Nature*, 342, 877–883.
12. Frippiat, J. P., et al (1990). *Nucleic Acids Res*, 18, 7134.
13. Saiki, R. K., et al (1985). *Science*, 230, 1350–1354.
14. Hoogenboom, H. R., et al (1991). *Nucleic Acids Res*, 19, 4133–4137.
15. Huston, J. S., et al (1988). *Proc Natl Acad Sci U.S.A.*, 85, 5879–5883.
16. Bird, R. E., et al (1988). *Science*, 242, 423–426.
17. Eisen, H. N. (1964). Meth Med Research, 10, 115–121.
18. Foote, J. & Milstein, C. (1991). *Nature*, 352, 530–532.
19. Clackson, T., Hoogenboom, H. R., Griffiths, A. D. & Winter, G (1991). *Nature*, 352, 624–628.
20. Roberts, A. J., et al (1992). *Bio/Technology*, in press.
21. Gussow, D. & Clackson, T. (1989). *Nucleic Acids Res*, 17, 4000.
22. Sanger, F., Nicklen, S. & Coulson, A. R. (1977). *Proc Natl Acad Sci U.S.A.*, 74, 5463–5467.
23. Munro, S. & Pelham, H. R. B. (1986). *Cell*, 46, 291–300.
24. Chen, P. P., Liu, M. F., Sinha, S. & Carson, D. A. (1988). *Arthritis Rheum*, 31, 1429–1431.
25. Berman, J. E., et al (1988). *Embo J*, 7, 727–738.
26. Matsuda, F., et al (1990). *Embo J*, 9, 2501–2506.
27. Sanz, I., et al (1989). *Embo J*, 8, 3741–3748.
28. Rath, S., Stanley, C. M. & Steward, M. W. (1988). *J Immunol Methods*, 106, 245–249.

We claim:

1. A method of making antibody polypeptide dimers specific for an antigen of interest, having the following steps:
   (i) providing nucleic acid expression vectors which are packaged using a component of a replicable genetic display package;
   (ii) combining (a) a genetically diverse repertoire of nucleic acid sequences which each encode a first component part of an antigen-binding site of a human antibody with (b) nucleic acid which encodes a unique or genetically diverse population of a second component part of an antigen-binding site of a non-human antibody known to bind said antigen of interest, to form a library of nucleic acid sequences on said expression vectors encoding antibody polypeptide dimers, which dimers each consist of a first polypeptide chain component and a second polypeptide chain component, in combination forming an antigen-binding site of an antibody polypeptide dimer, wherein said library contains nucleic acid encoding an antibody polypeptide dimer specific for an antigen of interest;
   (iii) expressing said library from said vectors in recombinant host organism cells, each of the said first polypeptide chain components being expressed as a fusion with a component of a replicable genetic display package which thereby displays said first polypeptide chain component at the surface of replicable genetic display packages;
   (iv) selecting from said expressed library by binding with antigen a unique or restricted population of said antibody polypeptide dimers which have binding specificity for said antigen of interest, each selected antibody polypeptide dimer being associated in its respective replicable genetic display package with nucleic acid encoding said first component part of the antigen-binding site thereof.

2. A method according to claim 1 wherein said antibody polypeptide dimers are expressed as soluble polypeptides after selection in step (iv).

3. A method according to claim 1 wherein the sequence encoding each said second component part of an antigen-binding site of a non-human antibody is modified by genetic alteration, said alteration is selected from the group consisting of mutation, point mutation, insertion and deletion, to increase the homology of said second component part of an antigen-binding site to a second component part of a human antibody prior to said combining in step (ii).

4. A method according to claim 1 having an additional step (v) wherein antibody polypeptide dimers selected in step (iv) are modified by genetic alteration, said alteration is selected from the group consisting of mutation, point mutation, insertion and deletion, to remove or reduce non-human sequences.

5. A method according to claim 1 having an additional step (v) comprising:
   a) obtaining nucleic acid encoding said first component part from its replicable genetic display package, displaying an antibody polypeptide dimer selected in step VI and combining the obtained nucleic acid with a genetically diverse repertoire of nucleic acid sequences each encoding a second component part of an antigen-binding site of human antibody, to form a second library of nucleic acid sequences encoding antibody polypeptide dimers, each antibody polypeptide dimer comprising a second antibody polypeptide chain component which is expressed from nucleic acid which is packaged using a component of a replicable genetic display package, said second chain component being expressed as a fusion with a component of a replicable genetic display package which thereby display said second chain component at the surface of replicable genetic display packages, so that antibody polypeptide dimers specific for said antigen of interest, are selectable from said second library by binding with said antigen of interest.

6. A method according to claim 1 wherein said second component part of an antigen-binding site of a non-human antibody is an antibody region which binds an antigen.

7. A method according to claim 1 wherein said second component part of an antigen-binding site of a non-human antibody is an antibody complementarity determining region.

8. A method according to claim 1 wherein each antibody polypeptide dimer of any of said libraries of antibody polypeptide dimers is expressed as a single polypeptide chain.

9. A method according to claim 1 wherein each antibody polypeptide dimer of any of said libraries of antibody polypeptide dimers is expressed as two polypeptide chains.

10. A method of making human antibody polypeptide dimers specific for an antigen of interest, comprising:

(i) combining a diverse population of polypeptides each comprising a variable domain of a first polypeptide chain of a human antibody (population A) with a unique or restricted population of polypeptides each comprising a variable domain of a second polypeptide chain of a non-human antibody specific for said antigen (population B), thereby forming a library of antibody polypeptide dimers each consisting of a polypeptide which comprises a variable domain of a first polypeptide chain of a human antibody and a polypeptide chain of a non-human antibody, wherein said library contains an antibody polypeptide dimer specific for an antigen of interest;

(ii) selecting from said library a unique or restricted population of said antibody polypeptide dimers which have binding specificity for said antigen (population c);

(iii) combining a unique or restricted population of human polypeptides derived from polypeptide dimers selected in step (ii) each comprising a human first polypeptide chain (population D) with a diverse population of polypeptides each comprising a variable domain of a second polypeptide chain of a human antibody (population E), thereby forming a library of human antibody polypeptide chain dimers from which a unique or restricted population chain dimers from which a unique or restricted population of human antibody polypeptide dimers specific for said antigen (population F) are selectable.

11. A method according to claim 10 wherein:

(a) said polypeptides of population A are each expressed from a vector (X) in recombinant host organism cells as a fusion with a component of a replicable genetic display package which thereby displays said polypeptide at the surface of replicable genetic display packages in a first population of replicable genetic display packages;

(b) nucleic acid of said vector (X) is packaged using said replicable genetic display package component, whereby the genetic material of each said replicable genetic display package encodes a said polypeptide of population A, so that the antibody polypeptide dimers of population C are each associated in their respective replicable genetic display package with nucleic acid encoding a polypeptide comprising a variable domain of a first polypeptide chain of a human antibody;

(c) each of said polypeptides of population E is expressed from a vector (Y) in recombinant host organism cells as a fusion with a component of a replicable genetic display package which thereby displays it at the surface of replicable genetic display packages in a second population of replicable genetic display packages; and (d) nucleic acid of said vector (Y) is packaged using said replicable genetic display package component, whereby the genetic material of each said replicable genetic display package in the second population of replicable genetic display packages encodes a said polypeptide of population E.

12. A method according to claim 11 wherein said population A is not expressed from the same vector as said population B; and said population D is not expressed from the same vector as said population E.

13. A method according to claim 10 wherein said population A is expressed from the same vector as said population B; and said population D is expressed from the same vector as said population E.

14. A method according to claim 13 wherein each antibody polypeptide dimer of any of said libraries of antibody polypeptide dimers is expressed as a single polypeptide chain.

15. A method according to claim 11 wherein each antibody polypeptide dimer of any of said libraries of antibody polypeptide dimers is expressed as two polypeptide chains.

16. A method according to claim 10 wherein polypeptides of said population B are chimaeric, each comprising a human antibody constant domain.

17. A method according to claim 11 wherein the polypeptides of said population E each comprise a region from a non-human antibody specific for said antigen, which region is one which binds antigen.

18. A method according to claim 11 wherein the polypeptides of said population E each comprise a complementarity determining region from a non-human antibody which specifically binds said antigen.

19. A method according to claim 18 wherein said CDR is CDR3.

20. A method according to claim 11 wherein said first polypeptide chain is antibody light chain, said second polypeptide chain being antibody heavy chain.

21. A method according to claim 11 comprising an additional step of selecting said population F of human polypeptide dimers specific for said antigen.

22. A method according to claim 11 wherein any one of said populations C and F is selected by binding with said antigen.

23. The method of claim 9 wherein said single polypeptide chain is a scFv fragment.

24. The method of claim 10 wherein said two polypeptide chains are selected from the group consisting of Fv and Fab fragments.

25. The method of claim 15 wherein said single polypeptide chain is a scFv fragment.

26. The method of claim 16 wherein said two polypeptide chains are selected from the group consisting of Fv and Fab fragments.

* * * * *

SEQUENCE LISTING ( 1 ) GENERAL INFORMATION:

( i i i ) NUMBER OF SEQUENCES: 144

( 2 ) INFORMATION FOR SEQ ID NO:1:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Gln Val Lys Leu Gln Gln Ser Gly Ala Glu Leu Val Lys Pro Gly Ala
1               5                   10                  15

Ser Val Lys Met Ser Cys Lys Ala Ser Gly Tyr Thr Phe Ala Ser Tyr
            20                  25                  30

Trp Ile Asn Trp Val Lys Gln Arg Pro Gly Gln Gly Leu Glu Trp Ile
        35                  40                  45

Gly His Ile Tyr Pro Val Arg Ser Ile Thr Lys Tyr Asn Glu Lys Phe
    50                  55                  60

Lys Ser Lys Ala Thr Leu Thr Leu Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Arg Gly Asp Gly Ser Asp Tyr Tyr Ala Met Asp Tyr Trp Gly Gln
                100                 105                 110

Gly Thr Thr Val Thr Val Ser Ser
            115                 120
```

( 2 ) INFORMATION FOR SEQ ID NO:2:

( i ) SEQUENCE CHARACTERISTICS:
        ( A ) LENGTH: 360 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
CAGGTCAAAC TGCAGCAGTC AGGGGCTGAG CTTGTGAAGC CTGGGGCTTC AGTGAAAATG      60

TCCTGCAAGG CTTCTGGCTA TACCTTCGCC AGCTACTGGA TAAACTGGGT GAAGCAGAGG     120

CCTGGACAAG GCCTTGAGTG GATTGGACAT ATTTATCCTG TTAGAAGTAT TACTAAGTAC     180

AATGAGAAGT TCAAGAGTAA GGCCACACTG ACTCTAGACA CATCCTCCAG CACAGCCTAC     240

ATGCAGCTCA GCAGCCTGAC ATCTGAGGAC TCTGCGGTCT ATTATTGTTC AAGAGGGGAC     300

GGCAGTGATT ATTATGCTAT GGACTACTGG GGCCAAGGGA CCACGGTCAC CGTCTCCTCA     360
```

( 2 ) INFORMATION FOR SEQ ID NO:3:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Asp Ile Glu Leu Thr Gln Ser Pro Ala Ile Leu Ser Ala Ser Pro Gly
1               5                   10                  15

Gly Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Thr Arg Phe Ser Gly Thr
```

```
            50                      55                      60
    Gly Ser Gly Thr Ser Tyr Ser Leu Thr Ile Ser Arg Val Glu Ala Glu
    65                      70                      75                      80

Asp Ala Ala Thr Tyr Tyr Cys Gln Gln Trp Ser Arg Asn Pro Phe Thr
                        85                      90                      95

Phe Gly Ser Gly Thr Lys Leu Glu Ile Lys Arg
                        100                     105
```

( 2 ) INFORMATION FOR SEQ ID NO:4:

( i ) SEQUENCE CHARACTERISTICS:
        ( A ) LENGTH: 321 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:4:

```
GACATTGAGC  TCACCCAGTC  TCCAGCAATC  CTGTCTGCAT  CTCCAGGGGG  GAAGGTCACA     60

ATGACTTGTA  GGGCCAGCTC  AAGTGTAAGT  TACATGCACT  GGTACCAGCA  GAAGCCAGGA    120

TCCTCCCCCA  AACCCTGGAT  TTATGCCACA  TCCAACCTGG  CTTCTGGAGT  CCCTACTCGC    180

TTCAGTGGCA  CTGGGTCTGG  GACCTCTTAC  TCTCTCACAA  TCAGCAGGGT  GGAGGCTGAA    240

GATGCTGCCA  CTTATTACTG  CCAGCAGTGG  AGTCGTAACC  CATTCACGTT  CGGCTCGGGC    300

ACCAAGCTGG  AAATCAAACG  G                                                321
```

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

```
CCGTTTGATT  TCCAGCTTGG  TGCC                                              24
```

( 2 ) INFORMATION FOR SEQ ID NO:6:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

```
CATGACCACG  CGGCCCAGCC  GGCCATGGCC  GACATTGAGC  TCACCCAGTC  TCCA          54
```

( 2 ) INFORMATION FOR SEQ ID NO:7:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

```
GGCACCAAGC  TGGAAATCAA  ACGGACTGTG  GCTGCACCAT  CTGTCTTC                  48
```

( 2 ) INFORMATION FOR SEQ ID NO:8:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GAGTCATTCT CGACTTGCGG CCGCTTATTA ACACTCTCCC CTGTTGAAGC TCTT      54

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

TGAGGAGACG GTGACCGTGG TCCCTTGGCC CC      32

( 2 ) INFORMATION FOR SEQ ID NO:10:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GGGACCACGG TCACCGTCTC CTCAGGAAGT GCATCCGCCC AACCCTTTT C      51

( 2 ) INFORMATION FOR SEQ ID NO:11:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

CCACGATTCT GCGGCCGCCA CTGGAAGAGG CACGTTCTTT TCTTT      45

( 2 ) INFORMATION FOR SEQ ID NO:12:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GAGTCATTCT CGACTTGCGG CCGCACACTC TCCCCTGTTG AAGCTCTT      48

( 2 ) INFORMATION FOR SEQ ID NO:13:

( i ) SEQUENCE CHARACTERISTICS:

(A) LENGTH: 51 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GAGTCATTCT CGACTTGCGG CCGCTGAACA TTCTGTAGGG GCCACTGTCT T                51

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CACAGTGCAC TCGACATTGA GCTCACCCAG TCTCCA                                 36

(2) INFORMATION FOR SEQ ID NO:15:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

CCACGATTCT GCGGCCGCCA CTGGAAGAGG CACGTTCTTT TCTTT                       45

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TGGAAGAGGC ACGTTCTTTT CTTT                                              24

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TGAACATTCT GTAGGGGCCA CTGTCTT                                           27

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear ( i i ) MOLECULE TYPE: DNA ( x i ) SEQUENCE DESCRIPTION: SEQ ID NO:18:

ACACTCTCCC CTGTTGAAGC TCTT                           24

( 2 ) INFORMATION FOR SEQ ID NO:19:

( i ) SEQUENCE CHARACTERISTICS:
       ( A ) LENGTH: 24 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:19:

GCGATGGTTG TTGTCATTGT CGGC                           24

( 2 ) INFORMATION FOR SEQ ID NO:20:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:20:

GAATTTTCTG TATGAGG                                   17

( 2 ) INFORMATION FOR SEQ ID NO:21:

( i ) SEQUENCE CHARACTERISTICS:
       ( A ) LENGTH: 19 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:21:

GTGTGGCCTT GTTGGCTTG                                 19

( 2 ) INFORMATION FOR SEQ ID NO:22:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:22:

CTATGCGGCC CCATTCA                                   17

( 2 ) INFORMATION FOR SEQ ID NO:23:

( i ) SEQUENCE CHARACTERISTICS:
       ( A ) LENGTH: 19 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:23:

CGATCCGCCA CCGCCAGAG                                 19

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

AGGAAGTCCT GTGCGAGGCA G                                                          21

( 2 ) INFORMATION FOR SEQ ID NO:25:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

GTCCTCGCAA CTCGCGCCCA GCCGGCCATG GCCCAGTCTG TGTTGACGCA GCCGCC           56

( 2 ) INFORMATION FOR SEQ ID NO:26:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

CCACGATTCT GCGGCCGCCT ATGAACATTC TGTAGGGGTC ACTGT                      45

( 2 ) INFORMATION FOR SEQ ID NO:27:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

GCCTGAACCG CCTCCACCTC TCGAGAACGG TGACCAGGG                            39

( 2 ) INFORMATION FOR SEQ ID NO:28:

( i ) SEQUENCE CHARACTERISTICS:
        ( A ) LENGTH: 27 base pairs .
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

CTGGTCACCG TCTCGAGAGG TGGAGGC                                          27

( 2 ) INFORMATION FOR SEQ ID NO:29:

( i ) SEQUENCE CHARACTERISTICS:

(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:29:

GGAGGATGCA CTTGTCGACA CGGTGACCAG    30

(2) INFORMATION FOR SEQ ID NO:30:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:30:

CAGGTGCAGC TGGTGCAGTC TGG    23

(2) INFORMATION FOR SEQ ID NO:31:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:31:

CAGGTCAACT TAAGGGAGTC TGG    23

(2) INFORMATION FOR SEQ ID NO:32:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:32:

GAGGTGCAGC TGGTGGAGTC TGG    23

(2) INFORMATION FOR SEQ ID NO:33:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:33:

CAGGTGCAGC TGCAGGAGTC GGG    23

(2) INFORMATION FOR SEQ ID NO:34:

(i) SEQUENCE CHARACTERISTICS:
(A) LENGTH: 23 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:34:

GAGGTGCAGC TGTTGCAGTC TGC                                              23

( 2 ) INFORMATION FOR SEQ ID NO:35:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:35:

CAGTGACAGC TGCAGCAGTC AGG                                              23

( 2 ) INFORMATION FOR SEQ ID NO:36:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:36:

TGGAAGAGGC ACGTTCTTTT CTTT                                             24

( 2 ) INFORMATION FOR SEQ ID NO:37:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:37:

AGACTCTCCC CTGTTGAAGC TCTT                                             24

( 2 ) INFORMATION FOR SEQ ID NO:38:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:38:

TGAAGATTCT GTAGGGGCCA CTGTCTT                                          27

( 2 ) INFORMATION FOR SEQ ID NO:39:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:39:

TGAGGAGACG GTGACCAGGG TGCC                                             24

( 2 ) INFORMATION FOR SEQ ID NO:40:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

TGAAGAGACG GTGACCATTG TCCC         24

( 2 ) INFORMATION FOR SEQ ID NO:41:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

TGAGGAGACG GTGACCAGGG TTCC         24

( 2 ) INFORMATION FOR SEQ ID NO:42:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

TGAGGAGACG GTGACCGTGG TCCC         24

( 2 ) INFORMATION FOR SEQ ID NO:43:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

CATGACCACA GTGCACAGGT GCAGCTGGTG CAGTCTGG         38

( 2 ) INFORMATION FOR SEQ ID NO:44:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CATGACCACA GTGCACAGGT CAACTTAAGG GAGTCTGG         38

( 2 ) INFORMATION FOR SEQ ID NO:45:

( i ) SEQUENCE CHARACTERISTICS:

(A) LENGTH: 38 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:45:

CATGACCACA GTGCACAGGT GCAGCTGGTG GAGTCTGG 38

(2) INFORMATION FOR SEQ ID NO:46:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:46:

CATGACCACA GTGCACAGGT GCAGCTGCAG GAGTCGGG 38

(2) INFORMATION FOR SEQ ID NO:47:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:47:

CATGACCACA GTGCACAGGT GCAGCTGTTG CAGTCTGC 38

(2) INFORMATION FOR SEQ ID NO:48:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:48:

CATGACCACA GTGCACAGGT ACAGCTGCAG CAGTCAGG 38

(2) INFORMATION FOR SEQ ID NO:49:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:49:

GAGTCATTCT CGTGTCGACA CGGTGACCAG GGTGCC 36

(2) INFORMATION FOR SEQ ID NO:50:

(i) SEQUENCE CHARACTERISTICS:
(A) LENGTH: 36 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:50:

GAGTCATTCT CGTGTCGACA CGGTGACCAT TGTCCC 36

( 2 ) INFORMATION FOR SEQ ID NO:51:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

GAGTCATTCT CGTGTCGACA CGGTGACCAG GGTTCC 36

( 2 ) INFORMATION FOR SEQ ID NO:52:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:52:

GAGTCATTCT CGTGTCGACA CGGTGACCGT GGTCCC 36

( 2 ) INFORMATION FOR SEQ ID NO:53:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:53:

GTCCTCGCAA CTGCGGCCCA GCCGGCCATG GCCCAGTCTG TGTTGACGCA GCCGCC 56

( 2 ) INFORMATION FOR SEQ ID NO:54:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:54:

GTCCTCGCAA CTGCGGCCCA GCCGGCCATG GCCCAGTCTG CCCTGACTCA GCCTGC 56

( 2 ) INFORMATION FOR SEQ ID NO:55:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:55:

GTCCTCGCAA CTGCGGCCCA GCCGGCCATG GCCTCCTATG TGCTGACTCA GCCACC 56

( 2 ) INFORMATION FOR SEQ ID NO:56:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

GTCCTCGCAA CTGCGGCCCA GCCGGCCATG GCCTCTTCTG AGCTGACTCA GGACCC     56

( 2 ) INFORMATION FOR SEQ ID NO:57:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

GTCCTCGCAA CTGCGGCCCA GCCGGCCATG GCCCAGGTTA TACTGACTCA ACCGCC     56

( 2 ) INFORMATION FOR SEQ ID NO:58:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

GTCCTCGCAA CTGCGGCCCA GCCGGCCATG GCCCAGGCTG TGCTCACTCA GCCGTC     56

( 2 ) INFORMATION FOR SEQ ID NO:59:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:59:

GTCCTCGCAA CTGCGGCCCA GCCGGCCATG GCCAATTTTA TGCTGACTCA GCCCCA     56

( 2 ) INFORMATION FOR SEQ ID NO:60:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:60:

GTCCTCGCAA CTGCGGCCCA GCCGGCCATG GCCGACATCC AGATGACCCA GTCTCC     56

( 2 ) INFORMATION FOR SEQ ID NO:61:

( i ) SEQUENCE CHARACTERISTICS:

(A) LENGTH: 56 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:61:

GTCCTCGCAA CTGCGGCCCA GCCGGCCATG GCCGATGTTG TGATGACTCA GTCTCC     56

(2) INFORMATION FOR SEQ ID NO:62:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:62:

GTCCTCGCAA CTGCGGCCCA GCCGGCCATG GCCGAAATTG TGTTGACGCA GTCTCC     56

(2) INFORMATION FOR SEQ ID NO:63:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:63:

GTCCTCGCAA CTGCGGCCCA GCCGGCCATG GCCGACATCG TGATGACCCA GTCTCC     56

(2) INFORMATION FOR SEQ ID NO:64:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:64:

GTCCTCGCAA CTGCGGCCCA GCCGGCCATG GCCGGAACGA CACTCACGCA GTCTCC     56

(2) INFORMATION FOR SEQ ID NO:65:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:65:

GTCCTCGCAA CTGCGGCCCA GCCGGCCATG GCCGAAATTG TGCTGACTCA GTCTCC     56

(2) INFORMATION FOR SEQ ID NO:66:

(i) SEQUENCE CHARACTERISTICS:
(A) LENGTH: 78 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:66:

GAGTCATTCT CGACTTGCGG CCGCCTGCTA TTATCGGGCG CGCCTTTATT ATGAAGATTC    60

TGTAGGGGCC ACTGTCTT    78

(2) INFORMATION FOR SEQ ID NO:67:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:67:

GAGTCATTCT CGACTTGCGG CCGCCTGCTA TTATCGGGCG CGCCTTTATT AAGACTCTCC    60

CCTGTTGAAG CTCTT    75

(2) INFORMATION FOR SEQ ID NO:68:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:68:

AGACTCTCCC CTTTTGAAGC TCTT    24

(2) INFORMATION FOR SEQ ID NO:69:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:69:

TGAAGATTCT GTAGGGGCCA CTGTCTT    27

(2) INFORMATION FOR SEQ ID NO:70:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:70:

GAGTCATTCT CGACTTGCGG CGGCAGACTC TCCCCTGTTG AAGCTCTT    48

(2) INFORMATION FOR SEQ ID NO:71:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (i i) MOLECULE TYPE: DNA ( x i ) SEQUENCE DESCRIPTION: SEQ ID NO:71:

GAGTCATTCT CGACTTGCGG CCGCTGAAGA TTCTGTAGGG GCCACTGTCT T        51

( 2 ) INFORMATION FOR SEQ ID NO:72:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:72:

GACATCCAGA TGACCCAGTC TCC        23

( 2 ) INFORMATION FOR SEQ ID NO:73:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:73:

GATGTTGTGA TGACTCAGTC TCC        23

( 2 ) INFORMATION FOR SEQ ID NO:74:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:74:

GAAATTGTGT TGACGCAGTC TCC        23

( 2 ) INFORMATION FOR SEQ ID NO:75:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:75:

GACATCGTGA TGACCCAGTC TCC        23

( 2 ) INFORMATION FOR SEQ ID NO:76:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:76:

GAAACGACAC TCACGCAGTC TCC        23

( 2 ) INFORMATION FOR SEQ ID NO:77:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:77:

GAAATTGTGC TGACTCAGTC TCC                                                               23

( 2 ) INFORMATION FOR SEQ ID NO:78:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:78:

CAGTCTGTGT TGACGCAGCC GCC                                                               23

( 2 ) INFORMATION FOR SEQ ID NO:79:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:79:

CAGTCTGCCC TGACTCAGCC TGC                                                               23

( 2 ) INFORMATION FOR SEQ ID NO:80:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:80:

TCCTATGTGC TGACTCAGCC ACC                                                               23

( 2 ) INFORMATION FOR SEQ ID NO:81:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:81:

TCTTCTGAGC TGACTCAGGA CCC                                                               23

( 2 ) INFORMATION FOR SEQ ID NO:82:

( i ) SEQUENCE CHARACTERISTICS:
        ( A ) LENGTH: 23 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:82:

CACGTTATAC TGACTCAACC GCC    23

( 2 ) INFORMATION FOR SEQ ID NO:83:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:83:

CAGGCTGTGC TCACTCAGCC GTC    23

( 2 ) INFORMATION FOR SEQ ID NO:84:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:84:

AATTTTATGC TGACTCAGCC CCA    23

( 2 ) INFORMATION FOR SEQ ID NO:85:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:85:

GTCCTCGCAA CTGGCGCGCC ACAATTTCAC AGTAAGGAGG TTTAACTTGT GAAAAAATTA    60

TTATTCGCAA TT    72

( 2 ) INFORMATION FOR SEQ ID NO:86:

( i ) SEQUENCE CHARACTERISTICS:
( A ) LENGTH: 108 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:86:

GGATGCACTT GTCGACACGG TGACCAGGGT ACCTTGGCCC CAGTAGTCAA AGTAGTAGTC    60

CTCTTCGTAA TCATAGTAGA TCAGGTCACA GTAATACACG GCCGTGTC    108

( 2 ) INFORMATION FOR SEQ ID NO:87:

( i ) SEQUENCE CHARACTERISTICS:
( A ) LENGTH: 108 base pairs
( B ) TYPE: nucleic acid (C) STRANDEDNESS: single
(D) TOPOLOGY: linear (ii) MOLECULE TYPE: DNA (xi) SEQUENCE DESCRIPTION: SEQ ID NO:87:

GGATGCACTT GTCGACACGG TGACCAGGGT ACCTTGGCCC CAGTAGTCAA AGTAGTAGTC    60

CTCTTCGTAA TCATAGTAGA TCAGGTCACA GTAATACACG GCCGTGTC    108

(2) INFORMATION FOR SEQ ID NO:88:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:88:

TGAGCACACA GTGCACTCCA GTCTGTGTTG ACGCAGCCGC C    41

(2) INFORMATION FOR SEQ ID NO:89:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:89:

TGAGCACACA GTGCACTCCA GTCTGCCCTG ACTCAGCCTG C    41

(2) INFORMATION FOR SEQ ID NO:90:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:90:

TGAGCACACA GTGCACTCTC CTATGTGCTG ACTCAGCCAC C    41

(2) INFORMATION FOR SEQ ID NO:91:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:91:

TGAGCACACA GTGCACTCTC TTCTGAGCTG ACTCAGGACC C    41

(2) INFORMATION FOR SEQ ID NO:92:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:92:

TGAGCACACA GTGCACTCCA GGTTATACTG ACTCAACCGC C    41

(2) INFORMATION FOR SEQ ID NO:93:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:93:

TGAGCACACA GTGCACTCCA GGCTGTGCTC ACTCAGCCGT C    41

(2) INFORMATION FOR SEQ ID NO:94:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:94:

TGAGCACACA GTGCACTCAA TTTTATGCTG ACTCAGCCCC A    41

(2) INFORMATION FOR SEQ ID NO:95:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:95:

TGAGCACACA GTGCACTCGA CATCCAGATG ACCCAGTCTC C    41

(2) INFORMATION FOR SEQ ID NO:96:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:96:

TGAGCACACA GTGCACTCGA TGTTGTGATG ACTCAGTCTC C    41

(2) INFORMATION FOR SEQ ID NO:97:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:97:

TGAGCACACA GTGCACTCGA AATTGTGTTG ACGCAGTCTC C    41

( 2 ) INFORMATION FOR SEQ ID NO:98:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:98:

TGAGCACACA GTGCACTCGA CATCGTGATG ACCCAGTCTC C        41

( 2 ) INFORMATION FOR SEQ ID NO:99:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:99:

TGAGCACACA GTGCACTCGA AACGACACTC ACGCAGTCTC C        41

( 2 ) INFORMATION FOR SEQ ID NO:100:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:100:

TGAGCACACA GTGCACTCGA AATTGTGCTG ACTCAGTCTC C        41

( 2 ) INFORMATION FOR SEQ ID NO:101:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:101:

GTCCTCGCAA CTGCGGCCCA GCCGGCCATG GCCCAGGTGC AGCTGGTGCA GTCTGG        56

( 2 ) INFORMATION FOR SEQ ID NO:102:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:102:

GTCCTCGCAA CTGCGGCCCA GCCGGCCATG GCCCAGGTCA ACTTAAGGGA GTCTGG        56

( 2 ) INFORMATION FOR SEQ ID NO:103:

( i ) SEQUENCE CHARACTERISTICS:

( A ) LENGTH: 56 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:103:

GTCCTCGCAA CTGCGGCCCA GCCGGCCATG GCCCAGGTGC AGCTGGTGGA GTCTGG    56

( 2 ) INFORMATION FOR SEQ ID NO:104:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:104:

GTCCTCGCAA CTGCGGCCCA GCCGGCCATG GCCCAGGTGC AGCTGCAGGA GTCGGG    56

( 2 ) INFORMATION FOR SEQ ID NO:105:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:105:

GTCCTCGCAA CTGCGGCCCA GCCGGCCATG GCCCAGGTGC AGCTGTTGCA GTCTGC    56

( 2 ) INFORMATION FOR SEQ ID NO:106:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:106:

GTCCTCGCAA CTGCGGCCCA GCCGGCCATG GCCCAGGTAC AGCTGCAGCA GTCAGG    56

( 2 ) INFORMATION FOR SEQ ID NO:107:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:107:

CATGACCACA GTGCACAGGT SMARCTGCAG SAGTCWGG    38

( 2 ) INFORMATION FOR SEQ ID NO:108:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear 5,565,332

89                                                                                                         90
-continued ( i i ) MOLECULE TYPE: DNA ( x i ) SEQUENCE DESCRIPTION: SEQ ID NO:108:

CATGCCATGA CTCGCGGCCC AGCCGGCCAT GGCCSAGGTS MARCTGCAGS AGTCWGG                 57

( 2 ) INFORMATION FOR SEQ ID NO:109:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:109:

GCCTCCACCT CTCGAGACGG TGACCAGGGT ACCTTGGCCC CAATAGTCAA AMNNMNNMNN                 60

MNNMNNTCTT GCACAGTAAT ACACGGCCGT GTC                                              93

( 2 ) INFORMATION FOR SEQ ID NO:110:

( i ) SEQUENCE CHARACTERISTICS:
        ( A ) LENGTH: 105 amino acids
        ( B ) TYPE: amino acid
        ( D ) TOPOLOGY: linear ( i i ) MOLECULE TYPE: protein ( x i ) SEQUENCE DESCRIPTION: SEQ ID NO:110:

Ala Ile Glu Leu Thr Gln Pro Ala Ile Leu Ser Ala Ser Pro Gly Gly
1               5                   10                  15

Lys Val Thr Met Thr Cys Arg Ala Ser Ser Val Ser Tyr Met His
                20                  25                  30

Trp Tyr Gln Gln Lys Pro Gly Ser Ser Pro Lys Pro Trp Ile Tyr Ala
            35                  40                  45

Thr Ser Asn Leu Ala Ser Gly Val Pro Thr Arg Phe Ser Gly Ser Gly
        50                  55                  60

Thr Gly Thr Ser Tyr Ser Leu Thr Ile Ser Arg Val Glu Ala Glu Asp
65                  70                  75                  80

Ala Ala Thr Tyr Tyr Cys Gln Gln Trp Ser Arg Asn Pro Phe Thr Phe
                85                  90                  95

Gly Ser Gly Thr Lys Leu Glu Ile Lys
            100                 105

( 2 ) INFORMATION FOR SEQ ID NO:111:

( i ) SEQUENCE CHARACTERISTICS:
        ( A ) LENGTH: 98 amino acids
        ( B ) TYPE: amino acid
        ( D ) TOPOLOGY: linear ( i i ) MOLECULE TYPE: protein ( x i ) SEQUENCE DESCRIPTION: SEQ ID NO:111:

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

```
        Gly   Ser   Lys   Ser   Gly   Thr   Ser   Ala   Ser   Leu   Ala   Ile   Ser   Gly   Leu   Arg
        65                      70                        75                            80

Ser   Glu   Asp   Glu   Ala   Asp   Tyr   Tyr   Cys   Ala   Ala   Trp   Asp   Asp   Ser   Leu
                                85                        90                            95

Ser   Gly
```

( 2 ) INFORMATION FOR SEQ ID NO:112:

( i ) SEQUENCE CHARACTERISTICS:
      ( A ) LENGTH: 113 amino acids
      ( B ) TYPE: amino acid
      ( D ) TOPOLOGY: linear ( i i ) MOLECULE TYPE: protein ( x i ) SEQUENCE DESCRIPTION: SEQ ID NO:112:

```
        Gln   Ser   Val   Leu   Thr   Gln   Pro   Ser   Ser   Val   Ser   Ala   Ala   Pro   Gly   Gln
        1                       5                         10                            15

Lys   Val   Thr   Ile   Ser   Cys   Ser   Gly   Ser   Ser   Asn   Ile   Gly   Asn   Asn
                          20                        25                            30

Tyr   Val   Tyr   Trp   Tyr   Gln   Gln   Leu   Pro   Gly   Thr   Ala   Pro   Lys   Leu   Leu
                          35                        40                            45

Ile   Tyr   Arg   Asn   Asn   Gln   Arg   Pro   Ser   Gly   Val   Pro   Asp   Arg   Phe   Ser
                    50                        55                        60

Gly   Ser   Lys   Ser   Gly   Ser   Ser   Ala   Ser   Leu   Ala   Ile   Ser   Gly   Leu   Arg
        65                      70                        75                            80

Ser   Glu   Asp   Glu   Ala   Asp   Tyr   Tyr   Cys   Ala   Ala   Trp   Asp   Asp   Ser   Leu
                                85                        90                            95

Ser   Gly   Arg   Arg   Val   Val   Phe   Gly   Gly   Gly   Thr   Lys   Leu   Thr   Val   Leu
                          100                       105                           110

Gly
```

( 2 ) INFORMATION FOR SEQ ID NO:113:

( i ) SEQUENCE CHARACTERISTICS:
      ( A ) LENGTH: 113 amino acids
      ( B ) TYPE: amino acid
      ( D ) TOPOLOGY: linear ( i i ) MOLECULE TYPE: protein ( x i ) SEQUENCE DESCRIPTION: SEQ ID NO:113:

```
        Gln   Ser   Val   Leu   Thr   Gln   Pro   Ser   Ser   Ala   Ser   Gly   Thr   Pro   Gly   Gln
        1                       5                         10                            15

Arg   Val   Thr   Ile   Ser   Cys   Ser   Gly   Ser   Ser   Asn   Ile   Gly   Ser   Asn
                          20                        25                            30

Tyr   Val   Tyr   Trp   Tyr   Gln   Gln   Leu   Pro   Gly   Thr   Ala   Pro   Lys   Leu   Leu
                          35                        40                            45

Ile   Tyr   Arg   Asn   Asn   Gln   Arg   Pro   Ser   Gly   Val   Pro   Asp   Arg   Phe   Ser
                    50                        55                        60

Gly   Ser   Lys   Ser   Gly   Thr   Ser   Ala   Ser   Leu   Ala   Ile   Ser   Gly   Leu   Arg
        65                      70                        75                            80

Ser   Glu   Asp   Glu   Ala   Asp   Tyr   Tyr   Cys   Ala   Ala   Trp   Asp   Asp   Ser   Leu
                                85                        90                            95

Ser   Gly   Arg   Asp   Val   Val   Phe   Gly   Gly   Gly   Thr   Lys   Leu   Thr   Val   Leu
                          100                       105                           110

Gly
```

( 2 ) INFORMATION FOR SEQ ID NO:114:

( i ) SEQUENCE CHARACTERISTICS:
( A ) LENGTH: 113 amino acids
( B ) TYPE: amino acid
( D ) TOPOLOGY: linear ( i i ) MOLECULE TYPE: protein ( x i ) SEQUENCE DESCRIPTION: SEQ ID NO:114:

| Gln | Ser | Val | Leu | Thr | Gln | Pro | Ala | Ser | Ala | Ser | Gly | Thr | Pro | Gln |
|---|---|---|---|---|---|---|---|---|---|---|---|---|---|---|
| 1 | | | | 5 | | | | | 10 | | | | | 15 |
| Arg | Val | Thr | Ile | Ser | Cys | Ser | Gly | Ser | Ser | Asn | Ile | Gly | Ser | Asn |
| | | | 20 | | | | | 25 | | | | 30 | | |
| Tyr | Val | Tyr | Trp | Tyr | Gln | Gln | Leu | Pro | Arg | Thr | Ala | Pro | Lys | Leu | Leu |
| | | 35 | | | | | 40 | | | | | 45 | | |
| Ile | Tyr | Arg | Asn | Asn | Gln | Arg | Pro | Ser | Gly | Val | Pro | Asp | Arg | Phe | Ser |
| | 50 | | | | | 55 | | | | | 60 | | | | |
| Gly | Ser | Lys | Ser | Gly | Thr | Ser | Ala | Ser | Leu | Ala | Ile | Ser | Gly | Leu | Arg |
| 65 | | | | | 70 | | | | | 75 | | | | | 80 |
| Ser | Glu | Asp | Glu | Ala | Asp | Tyr | Tyr | Cys | Ala | Ala | Trp | Asp | Asp | Ser | Leu |
| | | | | 85 | | | | | 90 | | | | | 95 | |
| Ser | Gly | Arg | Val | Tyr | Val | Phe | Gly | Thr | Gly | Thr | Lys | Val | Thr | Val | Leu |
| | | | 100 | | | | | 105 | | | | | 110 | | |
| Gly | | | | | | | | | | | | | | | |

( 2 ) INFORMATION FOR SEQ ID NO:115:

( i ) SEQUENCE CHARACTERISTICS:
( A ) LENGTH: 113 amino acids
( B ) TYPE: amino acid
( D ) TOPOLOGY: linear ( i i ) MOLECULE TYPE: protein ( x i ) SEQUENCE DESCRIPTION: SEQ ID NO:115:

| Gln | Val | Lys | Leu | Gln | Gln | Ser | Gly | Ala | Glu | Leu | Val | Lys | Pro | Gly | Ala |
|---|---|---|---|---|---|---|---|---|---|---|---|---|---|---|---|
| 1 | | | | 5 | | | | | 10 | | | | | 15 | |
| Ser | Val | Lys | Met | Ser | Cys | Lys | Ala | Ser | Gly | Tyr | Thr | Phe | Ala | Ser | Tyr |
| | | | 20 | | | | | 25 | | | | | 30 | | |
| Trp | Ile | Asn | Trp | Val | Lys | Gln | Arg | Pro | Gly | Gln | Gly | Leu | Glu | Trp | Ile |
| | | 35 | | | | | 40 | | | | | 45 | | | |
| Gly | His | Ile | Tyr | Pro | Val | Arg | Ser | Ile | Thr | Lys | Tyr | Asn | Glu | Lys | Phe |
| | 50 | | | | | 55 | | | | | 60 | | | | |
| Lys | Ser | Lys | Ala | Thr | Leu | Thr | Leu | Asp | Thr | Ser | Ser | Ser | Thr | Ala | Tyr |
| 65 | | | | | 70 | | | | | 75 | | | | | 80 |
| Met | Gln | Leu | Ser | Ser | Leu | Thr | Ser | Glu | Asp | Ser | Ala | Val | Tyr | Tyr | Cys |
| | | | | 85 | | | | | 90 | | | | | 95 | |
| Ser | Arg | Gly | Asp | Gly | Ser | Asp | Tyr | Tyr | Ala | Met | Asp | Tyr | Trp | Gly | Gln |
| | | | 100 | | | | | 105 | | | | | 110 | | |
| Gly | | | | | | | | | | | | | | | |

( 2 ) INFORMATION FOR SEQ ID NO:116:

( i ) SEQUENCE CHARACTERISTICS:
( A ) LENGTH: 98 amino acids
( B ) TYPE: amino acid
( D ) TOPOLOGY: linear ( i i ) MOLECULE TYPE: protein ( x i ) SEQUENCE DESCRIPTION: SEQ ID NO:116:

-continued

```
Glu  Val  Gln  Leu  Val  Glu  Ser  Gly  Gly  Gly  Leu  Val  Gln  Pro  Gly  Gly
 1              5                        10                        15

Ser  Leu  Arg  Leu  Ser  Cys  Ala  Ala  Ser  Gly  Phe  Thr  Phe  Ser  Ser  Tyr
              20                        25                        30

Ser  Met  Asn  Trp  Val  Arg  Gln  Ala  Pro  Gly  Lys  Gly  Leu  Glu  Trp  Val
         35                        40                        45

Ser  Tyr  Ile  Ser  Ser  Ser  Ser  Thr  Ile  Tyr  Tyr  Ala  Asp  Ser  Val
    50                        55                        60

Lys  Gly  Arg  Phe  Thr  Ile  Ser  Arg  Asp  Asn  Ala  Lys  Asn  Ser  Leu  Tyr
 65                       70                        75                       80

Leu  Gln  Met  Asn  Ser  Leu  Arg  Asp  Glu  Asp  Thr  Ala  Val  Tyr  Tyr  Cys
                   85                        90                        95

Ala  Arg
```

(2) INFORMATION FOR SEQ ID NO:117:

(i) SEQUENCE CHARACTERISTICS:
  (A) LENGTH: 110 amino acids
  (B) TYPE: amino acid
  (D) TOPOLOGY: linear (ii) MOLECULE TYPE: protein (xi) SEQUENCE DESCRIPTION: SEQ ID NO:117:

```
Gln  Val  Gln  Leu  Leu  Gln  Ser  Gly  Gly  Gly  Leu  Val  Gln  Pro  Gly  Gly
 1              5                        10                        15

Ser  Leu  Arg  Leu  Ser  Cys  Ala  Ala  Ser  Gly  Phe  Thr  Phe  Ser  Ser  Tyr
              20                        25                        30

Ala  Met  Ser  Trp  Val  Arg  Gln  Ala  Pro  Gly  Lys  Gly  Leu  Glu  Trp  Val
         35                        40                        45

Ser  Tyr  Ile  Ser  Ser  Ser  Ser  Thr  Ile  Tyr  Tyr  Ala  Asp  Ser  Val
    50                        55                        60

Lys  Gly  Arg  Phe  Thr  Ile  Ser  Arg  Asp  Asn  Ala  Lys  Asn  Thr  Leu  Tyr
 65                       70                        75                       80

Leu  Gln  Met  Asn  Ser  Leu  Arg  Asp  Glu  Asp  Thr  Ala  Val  Tyr  Tyr  Cys
                   85                        90                        95

Ala  Arg  Ser  Leu  Val  Gly  Ala  Leu  Asp  Tyr  Trp  Gly  Gln  Gly
              100                       105                       110
```

(2) INFORMATION FOR SEQ ID NO:118:

(i) SEQUENCE CHARACTERISTICS:
  (A) LENGTH: 98 amino acids
  (B) TYPE: amino acid
  (D) TOPOLOGY: linear (ii) MOLECULE TYPE: protein (xi) SEQUENCE DESCRIPTION: SEQ ID NO:118:

```
Gln  Val  Gln  Leu  Val  Glu  Ser  Gly  Gly  Gly  Val  Val  Gln  Pro  Gly  Arg
 1              5                        10                        15

Ser  Leu  Arg  Leu  Ser  Cys  Ala  Ala  Ser  Gly  Phe  Thr  Phe  Ser  Ser  Tyr
              20                        25                        30

Ala  Met  His  Trp  Val  Arg  Gln  Ala  Pro  Gly  Lys  Gly  Leu  Glu  Trp  Val
         35                        40                        45

Ala  Val  Ile  Ser  Tyr  Asp  Gly  Ser  Asn  Lys  Tyr  Tyr  Ala  Asp  Ser  Val
    50                        55                        60

Lys  Gly  Arg  Phe  Thr  Ile  Ser  Arg  Asp  Asn  Ser  Lys  Asn  Thr  Leu  Tyr
 65                       70                        75                       80
```

```
         Leu  Gln  Met  Asn  Ser  Leu  Arg  Ala  Glu  Asp  Thr  Ala  Val  Tyr  Tyr  Cys
                             85                  90                           95

Ala  Arg
```

(2) INFORMATION FOR SEQ ID NO:119:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:119:

```
         Val  Arg  Ser  Ser  Ser  Arg  Thr  Pro  Ser  Asp  Lys  Pro  Val  Ala  His  Val
         1                   5                        10                          15

Val  Ala
```

(2) INFORMATION FOR SEQ ID NO:120:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:120:

```
         Cys  Thr  Arg  Pro  Asn  Asn  Asn  Thr  Arg  Arg  Ser  Ile  Arg  Ile  Gln  Arg
         1                   5                        10                          15

Gly  Pro  Gly  Arg  Ala  Phe  Val  Thr  Ile  Gly  Lys  Ile  Gly  Asn  Met  Arg
                        20                  25                          30

Gln  Ala  His  Cys  Asn
                   35
```

(2) INFORMATION FOR SEQ ID NO:121:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:121:

```
         Tyr  Cys  Thr  Arg  Pro  Asn  Asn  Asn  Thr  Arg  Arg  Ser  Ile  Arg  Ile  Gln
         1                   5                        10                          15

Arg  Gly  Pro  Gly  Arg  Ala  Phe  Val  Thr  Ile  Gly  Lys  Ile  Gly  Asn  Met
                        20                  25                          30

Arg  Gln  Ala  His  Cys  Tyr
                   35
```

(2) INFORMATION FOR SEQ ID NO:122:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:122:

```
CAGGAAACAG CTATGAC                                                              17
```

( 2 ) INFORMATION FOR SEQ ID NO:123:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:123:

```
GTCGTCTTTC CAGACGTTAG T                                             21
```

( 2 ) INFORMATION FOR SEQ ID NO:124:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:124:

```
ACCGCCAGAG CCACCTCCGC C                                             21
```

( 2 ) INFORMATION FOR SEQ ID NO:125:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:125:

```
GGCGGAGGTG GCTCTGGCGG T                                             21
```

( 2 ) INFORMATION FOR SEQ ID NO:126:

( i ) SEQUENCE CHARACTERISTICS:
        ( A ) LENGTH: 189 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: CDS
        ( B ) LOCATION: 34..177

( i x ) FEATURE:
        ( A ) NAME/KEY: sig_peptide
        ( B ) LOCATION: 34..99

( i x ) FEATURE:
        ( A ) NAME/KEY: mat_peptide
        ( B ) LOCATION: 100..177

( x i ) SEQUENCE DESCRIPTION: SEQ ID NO:126:

```
GCATGCAAAT TCTATTTCAA GGAGACAGTC ATA ATG AAA TAC CTA TTG CCT ACG     54
                                     Met Lys Tyr Leu Leu Pro Thr
                                     -22         -20

GCA GCC GCT GGA TTG TTA TTA CTC GCG GCC CAG CCG GCC ATG GCC CAG    102
Ala Ala Ala Gly Leu Leu Leu Leu Ala Ala Gln Pro Ala Met Ala Gln
-15             -10              -5                            1

GTG CAG CTG CAG GTC GAC CTC GAG ATC AAA CGG GCG GCC GCA GAA CAA    150
Val Gln Leu Gln Val Asp Leu Glu Ile Lys Arg Ala Ala Ala Glu Gln
            5                10                  15
```

```
AAA CTC ATC TCA GAA GAG GAT CTG AAT TAATAAGAAT TC                              189
Lys Leu Ile Ser Glu Glu Asp Leu Asn
            20                  25
```

( 2 ) INFORMATION FOR SEQ ID NO:127:

( i ) SEQUENCE CHARACTERISTICS:
        ( A ) LENGTH: 97 amino acids
        ( B ) TYPE: amino acid
        ( D ) TOPOLOGY: linear ( i i ) MOLECULE TYPE: protein ( x i ) SEQUENCE DESCRIPTION: SEQ ID NO:127:

```
Gln Val Gln Leu Gln Gln Ser Gly Ala Glu Leu Ala Ser Pro Gly Ala
 1               5                  10                  15

Ser Val Thr Leu Ser Cys Lys Ala Ser Gly Tyr Thr Phe Thr Asp His
            20                  25                  30

Ile Met Asn Trp Val Lys Lys Arg Pro Gly Gln Gly Leu Glu Trp Ile
        35                  40                  45

Gly Arg Ile Phe Pro Val Ser Gly Glu Thr Asn Tyr Asn Gln Phe Met
    50                  55                  60

Gly Lys Ala Arg Phe Ser Val Asp Arg Ser Ser Ser Thr Val Ser Met
65                  70                  75                  80

Val Leu Asn Ser Leu Thr Ser Glu Asp Pro Ala Val Tyr Tyr Cys Asp
                85                  90                  95

Leu
```

( 2 ) INFORMATION FOR SEQ ID NO:128:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:128:

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100
```

( 2 ) INFORMATION FOR SEQ ID NO:129:

( i ) SEQUENCE CHARACTERISTICS:
        ( A ) LENGTH: 97 amino acids
        ( B ) TYPE: amino acid
        ( D ) TOPOLOGY: linear ( i i ) MOLECULE TYPE: protein ( x i ) SEQUENCE DESCRIPTION: SEQ ID NO:129:

| Gln | Val | Gln | Leu | Gln | Gln | Ser | Gly | Ala | Glu | Leu | Ala | Ser | Pro | Gly | Ala |
|---|---|---|---|---|---|---|---|---|---|---|---|---|---|---|---|
| 1 | | | | 5 | | | | | 10 | | | | | 15 | |

| Ser | Val | Thr | Leu | Ser | Cys | Lys | Ala | Ser | Gly | Tyr | Thr | Phe | Thr | Asp | His |
|---|---|---|---|---|---|---|---|---|---|---|---|---|---|---|---|
| | | | 20 | | | | | 25 | | | | | 30 | | |

| Ile | Met | Asn | Trp | Val | Lys | Lys | Arg | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Arg | Ile | Phe | Pro | Val | Ser | Gly | Glu | Thr | Asn | Tyr | Asn | Gln | Phe | Met |
|---|---|---|---|---|---|---|---|---|---|---|---|---|---|---|---|
| | 50 | | | | | 55 | | | | | 60 | | | | |

| Gly | Lys | Ala | Arg | Phe | Ser | Val | Asp | Arg | Ser | Ser | Ser | Thr | Val | Ser | Met |
|---|---|---|---|---|---|---|---|---|---|---|---|---|---|---|---|
| 65 | | | | | 70 | | | | | 75 | | | | | 80 |

| Val | Leu | Asn | Ser | Leu | Thr | Ser | Glu | Asp | Pro | Ala | Val | Tyr | Tyr | Cys | Asp |
|---|---|---|---|---|---|---|---|---|---|---|---|---|---|---|---|
| | | | | 85 | | | | | 90 | | | | | 95 | |

Leu ( 2 ) INFORMATION FOR SEQ ID NO:130:

( i ) SEQUENCE CHARACTERISTICS:
( A ) LENGTH: 98 amino acids
( B ) TYPE: amino acid
( D ) TOPOLOGY: linear ( i i ) MOLECULE TYPE: protein ( x i ) SEQUENCE DESCRIPTION: SEQ ID NO:130:

| Gln | Met | Gln | Leu | Val | Gln | Ser | Gly | Pro | Glu | Val | Lys | Lys | Pro | Gly | Thr |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Phe | Thr | Phe | Thr | Ser | Ser |
|---|---|---|---|---|---|---|---|---|---|---|---|---|---|---|---|
| | | | 20 | | | | | 25 | | | | | 30 | | |

| Ala | Val | Gln | Trp | Val | Arg | Gln | Ala | Arg | Gly | Gln | Arg | Leu | Glu | Trp | Ile |
|---|---|---|---|---|---|---|---|---|---|---|---|---|---|---|---|
| | | 35 | | | | | 40 | | | | | 45 | | | |

| Gly | Trp | Ile | Val | Val | Gly | Ser | Gly | Asn | Thr | Asn | Tyr | Ala | Gln | Lys | Phe |
|---|---|---|---|---|---|---|---|---|---|---|---|---|---|---|---|
| | 50 | | | | | 55 | | | | | 60 | | | | |

| Gln | Glu | Arg | Val | Thr | Ile | Thr | Arg | Asp | Met | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

Ala Ala ( 2 ) INFORMATION FOR SEQ ID NO:131:

( i ) SEQUENCE CHARACTERISTICS:
( A ) LENGTH: 126 base pairs
( B ) TYPE: nucleic acid
( C ) STRANDEDNESS: double
( D ) TOPOLOGY: linear ( i i ) MOLECULE TYPE: DNA ( i x ) FEATURE:
( A ) NAME/KEY: CDS
( B ) LOCATION: 1..126
( D ) OTHER INFORMATION: /transl_except=(pos: 115 .. 117,
aa: Glu)

( i x ) FEATURE:
( A ) NAME/KEY: sig_peptide
( B ) LOCATION: 1..24

( i x ) FEATURE:
( A ) NAME/KEY: mat_peptide
( B ) LOCATION: 25..126

( i x ) FEATURE:

(A) NAME/KEY: misc_feature
(B) LOCATION: 115..117
(D) OTHER INFORMATION: /label=amber
/ note="Suppressible translational stop codon."

(xi) SEQUENCE DESCRIPTION: SEQ ID NO:131:

| GTT | GTT | CCT | TTC | TAT | TCT | CAG | AGT | GCA | CAG | GTC | CAA | CTG | CAG | GTC | GAC | 48 |
|---|---|---|---|---|---|---|---|---|---|---|---|---|---|---|---|---|
| Val | Val | Pro | Phe | Tyr | Ser | Gln | Ser | Ala | Gln | Val | Gln | Leu | Gln | Val | Asp | |
| -8 | | | -5 | | | | | 1 | | | | 5 | | | | |

| CTC | GAG | ATC | AAA | CGG | GCG | GCC | GCA | GAA | CAA | AAA | CTC | ATC | TCA | GAA | GAG | 96 |
|---|---|---|---|---|---|---|---|---|---|---|---|---|---|---|---|---|
| Leu | Glu | Ile | Lys | Arg | Ala | Ala | Ala | Glu | Gln | Lys | Leu | Ile | Ser | Glu | Glu | |
| | 10 | | | | 15 | | | | | 20 | | | | | | |

| GAT | CTG | AAT | GGG | GCC | GCA | TAG | ACT | GTT | GAA | 126 |
|---|---|---|---|---|---|---|---|---|---|---|
| Asp | Leu | Asn | Gly | Ala | Ala | Glu | Thr | Val | Glu | |
| 25 | | | | | 30 | | | | | |

(2) INFORMATION FOR SEQ ID NO:132:

(i) SEQUENCE CHARACTERISTICS:
      (A) LENGTH: 162 base pairs
      (B) TYPE: nucleic acid
      (C) STRANDEDNESS: double
      (D) TOPOLOGY: linear (ii) MOLECULE TYPE: DNA (ix) FEATURE:
      (A) NAME/KEY: CDS
      (B) LOCATION: 1..162
      (D) OTHER INFORMATION: /transl_except=(pos: 151 .. 153,
         aa: Glu)

(ix) FEATURE:
      (A) NAME/KEY: sig_peptide
      (B) LOCATION: 1..63

(ix) FEATURE:
      (A) NAME/KEY: mat_peptide
      (B) LOCATION: 64..162

(ix) FEATURE:
      (A) NAME/KEY: misc_feature
      (B) LOCATION: 151..153
      (D) OTHER INFORMATION: /note="Suppressible translational
         stop codon."

(xi) SEQUENCE DESCRIPTION: SEQ ID NO:132:

| GTG | AAA | AAA | TTA | TTA | TTC | GCA | ATT | CCT | TTA | GTT | GTT | TTC | TAT | GCG | GCC | 48 |
|---|---|---|---|---|---|---|---|---|---|---|---|---|---|---|---|---|
| Val | Lys | Lys | Leu | Leu | Phe | Ala | Ile | Pro | Leu | Val | Val | Phe | Tyr | Ala | Ala | |
| -21 | -20 | | | | | -15 | | | | | -10 | | | | | |

| CAG | CCG | GCC | ATG | GCC | CAG | GTC | CAA | CTG | CAG | GTC | GAC | CTC | GAG | ATC | AAA | 96 |
|---|---|---|---|---|---|---|---|---|---|---|---|---|---|---|---|---|
| Gln | Pro | Ala | Met | Ala | Gln | Val | Gln | Leu | Gln | Val | Asp | Leu | Glu | Ile | Lys | |
| -5 | | | | | 1 | | | | 5 | | | | | | 10 | |

| CGG | GCG | GCC | GCA | GAA | CAA | AAA | CTC | ATC | TCA | GAA | GAG | GAT | CTG | AAT | GGG | 144 |
|---|---|---|---|---|---|---|---|---|---|---|---|---|---|---|---|---|
| Arg | Ala | Ala | Ala | Glu | Gln | Lys | Leu | Ile | Ser | Glu | Glu | Asp | Leu | Asn | Gly | |
| | | | 15 | | | | | 20 | | | | | 25 | | | |

| GCC | GCA | TAG | ACT | GTT | GAA | 162 |
|---|---|---|---|---|---|---|
| Ala | Ala | Glu | Thr | Val | Glu | |
| | | 30 | | | | |

(2) INFORMATION FOR SEQ ID NO:133:

(i) SEQUENCE CHARACTERISTICS:
      (A) LENGTH: 112 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:133:

5,565,332

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20              25                  30

Ser Met Asn Trp Val Arg Gln Ala Pro Gly Lys Gly Leu Glu Trp Val
        35              40                  45

Ser Tyr Ile Ser Ser Ser Ser Gly Thr Ile Tyr Tyr Ala Asp Ser Val
    50              55                  60

Lys Gly Arg Phe Thr Ile Ser Arg Asp Asn Ala Lys Asn Ser Leu Tyr
65                  70              75                      80

Leu Gln Met Asn Ser Leu Arg Asp Glu Asp Thr Ala Val Tyr Tyr Cys
            85              90                      95

Ala Ser Ser Ser Trp Tyr Gly Gly Tyr Gly Asp Tyr Trp Gly Gln Gly
            100             105                 110

( 2 ) INFORMATION FOR SEQ ID NO:134:

( i ) SEQUENCE CHARACTERISTICS:
      ( A ) LENGTH: 111 amino acids
      ( B ) TYPE: amino acid
      ( D ) TOPOLOGY: linear ( i i ) MOLECULE TYPE: protein ( x i ) SEQUENCE DESCRIPTION: SEQ ID NO:134:

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20              25                  30

Ser Met Asn Trp Val Arg Gln Ala Pro Gly Lys Gly Leu Glu Trp Val
        35              40                  45

Ser Tyr Ile Ser Ser Ser Ser Thr Ile Tyr Tyr Ala Asp Ser Val
    50              55                  60

Lys Gly Arg Phe Thr Ile Ser Arg Asp Asn Ala Lys Asn Ser Leu Tyr
65                  70              75                      80

Leu Gln Met Asn Ser Leu Arg Ala Glu Asp Thr Ala Val Tyr Tyr Cys
            85              90                      95

Ala Arg Ser Val Asp Ser Tyr Gly Met Asp Val Trp Gly Gln Gly
            100             105                 110

( 2 ) INFORMATION FOR SEQ ID NO:135:

( i ) SEQUENCE CHARACTERISTICS:
      ( A ) LENGTH: 120 amino acids
      ( B ) TYPE: amino acid
      ( D ) TOPOLOGY: linear ( i i ) MOLECULE TYPE: protein ( x i ) SEQUENCE DESCRIPTION: SEQ ID NO:135:

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20              25                  30

Ala Met His Trp Val Arg Gln Ala Pro Gly Lys Gly Leu Glu Trp Val
        35              40                  45

Ala Val Ile Ser Tyr Asp Gly Ser Asn Lys Tyr Tyr Ala Asp Ser Val
    50              55                  60

Lys Gly Arg Phe Thr Ile Ser Arg Asp Asn Ser Lys Asn Thr Leu Tyr

|    |    |    | 65  |     |     |     |     | 70  |     |     |     |     | 75  |     |     |     |     | 80  |
|----|----|----|-----|-----|-----|-----|-----|-----|-----|-----|-----|-----|-----|-----|-----|-----|-----|-----|

Leu Gln Met Asn Ser Leu Arg Ala Glu Asp Thr Ala Val Tyr Tyr Cys
                    85                  90                  95

Ala Lys Gly Gly Leu Gly Thr Tyr Tyr Tyr Asp Ser Ser Gly His Lys
            100                 105                 110

Gly Phe Asp Pro Trp Gly Gln Gly
            115             120

( 2 ) INFORMATION FOR SEQ ID NO:136:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:136:

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Tyr Pro Ser Arg Gly Leu Glu
            35                  40                  45

Trp Leu Gly Arg Thr Tyr Tyr Arg Ser Lys Trp Tyr Asn Asn Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Lys Ala Val
            85                  90                  95

Tyr Tyr Cys Asp Leu
            100

( 2 ) INFORMATION FOR SEQ ID NO:137:

( i ) SEQUENCE CHARACTERISTICS:
        ( A ) LENGTH: 101 amino acids
        ( B ) TYPE: amino acid
        ( D ) TOPOLOGY: linear ( i i ) MOLECULE TYPE: protein ( x i ) SEQUENCE DESCRIPTION: SEQ ID NO:137:

Gln Val Gln Leu Val Gln Ser Gly Pro Gly Leu Val Lys Pro Ser Gln
1               5                   10                  15

Thr Leu Ser Leu Ile Arg Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ile Ile Asn Pro Gly Thr Ser Lys Asn
65                  70                  75                  80

Gln Phe Ser Leu Gln Leu Ser Ser Val Thr Pro Glu Asp Thr Ala Val
            85                  90                  95

Tyr Tyr Cys Asp Leu
            100

( 2 ) INFORMATION FOR SEQ ID NO:138:

( i ) SEQUENCE CHARACTERISTICS:
   ( A ) LENGTH: 101 amino acids
   ( B ) TYPE: amino acid
   ( D ) TOPOLOGY: linear ( i i ) MOLECULE TYPE: protein ( x i ) SEQUENCE DESCRIPTION: SEQ ID NO:138:

| Gln | Val | Gln | Leu | Gln | Glu | Ser | Gly | Pro | Gly | Leu | Val | Lys | Pro | Ser | Gln |
|---|---|---|---|---|---|---|---|---|---|---|---|---|---|---|---|
| 1 | | | | 5 | | | | | 10 | | | | | 15 | |
| Thr | Leu | Ser | Leu | Thr | Cys | Ala | Ile | Ser | Gly | Asp | Ser | Val | Ser | Ser | Lys |
| | | | 20 | | | | | 25 | | | | | 30 | | |
| Ser | Ala | Thr | Trp | Asn | Trp | Ile | Arg | Gln | Ser | Pro | Ser | Arg | Gly | Leu | Glu |
| | | 35 | | | | | 40 | | | | | 45 | | | |
| Trp | Leu | Gly | Arg | Thr | Tyr | Tyr | Arg | Ser | Arg | Trp | Tyr | Thr | Asp | Tyr | Ala |
| | | 50 | | | | 55 | | | | | 60 | | | | |
| Thr | Ser | Val | Gln | Ser | Arg | Ile | Thr | Ile | Asn | Pro | Asp | Thr | Ser | Lys | Asn |
| 65 | | | | | 70 | | | | | 75 | | | | | 80 |
| Gln | Phe | Ser | Leu | Gln | Leu | Asn | Ser | Met | Thr | Pro | Glu | Asp | Thr | Ala | Val |
| | | | | 85 | | | | | 90 | | | | | 95 | |
| Tyr | Tyr | Cys | Asp | Leu | | | | | | | | | | | |
| | | | | 100 | | | | | | | | | | | |

( 2 ) INFORMATION FOR SEQ ID NO:139:

( i ) SEQUENCE CHARACTERISTICS:
      ( A ) LENGTH: 101 amino acids
      ( B ) TYPE: amino acid
      ( D ) TOPOLOGY: linear ( i i ) MOLECULE TYPE: protein ( x i ) SEQUENCE DESCRIPTION: SEQ ID NO:139:

| Gln | Val | Gln | Leu | Gln | Gln | Ser | Gly | Pro | Gly | Leu | Met | Lys | Pro | Ser | Gln |
|---|---|---|---|---|---|---|---|---|---|---|---|---|---|---|---|
| 1 | | | | 5 | | | | | 10 | | | | | 15 | |
| Thr | Leu | Ser | Leu | Thr | Cys | Ala | Ile | Ser | Gly | Asp | Ser | Val | Ser | Ser | Ser |
| | | | 20 | | | | | 25 | | | | | 30 | | |
| Ser | Ser | Thr | Trp | Asp | Trp | Ile | Arg | Gln | Ser | Pro | Ser | Arg | Gly | Leu | Glu |
| | | 35 | | | | | 40 | | | | | 45 | | | |
| Trp | Leu | Gly | Arg | Thr | Tyr | Tyr | Arg | Ser | Lys | Trp | Tyr | Asn | Asp | Tyr | Ala |
| | | 50 | | | | 55 | | | | | 60 | | | | |
| Val | Ser | Val | Lys | Ser | Arg | Ile | Thr | Ile | Lys | Ala | Asp | Thr | Ser | Lys | Asn |
| 65 | | | | | 70 | | | | | 75 | | | | | 80 |
| Gln | Phe | Ser | Leu | Gln | Leu | Ser | Ser | Val | Thr | Pro | Glu | Asp | Thr | Ala | Val |
| | | | | 85 | | | | | 90 | | | | | 95 | |
| Tyr | Tyr | Cys | Asp | Pro | | | | | | | | | | | |
| | | | | 100 | | | | | | | | | | | |

( 2 ) INFORMATION FOR SEQ ID NO:140:

( i ) SEQUENCE CHARACTERISTICS:
      ( A ) LENGTH: 98 amino acids
      ( B ) TYPE: amino acid
      ( D ) TOPOLOGY: linear ( i i ) MOLECULE TYPE: protein ( x i ) SEQUENCE DESCRIPTION: SEQ ID NO:140:

| Gln | Val | Asn | Leu | Arg | Glu | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |
| Ser | Val | Lys | Val | Ser | Cys | Lys | Ala | Ser | Gly | Phe | Thr | Phe | Thr | Ser | Ser |
| | | | 20 | | | | | 25 | | | | | 30 | | |

Ala  Val  Gln  Trp  Val  Arg  Gln  Ala  Pro  Gly  Gln  Arg  Leu  Glu  Trp  Met
                          35                 40                      45

Gly  Gly  Ile  Ile  Pro  Ile  Phe  Gly  Thr  Ala  Asn  Tyr  Ala  Gln  Lys  Phe
                     50                      55                      60

Gln  Gly  Arg  Val  Thr  Ile  Thr  Ala  Asp  Glu  Ser  Thr  Ser  Thr  Ala  Tyr
                65                      70                 75                           80

Met  Glu  Leu  Ser  Ser  Leu  Gly  Ser  Glu  Asp  Ala  Ala  Val  Tyr  Tyr  Cys
                               85                      90                           95

Asp  Leu ( 2 ) INFORMATION FOR SEQ ID NO:141:

( i ) SEQUENCE CHARACTERISTICS:
        ( A ) LENGTH: 116 amino acids
        ( B ) TYPE: amino acid
        ( D ) TOPOLOGY: linear ( i i ) MOLECULE TYPE: protein ( x i ) SEQUENCE DESCRIPTION: SEQ ID NO:141:

Gln  Val  Gln  Leu  Val  Glu  Ser  Gly  Gly  Gly  Val  Val  Gln  Pro  Gly  Arg
                1                   5                      10                      15

Ser  Leu  Arg  Leu  Ser  Cys  Ala  Ala  Ser  Gly  Phe  Thr  Phe  Ser  Ser  Tyr
                               20                      25                      30

Ala  Met  His  Trp  Val  Arg  Gln  Ala  Pro  Gly  Lys  Gly  Leu  Glu  Trp  Val
                          35                 40                      45

Ala  Val  Ile  Ser  Tyr  Asp  Gly  Ser  Asn  Lys  Tyr  Tyr  Ala  Asp  Ser  Val
                     50                      55                      60

Lys  Gly  Arg  Phe  Thr  Ile  Ser  Arg  Asp  Asn  Ser  Lys  Asn  Thr  Leu  Tyr
                65                      70                 75                           80

Leu  Gln  Met  Asn  Ser  Leu  Arg  Ala  Glu  Asp  Thr  Ala  Val  Tyr  Tyr  Cys
                               85                      90                           95

Ala  Ser  Gly  Arg  Tyr  Cys  Ser  Gly  Gly  Ser  Cys  Ser  Pro  Phe  Asp  Tyr
                                    100                     105                     110

Trp  Gly  Gln  Gly
                          115

( 2 ) INFORMATION FOR SEQ ID NO:142:

( i ) SEQUENCE CHARACTERISTICS:
        ( A ) LENGTH: 48 amino acids
        ( B ) TYPE: amino acid
        ( D ) TOPOLOGY: linear ( i i ) MOLECULE TYPE: protein ( x i ) SEQUENCE DESCRIPTION: SEQ ID NO:142:

Met  Lys  Tyr  Leu  Leu  Pro  Thr  Ala  Ala  Ala  Gly  Leu  Leu  Leu  Leu  Ala
-22            -20                 -15                      -10

Ala  Gln  Pro  Ala  Met  Ala  Gln  Val  Gln  Leu  Gln  Val  Asp  Leu  Glu  Ile
         -5                       1                  5                        10

Lys  Arg  Ala  Ala  Ala  Glu  Gln  Lys  Leu  Ile  Ser  Glu  Glu  Asp  Leu  Asn
                    15                      20                           25

( 2 ) INFORMATION FOR SEQ ID NO:143:

( i ) SEQUENCE CHARACTERISTICS:
        ( A ) LENGTH: 42 amino acids
        ( B ) TYPE: amino acid
        ( D ) TOPOLOGY: linear (i i) MOLECULE TYPE: protein (x i) SEQUENCE DESCRIPTION: SEQ ID NO:143:

| Val | Val | Pro | Phe | Tyr | Ser | Gln | Ser | Ala | Gln | Val | Gln | Leu | Gln | Val | Asp |
|-----|-----|-----|-----|-----|-----|-----|-----|-----|-----|-----|-----|-----|-----|-----|-----|
| -8  |     |     | -5  |     |     |     |     | 1   |     |     |     | 5   |     |     |     |

| Leu | Glu | Ile | Lys | Arg | Ala | Ala | Ala | Glu | Gln | Lys | Leu | Ile | Ser | Glu | Glu |
|-----|-----|-----|-----|-----|-----|-----|-----|-----|-----|-----|-----|-----|-----|-----|-----|
|     | 10  |     |     |     |     | 15  |     |     |     |     | 20  |     |     |     |     |

| Asp | Leu | Asn | Gly | Ala | Ala | Glu | Thr | Val | Glu |
|-----|-----|-----|-----|-----|-----|-----|-----|-----|-----|
| 25  |     |     |     |     | 30  |     |     |     |     |

(2) INFORMATION FOR SEQ ID NO:144:

(i) SEQUENCE CHARACTERISTICS:
(A) LENGTH: 54 amino acids
(B) TYPE: amino acid
(D) TOPOLOGY: linear (i i) MOLECULE TYPE: protein (x i) SEQUENCE DESCRIPTION: SEQ ID NO:144:

| Val | Lys | Lys | Leu | Leu | Phe | Ala | Ile | Pro | Leu | Val | Val | Phe | Tyr | Ala | Ala |
|-----|-----|-----|-----|-----|-----|-----|-----|-----|-----|-----|-----|-----|-----|-----|-----|
| -21 | -20 |     |     |     |     | -15 |     |     |     |     | -10 |     |     |     |     |

| Gln | Pro | Ala | Met | Ala | Gln | Val | Gln | Leu | Gln | Val | Asp | Leu | Glu | Ile | Lys |
|-----|-----|-----|-----|-----|-----|-----|-----|-----|-----|-----|-----|-----|-----|-----|-----|
| -5  |     |     |     |     | 1   |     |     |     | 5   |     |     |     |     | 10  |     |

| Arg | Ala | Ala | Ala | Glu | Gln | Lys | Leu | Ile | Ser | Glu | Glu | Asp | Leu | Asn | Gly |
|-----|-----|-----|-----|-----|-----|-----|-----|-----|-----|-----|-----|-----|-----|-----|-----|
|     |     |     | 15  |     |     |     |     | 20  |     |     |     |     | 25  |     |     |

| Ala | Ala | Glu | Thr | Val | Glu |
|-----|-----|-----|-----|-----|-----|
|     |     | 30  |     |     |     |